(12) United States Patent
Morre et al.

(10) Patent No.: US 7,585,947 B2
(45) Date of Patent: Sep. 8, 2009

(54) IL-7 DRUG SUBSTANCE, COMPOSITION, PREPARATION AND USES

(75) Inventors: Michel Christian Morre, Boulogne Billancourt (FR); Brigitte Assouline, Courbevoie (FR); Pierre Cortez, Paris (FR); Anne Gregoire, Paris (FR)

(73) Assignee: Cytheris, Issy les Moulineaux (FR)

( * ) Notice: Subject to any disclaimer, the term of this patent is extended or adjusted under 35 U.S.C. 154(b) by 230 days.

(21) Appl. No.: 10/522,883

(22) PCT Filed: Aug. 6, 2003

(86) PCT No.: PCT/EP03/08701

§ 371 (c)(1), (2), (4) Date: Apr. 18, 2005

(87) PCT Pub. No.: WO2004/018681

PCT Pub. Date: Mar. 4, 2004

(65) Prior Publication Data

US 2005/0249701 A1 Nov. 10, 2005

Related U.S. Application Data

(60) Provisional application No. 60/475,881, filed on Jun. 5, 2003.

(30) Foreign Application Priority Data

Aug. 8, 2002 (EP) .................................. 02291996

(51) Int. Cl.
*C07K 14/52* (2006.01)
*C07K 14/00* (2006.01)
*C07K 1/00* (2006.01)
*A61K 38/00* (2006.01)

(52) U.S. Cl. ..................... 530/351; 530/350; 530/412; 514/2

(58) Field of Classification Search ................ None
See application file for complete search history.

(56) References Cited

U.S. PATENT DOCUMENTS

| | | | | |
|---|---|---|---|---|
| 4,965,195 A | * | 10/1990 | Namen et al. | 435/69.52 |
| 5,223,408 A | * | 6/1993 | Goeddel et al. | 435/69.3 |
| 5,328,988 A | * | 7/1994 | Namen et al. | 530/351 |
| 5,459,058 A | | 10/1995 | Leder et al. | |
| 5,705,149 A | * | 1/1998 | Namen et al. | 424/85.2 |
| 5,714,141 A | * | 2/1998 | Ho et al. | 424/85.2 |
| 5,728,680 A | * | 3/1998 | Morozov et al. | 514/19 |
| 2002/0058791 A1 | * | 5/2002 | Goldschneider et al. | 530/351 |
| 2005/0164352 A1 | | 7/2005 | Lauder et al. | |
| 2008/0206190 A1 | | 8/2008 | Morre et al. | |

FOREIGN PATENT DOCUMENTS

| EP | 0314415 A2 | 5/1989 |
|---|---|---|
| WO | WO 96/04306 | 2/1996 |
| WO | WO 99/03887 | 1/1999 |
| WO | WO 00/17362 | 3/2000 |
| WO | WO 01/75140 | 10/2001 |
| WO | WO 2007/010401 | 1/2007 |

OTHER PUBLICATIONS

Cosenza et al., Prot. Sci., 2000, 9:916-926.*
Kroemer, et al., Protein Engineering, 1996, 9(6):493-498.*
Srinivasan et al., Protein Engineering, 1993, vol. 6, suppl., pp. 107.*
Totsuka et al., J. Immunol., 2007, 178(8):4737-48.*
Lai et al., J. Immunol., 2001, 167:3550-3554.*
Srinivasan et al, Protein Engineering, 1993, vol. 6, No. Suppl., p. 107.
Kroemer et al, Protein Engineering, 1996, vol. 9, No. 6, pp. 493-498.
Goodwin et al, Proceedings of the National Academy of Sciences of USA, Jan. 1989, vol. 86, pp. 302-306.
Cosenza et al, The Journal of Biological Chemistry, Dec. 26, 1997, vol. 272, No. 52, pp. 32995-33000.
Cosenza et al, Protein Science, May 2000, vol. 9, No. 5, pp. 916-926.

* cited by examiner

*Primary Examiner*—Gary B Nickol
*Assistant Examiner*—Xiaozhen Xie
(74) *Attorney, Agent, or Firm*—Saliwanchik, Lloyd & Saliwanchik

(57) ABSTRACT

The present invention relates, generally, to the fields of immunology and molecular biology. The invention discloses, more particularly, new and improved interleukin-7 drug substances, corresponding specific immunoreactive antibodies, as well as compositions comprising the same, their preparation and uses. The invention also discloses methods to characterize the impurity profile of a r-hIL-7 drug substance used for therapeutic purpose, as well as optimized nucleotide sequences encoding mammalian IL-7, recombinant expression vectors and methods for preparing and purifying said polypeptides. The present invention stems from the unexpected discovery that the long term activity of recombinant IL-7 is mostly expressed by a specific conformer and that other conformers, potential product-related substances, product-related impurities, and process-related impurities, which would normally be included in the specification of the drug substance and/or drug product, although bioactive, should be strictly minimized because they are able to trigger an immune reaction against the desired IL-7 molecule.

42 Claims, 18 Drawing Sheets

Figure 1:
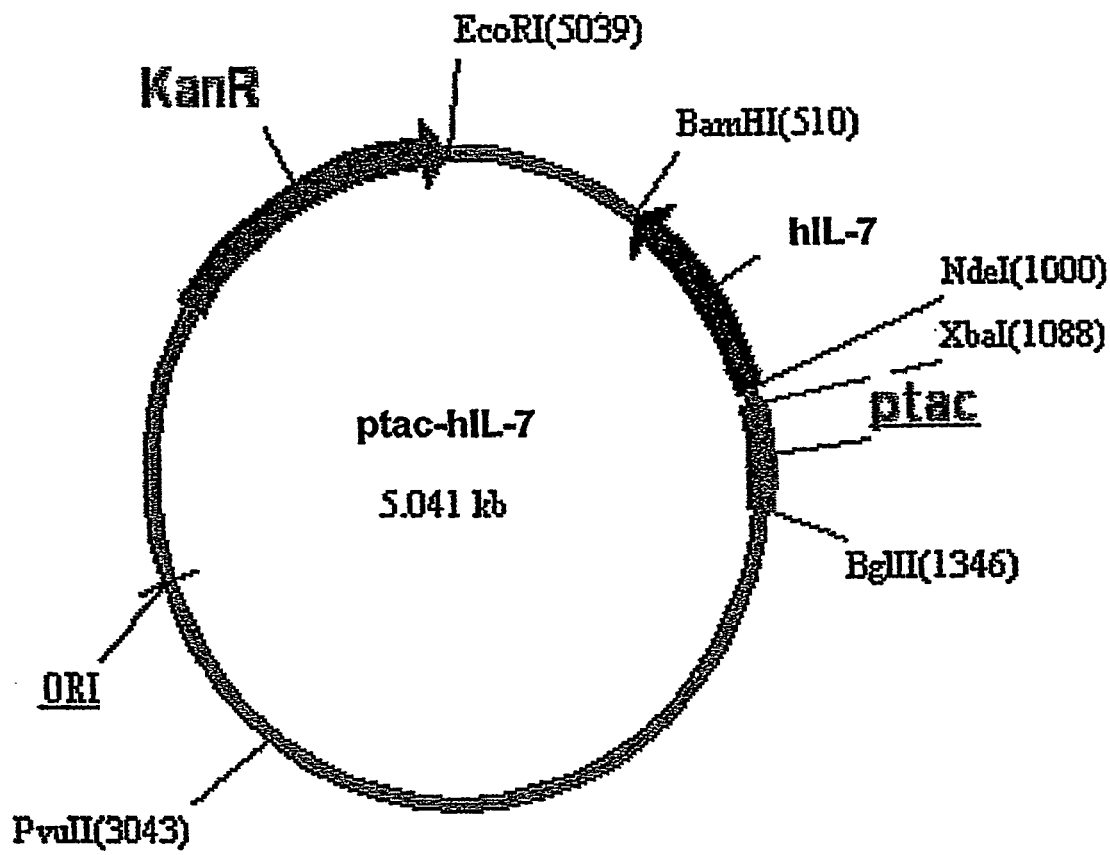

Lalign output for human IL7 vs. monkey IL7 cDNA

98.1% identity in 534 nt overlap; score: 2580 E(10,000): 3.3e-207

```
              10        20        30        40        50        60
human  ATGTTCCATGTTTCTTTTAGGTATATCTTTGGACTTCCTCCCCTGATCCTTGTTCTGTTG
monkey ATGTTCCATGTTTCTTTTAGGTATATCTTTGGACTTCCTCCCCTGATCCTTGTTCTGTTG 70        80        90       100       110       120
human  CCAGTAGCATCATCTGATTGTGATATTGAAGGTAAAGATGGCAAACAATATGAGAGTGTT
monkey CCAGTAGCATCATCTGATTGTGATATTGAAGGTAAAGATGGCAAACAATATGAGAGTGTT 130       140       150       160       170       180
human  CTAATGGTCAGCATCGATCAATTATTGGACAGCATGAAAGAAATTGGTAGCAATTGCCTG
monkey CTAATGGTCAGCATCGATCAATTATTGGACAGCATGAAAGAAATTGGTAGCAATTGCCTG 190       200       210       220       230       240
human  AATAATGAATTTAACTTTTTTAAAAGACATATCTGTGATGCTAATAAGGAAGGTATGTTT
monkey AATAATGAATTTAACTTTTTTAAAAGACATCTA TGTGATGATAATAAGGAAGGTATGTTT 250       260       270       280       290       300
human  TTATTCCGTGCTGCTCGCAAGTTGAGGCAATTTCTTAAAATGAATAGCACTGGTGATTTT
monkey TTATTCCGTGCTGCTCGCAAGTTGAGGCAATTTCTTAAAATGAATAGCACTGGTGATTTT 310       320       330       340       350       360
human  GATCTCCACTTATTAAAAGTTTCAGAAGGCACAACAATACTGTTGAACTGCACTGGCCAG
monkey GATCTCCACTTATTAAAAGTTTCAGAAGGCACAACAATACTGTTGAACTGCACCGGCAAG 370       380       390       400       410       420
human  GTTAAAGGAAGAAAACCAGCTGCCCTGGGTGAAGCCCAACCAACAAAGAGTTTGGAAGAA
monkey GTTAAAGGAAGAAAACCAGCTGCCCTGGGTGAACCCCAACCAACAAAGAGTTTGGAAGAA 430       440       450       460       470       480
human  AATAAATCTTTAAAGGAACAGAAAAAACTGAATGACTTGTGTTTCCTAAAGAGACTATTA
monkey AATAAATCTTTAAAGGAACAGAAAAAACTGAATGACTCATGTTTCCTAAAGAGACTACTA 490       500       510       520       530
human  CAAGAGATAAAAACTTGTTGGAATAAAATTTTGATGGGCACTAAAGAACACTGA
monkey CAAA AGATAAAAACTTGTTGGAATAAAATTTTGATGGGCACTAAAGAACACTGA
```

Figure 4

Comparison of:

(A) /tmp/www-sib/lalign.17549.1.seq sp|P13232|
IL7_HUMAN (IL7)INTERLEUKIN-7 PRECURSOR - 177 AA (B) /tmp/www-sib/lalign.17549.2.
SEQUENCE MONKEY IL7 PRECURSOR - 177 AA 96.6% identity in 177 aa overlap; score: 1144 E(10,000): 1.3e-95

```
               10         20         30         40         50         60
human  MFHVSFRYIFGLPPLILVLLPVASSDCDIEGKDGKQYESVLMVSIDQLLDSMKEIGSNCL
monkey MFHVSFRYIFGLPPLILVLLPVASSDCDIEGKDGKQYESVLMVSIDQLLDSMKEIGSNCL 70         80         90        100        110        120
human  NNEFNFFKRHICDANKEGMFLFRAARKLRQFLKMNSTGDFDLHLLKVSEGTTILLNCTGQ
monkey NNEFNFFKRHLCDDNKEGMFLFRAARKLRQFLKMNSTGDFDLHLLKVSEGTTILLNCTGK 130        140        150        160        170
human  VKGRKPAALGEAQPTKSLEENKSLKEQKKLNDLCFLKRLLQEIKTCWNKILMGTKEH
monkey VKGRKPAALGEPQPTKSLEENKSLKEQKKLNDSCFLKRLLQKIKTCWNKILMGTKEH
```

Figure 5

Human PS-IL-7 PCR product →

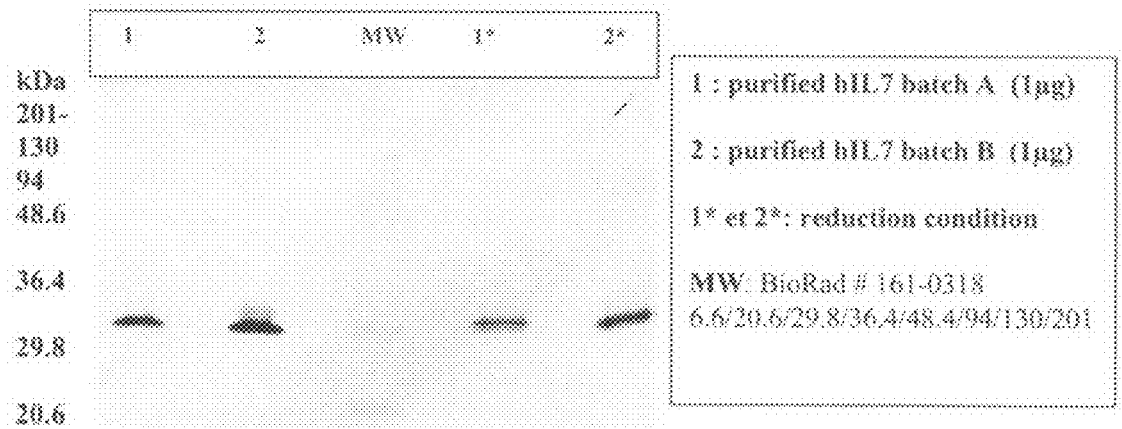
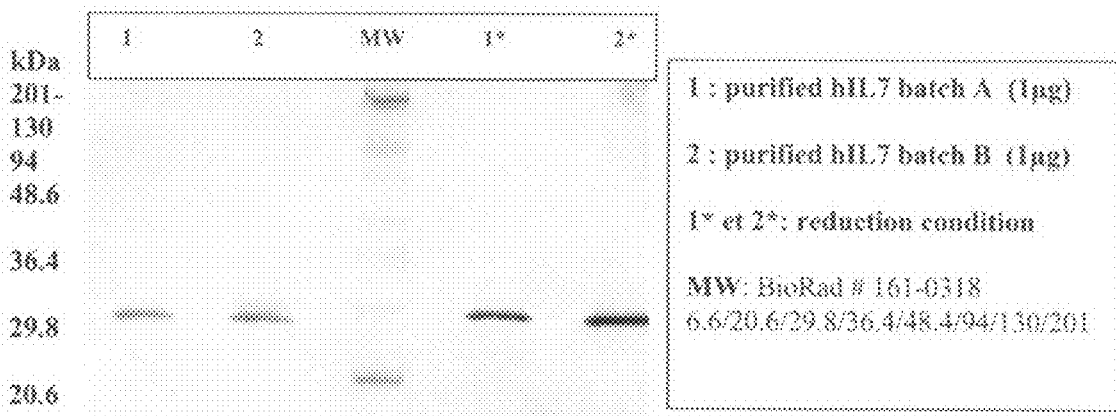
Figure 9

IL-7 DRUG SUBSTANCE, COMPOSITION, PREPARATION AND USES

This application is the U.S. national phase of international application PCT/EP2003/008701, filed 6 Aug. 2003, which claims benefit of EP 02291996.3, filed 8 Aug. 2002 and U.S. Provisional Application Ser. No. 60/475,881, filed 5 Jun. 2003, the entire contents of each of which is hereby incorporated by reference.

The present invention relates, generally, to the fields of immunology and molecular biology. The invention discloses, more particularly, new and improved interleukin-7 drug substances, corresponding specific immunoreactive antibodies, as well as compositions comprising the same, their preparation and uses. The invention also discloses methods to characterize the impurity profile of a r-hIL-7 drug substance used for therapeutic purpose, as well as optimized nucleotide sequences encoding mammalian IL-7, recombinant expression vectors and methods for preparing and purifying said polypeptides.

BACKGROUND OF THE INVENTION

B and T lymphocytes are the primary effector cells of the immune responses. Both cell classes are considered to derive ultimately from hematopoietic stem cells in the mammalian bone marrow, via progenitor or precursor cells representing distinguishable stages in the differentiation of each class. Mature T cells develop principally in the thymus, presumably from a precursor cell which migrates from the bone marrow to the thymus at an early stage of T lymphocyte development. Numbers of factors are active on mature peripheral B and T cells, including IL-1, IL-2, IL-4, IL-5, interferon gamma, BSF-2, neuroleukin, transforming growth factor beta and IL-7 (EP0314415).

"Interleukin-7" or "IL-7" refers to a mammalian endogenous secretory glycoprotein which is capable of inducing proliferation of bone marrow-derived lymphocyte progenitors and precursors, including the specialized precursors known as pre-B cells. Originally derived from the stromal element of a bone marrow cell line, IL-7 is also secreted by thymic cells, intestinal epithelial cells, keratinocytes and generally all lymphoid tissues. EP0314415 describes mammalian interleukin-7 proteins and DNAs encoding said proteins. The mature human IL-7 (r-hIL-7), exclusive of glycosylation, produced in *Escherichia coli*, which is described in EP0314415, exhibits a 17,387 Daltons molecular weight and displays a high activity in vitro on specific bioassays based on the proliferation of various lymphocytes populations. Alternative designations for this molecule are "pre-B cell growth factor" and "lymphopoietin-1". Indeed, originally, IL-7 was disclosed as a cytokine whose principal activity was induction of precursor B cell proliferation (Namen A. E. et al.; Journal of Experimental medicine; 1988; 167:988-1002). IL-7 has more recently been disclosed as being involved in the survival and proliferation of thymocytes (T-Cells) during early stage of T-cell development (Schluns K. S. et al.; Nature Immunology; 2000; 1(5):426-432). Fry and collaborators further identified IL-7 as a potent modulator of thymic-independent T-cell regeneration in a multifactorial action (Fry T. J. et al.; Blood; 2001; 97(6):1525-1533).

IL-7 has thus a great potential therapeutic use in the stimulation of the proliferation of T cell precursors, of antibody-secreting B cells, in the stimulation of antigen driven T-Cell peripheral expansion, and in the production of naïve T-Cells as well as other hematopoietic cell types. A particularly interesting therapeutic use of active IL-7 molecules is for immune reconstitution of lymphopenic patients: patients treated for a cancer, patients having received a bone marrow or a Stem Cell transfer, patients presenting an acquired or genetic immune deficiency, elderly patients or any patients having low CD4 count. Other interests reside in the ability of IL-7 to produce new naïve CD4 T-Cells or to expand specific pools in order to produce or increase specific immune responses (Vaccine enhancement).

In view of its therapeutic potential, there is considerable interest in developing technologies for producing biologically active IL-7 polypeptides and corresponding drug substances. There is much interest in producing IL-7 drug substances or pharmaceutical compositions that comply with the requirements of regulatory authorities and are suitable for efficient therapeutic uses.

A drug substance or pharmaceutical composition aimed at stimulating a global or specific immune reconstitution should be efficient on a long term, which implies that it should not trigger a specific immune reaction against its own active principle.

The present invention now shows, unexpectedly, that the long term activity of recombinant human IL-7 is mostly expressed by a specific 1-4; 2-5; 3-6 conformer. The present invention further shows that efficient drug substances should not only contain the above conformer as the major constituent, but should also be essentially devoid of other conformers or IL-7 molecular variants, previously considered as active products.

Up to the present invention, although the existence of the Cys: 1-4; 2-5; 3-6 conformer was hypothesized through computational modeling based on hypothetical GM-CSF or IL-4 conformation analogy, only IL-7 conformer exhibiting disulfide bridges Cys: 1-6; 2-5; 3-4 had been characterized by tryptic digest and mass spectrometry. This form was thought to constitute the major form of IL-7. In sharp contrast therewith, the invention now proposes new polypeptide products and pharmaceutical compositions which are essentially devoid of such conformer. The invention also discloses advantageous production and purification methods to produce such polypeptides and compositions, which exhibit a high biological activity with reduced risk of undesired response, such as anti-IL-7 immune responses.

The present invention thus discloses improved methods for the preparation and uses of said purified conformer of human IL-7, devoid of the above mentioned product related substances or impurities, which exhibits a particularly advantageous long term in vivo activity, able to favor global or specific immune responses.

SUMMARY OF THE INVENTION

A first object of the invention relates to a purified IL-7 conformer, said IL-7 conformer comprising the following three disulfide bridges: Cys: 1-4 (Cys2-Cys92); 2-5 (Cys34-Cys129); 3-6 (Cys47-Cys141). As disclosed further below, the IL-7 conformer is preferably a human recombinant IL-7 conformer, and may be glycosylated or unglycosylated.

An other object of this invention resides in a drug substance comprising an IL-7 conformer as described above and essentially devoid of product-related impurities and product related substances, particularly of other conformers or dimers of IL-7.

The invention also relates to the use of a drug substance as described above in the manufacture of a medicament ("drug product") or pharmaceutical composition.

The invention further relates to a pharmaceutical composition comprising an effective amount of a drug substance as described above and one or more pharmaceutically compatible carriers or excipients.

The invention also provides nucleic acid molecules coding for an IL-7 polypeptide. The nucleic acid molecules comprise a sequence encoding an IL-7 polypeptide, said sequence being optimized for the expression, in a recombinant host, of biologically active IL-7, particularly of an IL-7 conformer according to the invention. More specifically, the nucleic acid molecules provide for a limited expression of truncated IL-7 polypeptides and increase the yields of production of biologically active human IL-7 conformer. Particular sequences comprise a mutated or inactivated Shine-Dalgarno like sequence (e.g., SEQ ID NO: 1). Other particular sequences comprise a peptide signal causing efficient secretion of the polypeptide (e.g., SEQ ID NO: 3, 16, 18, 20 or 22). The invention also discloses and provides, for the first time, the nucleic acid sequence of the simian IL-7 (e.g., SEQ ID NO: 12, 20 or 22).

The invention further provides vectors comprising a nucleic acid as mentioned above and recombinant host cells comprising said nucleic acid or said vector. The nucleic acids and vectors may be used to produce recombinant mammalian IL-7 polypeptides in various competent host cells, as well as for gene therapy purposes.

The invention also provides an antibody specifically immunoreactive with a human IL-7 conformer according to the invention, hybridoma cell lines that produce said monoclonal antibody, as well as compositions suitable for diagnosis, assay or therapy comprising said antibody.

A further aspect of this invention is a method of producing a (recombinant) IL-7 conformer as described above, from prokaryotic or eukaryotic host cells, as well as a method of detecting or measuring the presence of an IL-7 conformer in a sample or to characterize a sample.

In a particular aspect, the method of producing an IL-7 conformer or a drug substance as defined above comprises:
a) providing a sample comprising IL-7 polypeptides, and
b) purifying an IL-7 conformer as described above.

The invention also relates to a method of characterizing or qualifying a sample, comprising detecting or measuring, in said sample, the presence of an IL-7 conformer as described above. Such method is particularly suited and important for validation of clinical lots or batches, whereby samples comprising excessive IL-7 molecular variants and/or product related impurities are discarded or further treated.

Another object of the invention relates to the use of an IL-7 conformer obtained by a method as described above, for the manufacture of a pharmaceutical composition to cause or modulate an immune response in a subject, particularly to induce a prolonged lymphopoiesis stimulation and/or to amplify an immune response.

The invention also relates to the use of an IL-7 conformer obtained by a method as described above, for the manufacture of a pharmaceutical composition to prevent or treat a disease associated with an immunodeficiency.

The invention further relates to the use of an IL-7 conformer according to the invention as a tool for experimental and pharmacological use in monkeys.

LEGENDS TO THE FIGURES

FIG. 1: Representation of the structure of *E Coli* expression vector ptac-hIL-7, which comprises SEQ ID NO:1.

Figure 2:
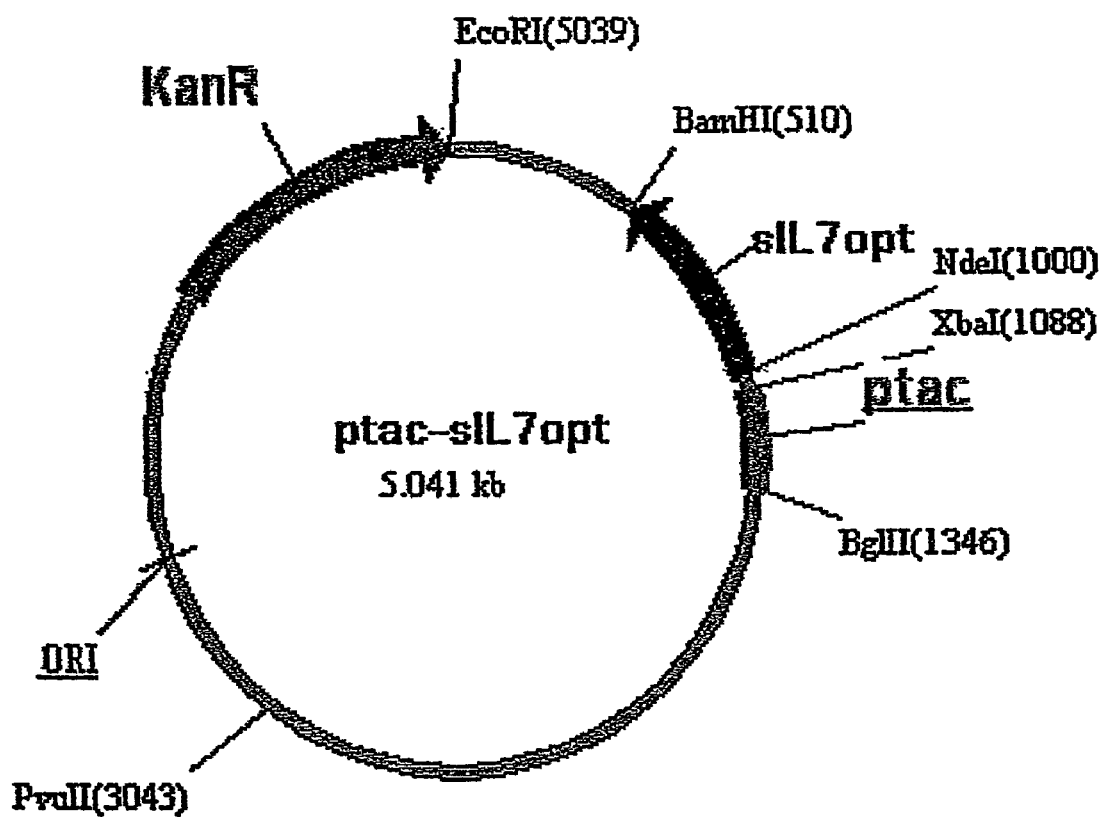

FIG. 2: Representation of the structure of *E Coli* expression vector ptac-sIL7opt, which comprises a sequence encoding simian IL-7 (corresponding to SEQ ID NO: 12 devoid of nucleotides no: 4 to 75, which encode the signal peptide).

Figure 3:
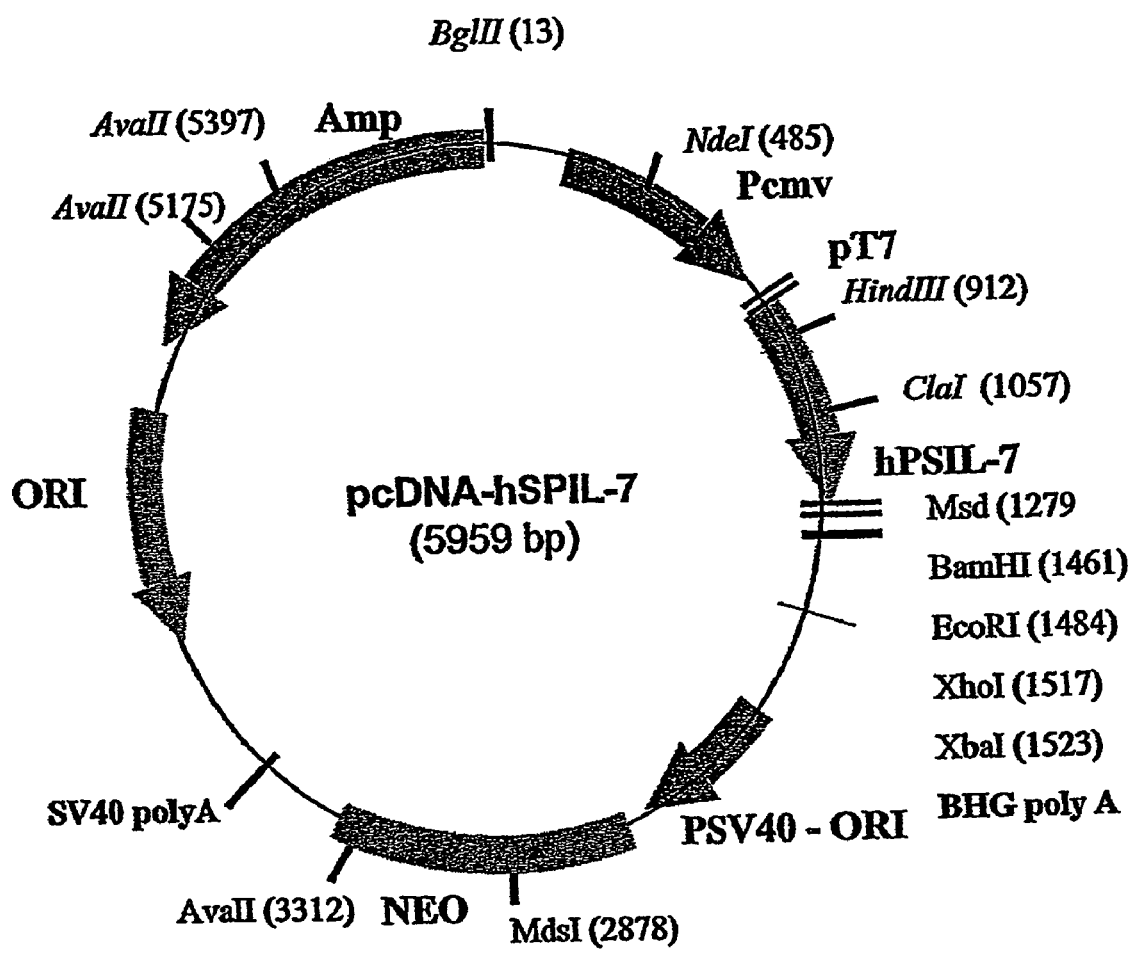

FIG. 3: Representation of the structure of mammalian expression vector pcDNA-hPSIL-7 containing SEQ ID NO:3, SEQ ID NO:16 or SEQ ID NO:18 (constitutive expression)

FIG. 4: Aligned nucleotide sequences of human and monkey cDNA.

FIG. 5: Aligned amino acid sequences of human and monkey protein.

Figure 6:
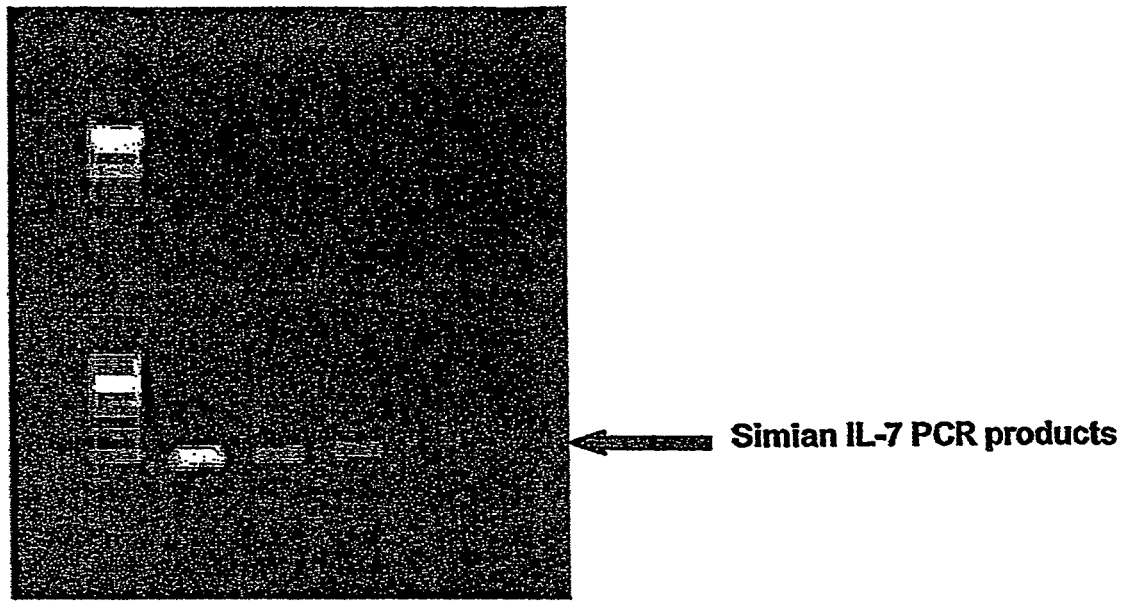

FIG. 6: Electrophoresis analysis of simian IL-7 PCR product.

Figure 7:
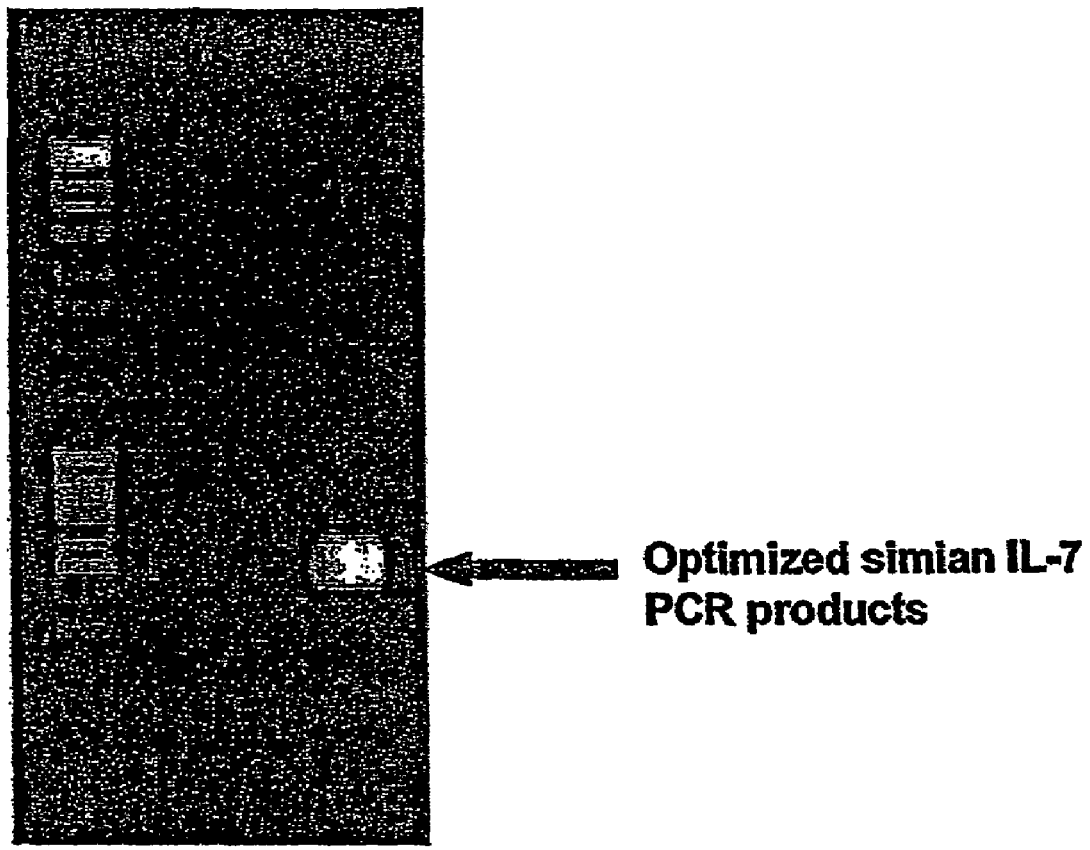

FIG. 7: Electrophoresis analysis of optimized simian IL-7 PCR product.

Figure 8:
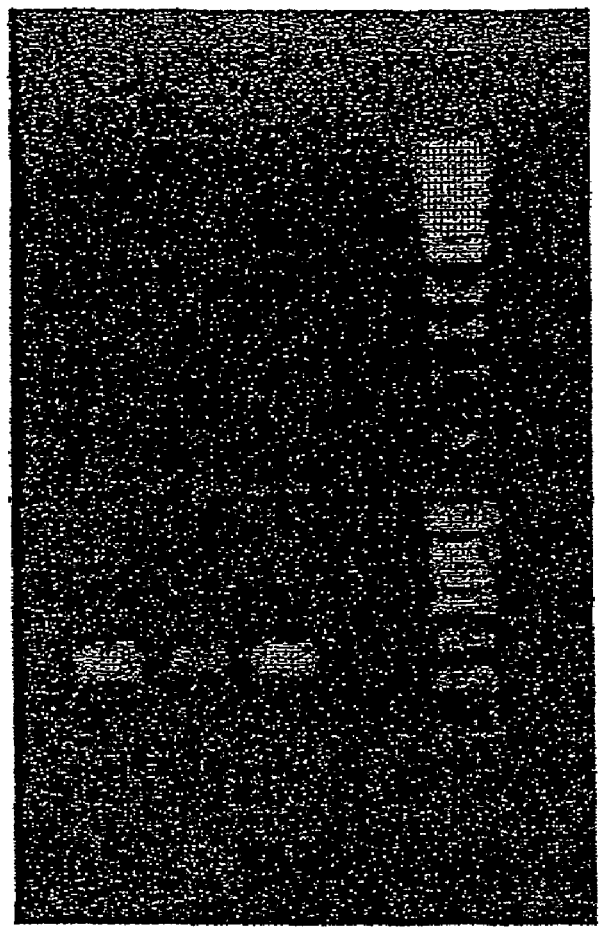

FIG. 8: Electrophoresis analysis of human PS-IL-7 PCR product.

FIG. 9: SDS-PAGE analysis of purified deglycosylated recombinant human IL-7 conformer: coomassie blue colored and silver stained.

Figure 10:
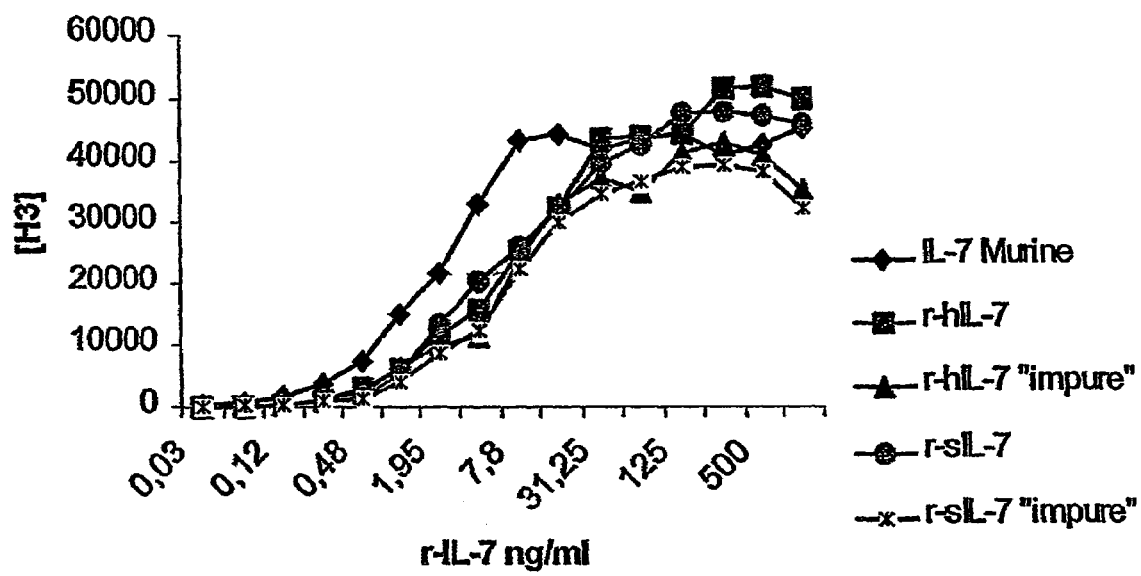

FIG. 10: Bioassay analysis of mammalian (human and simian) IL-7 proteins on pre-B cell line.

Figure 11:
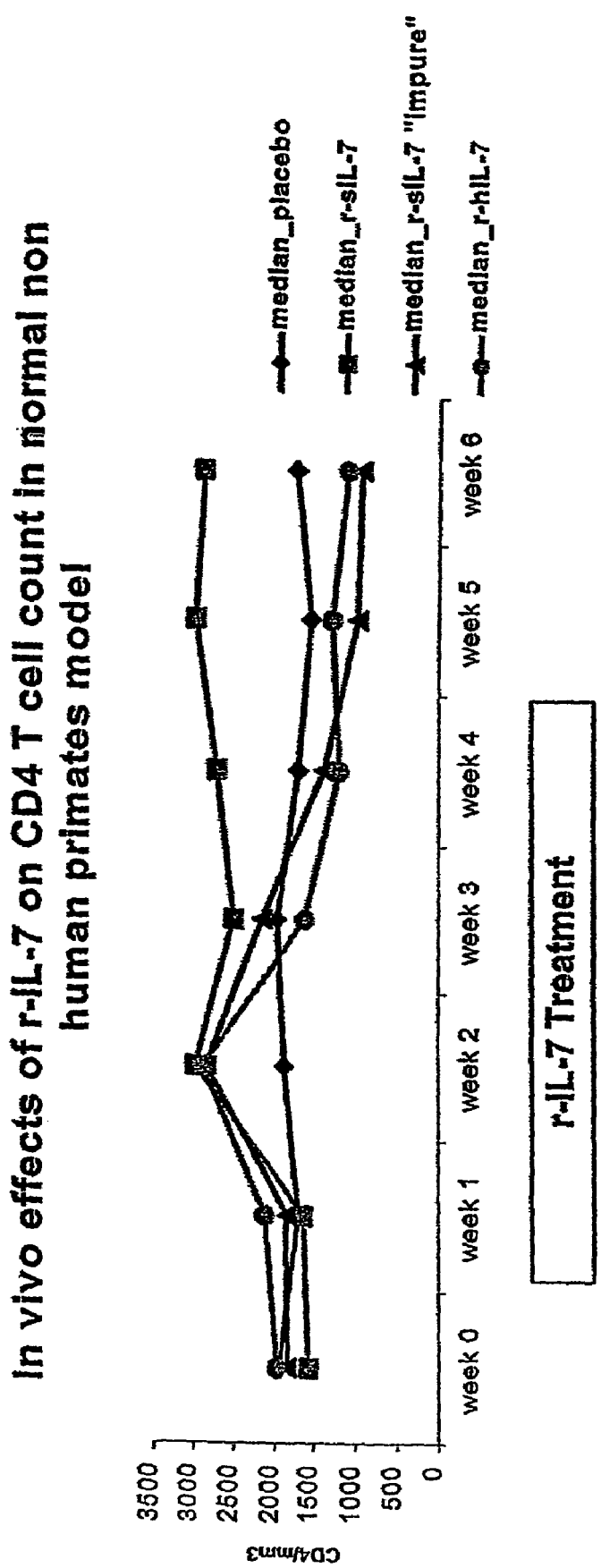

FIG. 11: Peripheral blood CD4 T cell count of normal monkey treated with various recombinant IL-7.

Figure 12:
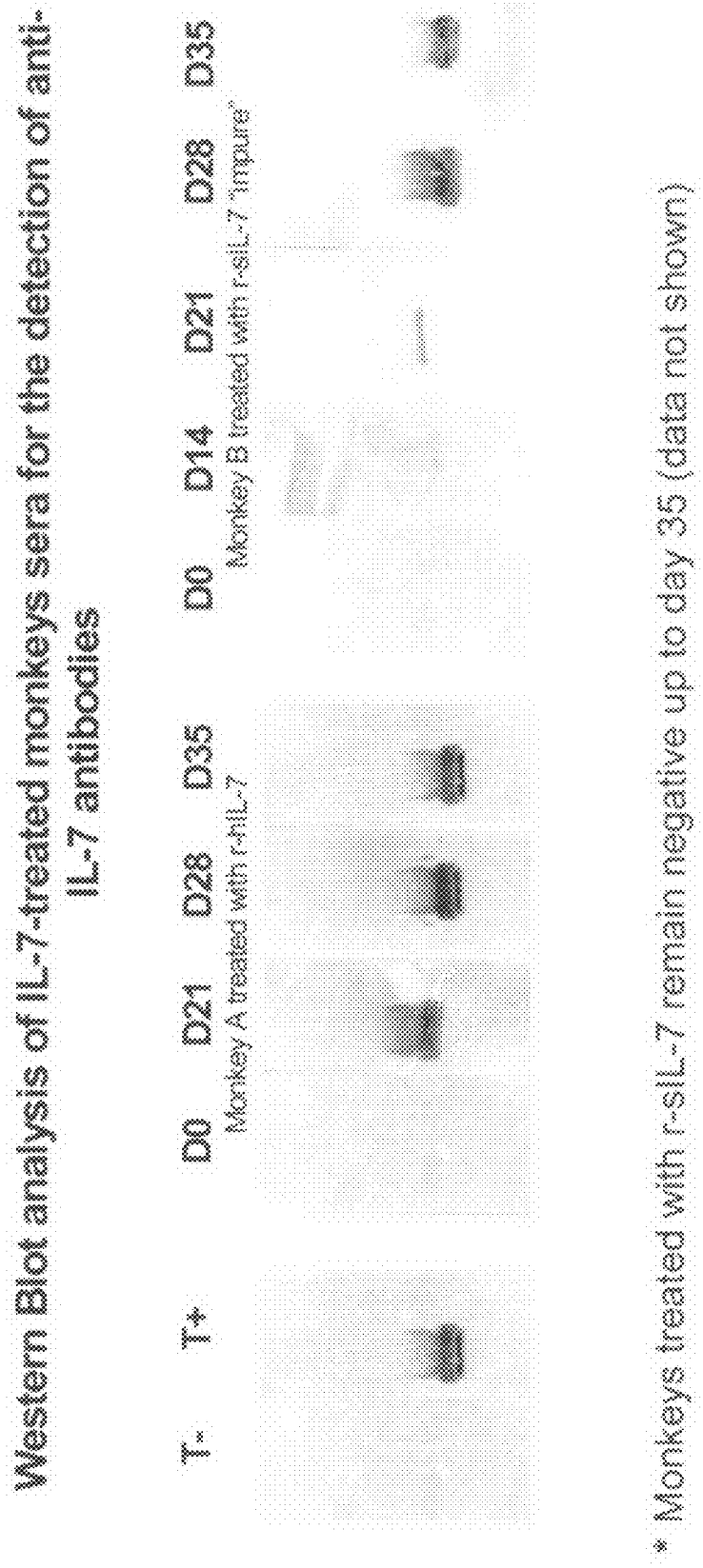

FIG. 12: Western Blot analysis of IL-7-treated monkey sera for the detection of anti-IL-7 antibodies.

Figure 13:
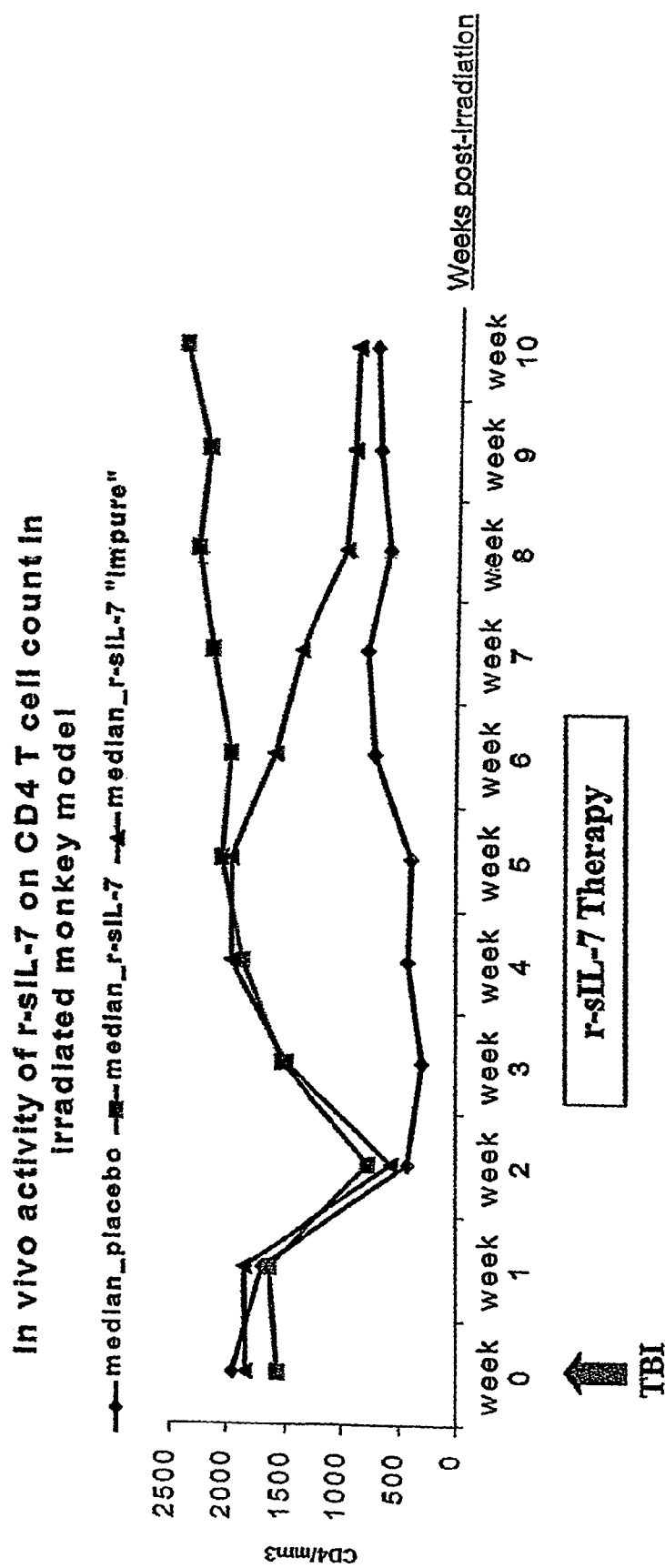

FIG. 13: Peripheral blood CD4 T cell count of irradiated monkey treated with various recombinant IL-7.

Figure 14:
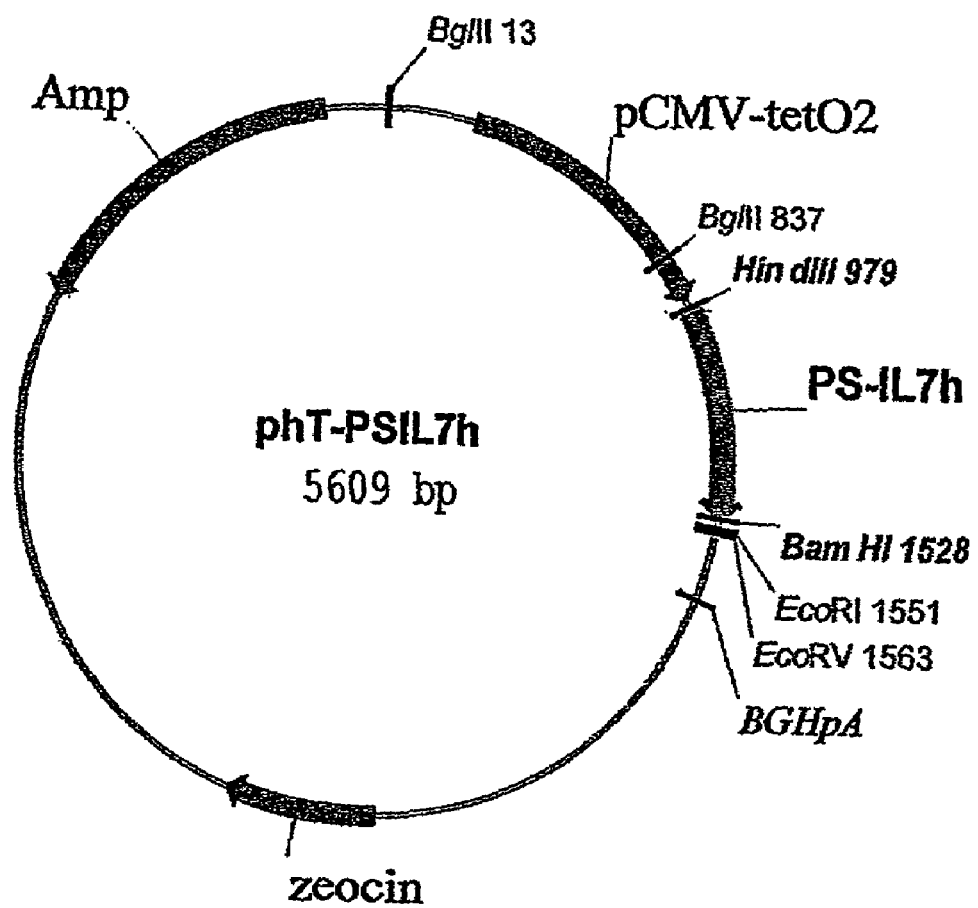

FIG. 14: Representation of the structure of a mammalian expression vector phT-PSIL-7h containing SEQ ID NO:3, SEQ ID NO:16 or SEQ ID NO:18 (Tetracycline inducible expression).

Figure 15:
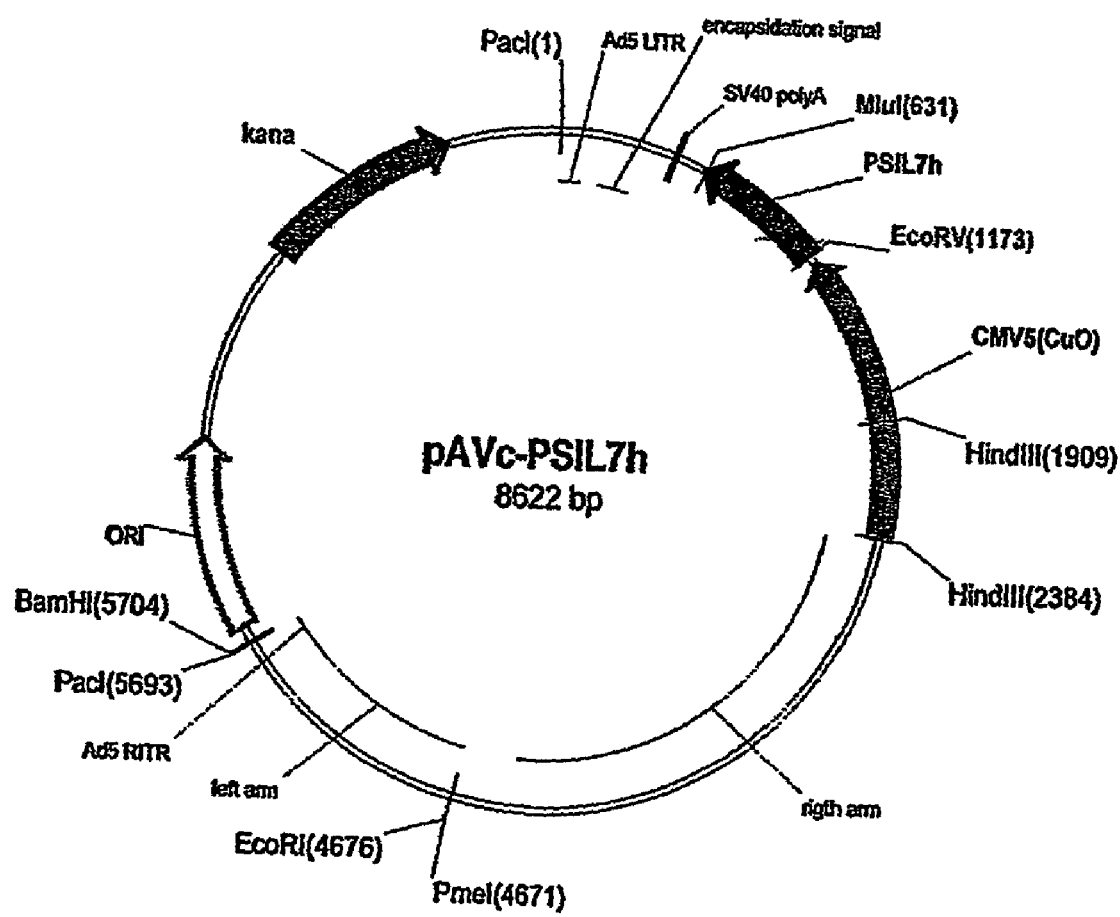

FIG. 15: Representation of the structure of a mammalian expression vector pAVc-PSIL-7h containing SEQ ID NO:3, SEQ ID NO:16 or SEQ ID NO:18. (Adenovirus transitory expression).

Figure 16:
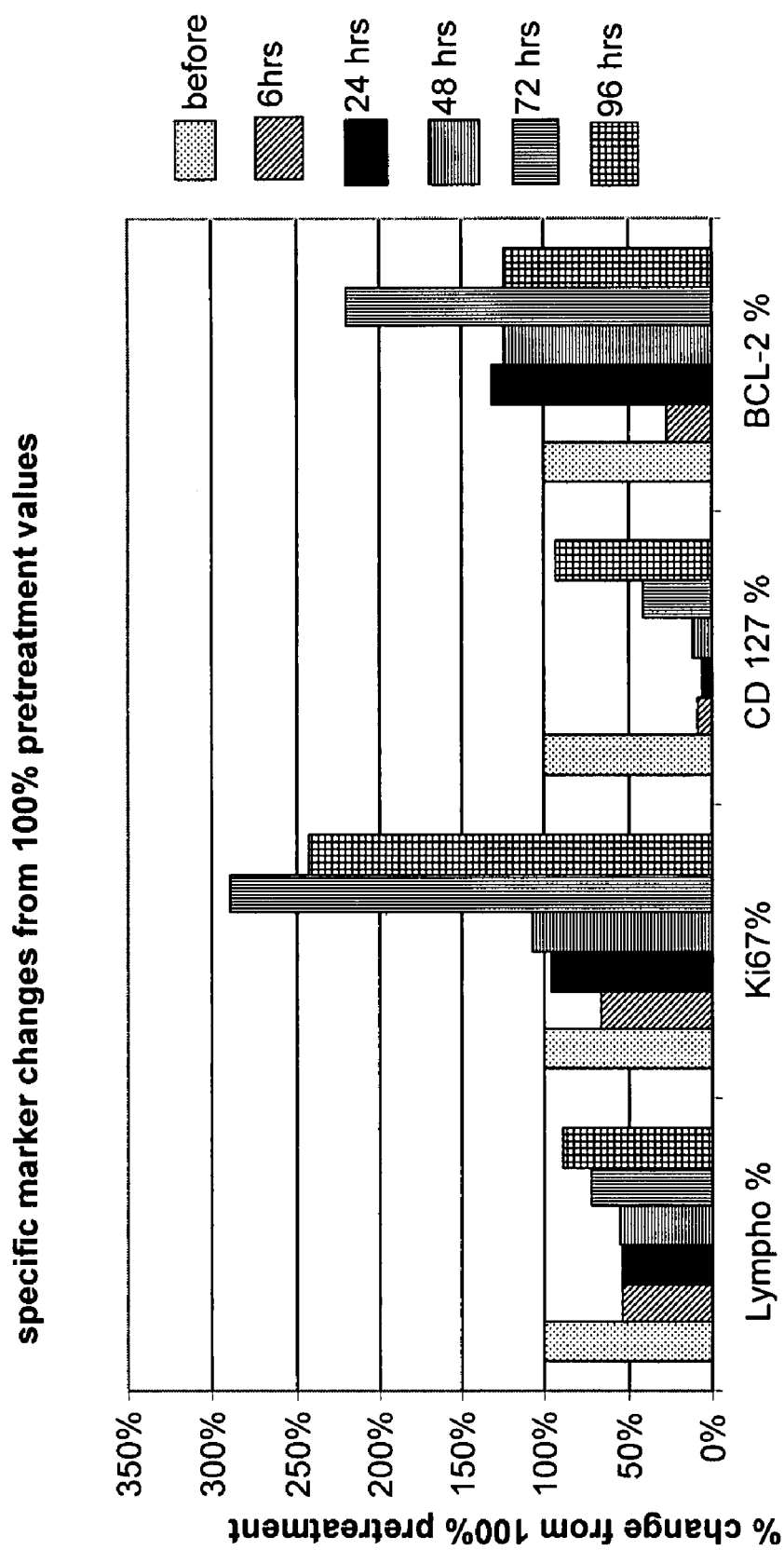

FIG. 16: Specific marker changes from 100% pretreatment values.

Figure 17:
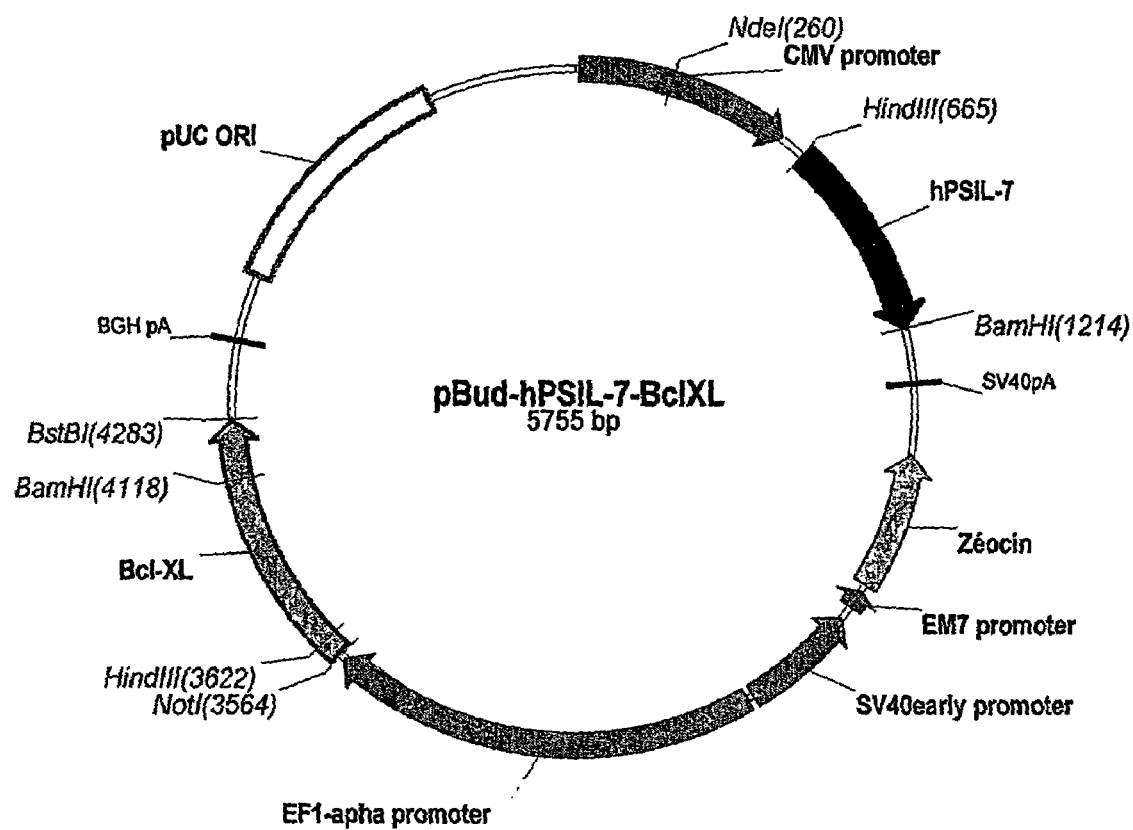

FIG. 17: Representation of the structure of a mammalian expression vector pBud-hPSIL-7-BclXL containing a human IL-7 sequence (SEQ ID NO:3, SEQ ID NO:16 or SEQ ID NO:18) and a sequence encoding a human Bcl-XL anti-apoptotic factor. (coexpression IL-7/BclXL).

Figure 18:
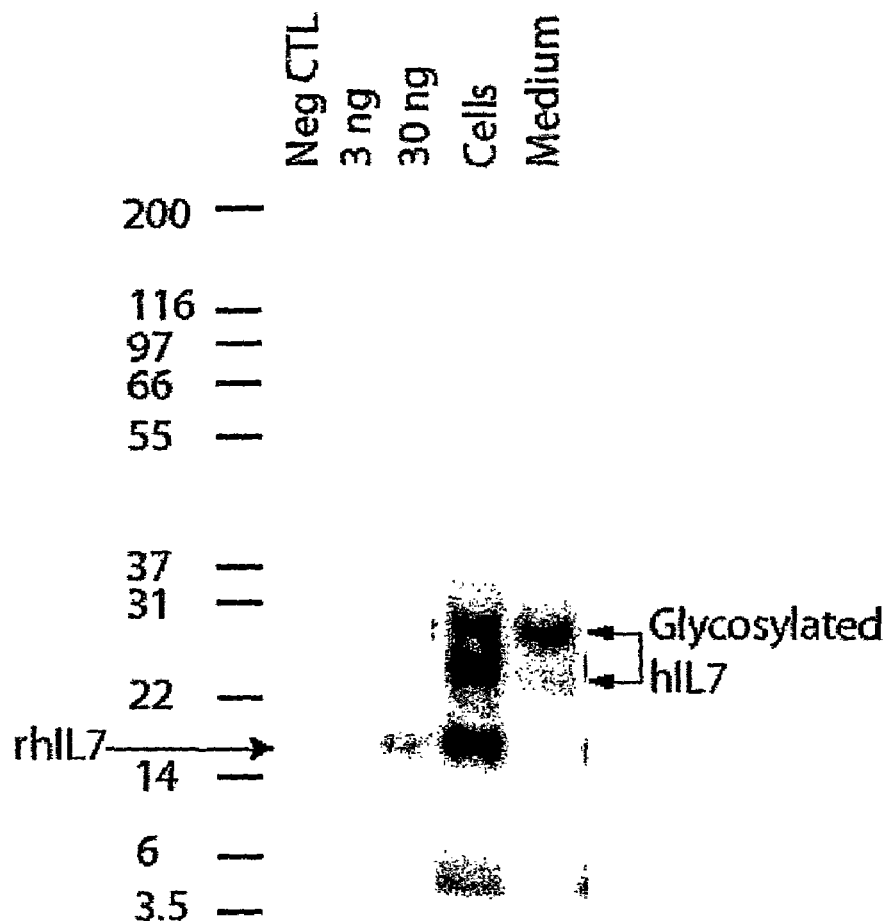

FIG. 18: hIL-7 expression in HEK293 cells by transient transfection.

DETAILED DESCRIPTION OF THE INVENTION

The present invention relates to a purified IL-7 conformer, said IL-7 conformer comprising the following three disulfide bridges: Cys: 1-4 (Cys2-Cys92); 2-5 (Cys34-Cys129); 3-6 (Cys47-Cys141), to drug substances and pharmaceutical compositions comprising said IL-7 conformer as well as to methods for their production and therapeutic uses. As will be disclosed further below, the IL-7 conformer is preferably a human recombinant IL-7 conformer, and may be glycosylated or unglycosylated. The human recombinant IL-7 conformer is preferentially glycosylated.

The invention is based on the unexpected discovery that the mid or long term in vivo biological activity of IL-7 is essentially attributable to a particular conformation of the molecule, not suspected so far, and that highly improved therapeutic efficiency is achieved by producing pharmaceutical compositions comprising said IL-7 conformer in a substantially pure form.

IL-7 Conformer

A first object of this invention resides in a purified or isolated IL-7 conformer, said IL-7 conformer comprising the following three disulfide bridges: Cys: 1-4 (Cys2-Cys92); 2-5 (Cys34-Cys129); 3-6 (Cys47-Cys141).

IL-7 primary sequence (human and simian) contains six highly conserved cysteine residues which are involved in the formation of three intramolecular disulfide bridges. As originally described by Goodwin, these disulfide bridges are necessary for bioactivity, beta-mercaptoethanol treatment of the IL-7 molecule fully abolishing its activity (Goodwin R. G. et al.; Proceedings of the National Academy of Sciences of the USA; 1989; 86:302-306). From this point, according to the rank of the cysteine residues positions, various conformers are possible, among which: 1-6; 2-5; 3-4 or 1-4; 2-5; 3-6 or 1-4; 2-6; 3-5 or 1-5; 2-4; 3-6, plus various other conformers, including contiguous bridges.

Various teams used computational chemistry in order to suggest a conformational model for the protein. From secondary structure prediction programs, Srinivasan and collaborators proposed the helical regions of IL-7 and, by analogy with the GM-CSF and IL-4 three dimensional structures, proposed a protein conformation which implied the following assignment for the three bridges: 1-4; 2-5; 3-6 (Srinivansan S. et al.; Protein Engineering (supplement); 1993; 6:107). Also, by homology modeling studies, Kroemer and collaborators predicted a 3D model of hIL-7, based on homology to structures of human IL-2, IL-4, GM-CSF and GH serving as templates and connecting them together in an up-up-down-down topology. In the context of this common topology, the 3D model of human IL-7 favored the hypothesis of a unique disulfide pattern: the 1-4; 2-5; 3-6 disulfide design (Kroemer R. T. et al.; Protein Engineering; 1996; 9(6):493-498). However, in 1997, from MALDI Mass spectrometry analysis of a human IL-7 produced by recombinant technology and from site directed mutagenesis exchanging serine for cysteine, Cosenza and colleagues established the assignment of the three disulfide bridges to the positions 1-6; 2-5; 3-4, in a way fully analogous to the intra-molecular disulfide bridges experimentally determined for IL-4 (Cosenza L. et al.; Protein Science; 2000; 9:916-926—Walter M. R. et al.; Journal of Biological Chemistry; 1992; 267:20371-20376). In this work, the mass spectrometry analysis of the peptide digest of the recombinant native molecule clearly demonstrated the reality of the Cys2-Cys141 (1-6) disulfide bridge and the site directed mutagenesis established the critical role for bioactivity of the Cys2-Cys141 (1-6) and Cys47-Cys92 (3-4) bridges. The two Cys/Ser IL-7 mutants allowing these two single bridges were able to show a good bioactivity (EC50 of 4×10−9 and 2×10−9 M) in the bioassay in comparison to EC50 of 2×10−10 for the three disulfide bridges molecule 1-6; 2-5; 3-4. Based on these experimental results, these three disulfide bridges 1-6; 2-5; 3-4 were assigned to the human Interleukin-7 and filed into the international protein data bank (Swiss Prot P13232, PDB code 1IL7).

The present invention now shows that the above three-dimensional structure, presented, demonstrated and accepted in the data bank until now, is incorrect and that the long term activity of recombinant human IL-7 is mostly expressed by a specific 1-4; 2-5; 3-6 conformer. The experimental results obtained differ from the previously reported disulfide bonds in human IL-7 (hIL-7) (Cosenza L. et al.; Journal of Biological Chemistry; 1997; 272:32995-33000) and show, for the first time, that long term active IL-7 compositions require the presence of a substantially pure particular IL-7 conformer which is in accordance with other models designed by homology modeling with GM-CSF and IL-4 conformations.

Within the context of the present invention, an "IL-7 polypeptide" designates a mammalian (e.g., human or simian) IL-7 polypeptide and, more preferably, a human IL-7 polypeptide, especially for uses as therapeutic or vaccine, or a simian IL-7 polypeptide, especially for use in non human primate experiments. Preferred IL-7 polypeptides of this invention comprise an amino acid sequence as described in EP 314 415 as well as any natural variants and homologs thereof. The sequence of human IL-7 is available on genebanks. The typical wild-type protein comprises 152 amino acids and, optionally, an additional N-terminal methionine residue (SEQ ID Nos: 2, 4, 17 and 19). Variants thereof include, more preferably, natural allelic variants resulting from natural polymorphism, including SNPs, splicing variants, etc. In a specific embodiment, the term IL-7 polypeptide is meant to designate a polypeptide having the sequence of SEQ ID NO: 2, 13 [SEQ ID NO: 13 comprising or not the signal peptide (amino acids no: 2-25)], 17, 19, 21 or 23, as well as natural variants thereof. The specific IL-7 polypeptide used in the present invention is preferably a recombinant IL-7, more preferably a recombinant human IL-7 conformer comprising the amino acid sequence SEQ ID NO: 2, 4, 17 or 19.

A specific "conformer" of IL-7 designates an IL-7 polypeptide having a particular three-dimensional configuration.

The term "recombinant", as used herein, means that the polypeptide is obtained or derived from a recombinant expression system, i.e., from a culture of host cells (e.g., microbial or mammalian) engineered to contain a nucleic acid molecule encoding an IL-7 polypeptide. "Microbial" refers to recombinant proteins made in bacterial expression systems.

For medical use (including therapeutic, prophylactic, etc), the IL-7 conformer is preferably a recombinant human IL-7 conformer. In this regard, in a particular embodiment, the specific IL-7 conformer has the amino acid sequence of SEQ ID NO:4, 17 or 19 and comprises the disulfide bridges Cys2-Cys92; Cys34-Cys129 and Cys47-Cys141. In an other specific embodiment, the specific IL-7 conformer has the amino acid sequence of SEQ ID NO:4, 17 or 19 and comprises an additional Methionine at the N-terminal position (i.e., SEQ ID NO:2).

For further uses, including experimental uses, the IL-7 conformer may be a recombinant simian IL-7 conformer. The recombinant simian IL-7 conformer preferably comprises amino acid sequence SEQ ID NO: 13 [SEQ ID NO: 13 comprising or not the signal peptide (amino acids no: 2-25)], SEQ ID NO: 21 or 23.

The IL-7 conformer of this invention may be glycosylated or unglycosylated. Many secreted proteins acquire covalently attached carbohydrate units posttranslationally. Glycosylation is frequently in the form of oligosaccharide units linked to proteins through an asparagine residue (situated in the consensus sequence: -Asn-X-Ser/Thr- where X is any amino acid except proline) or through serine/threonine amino acid side chains, giving N-glycosidic or O-glycosidic bonds, respectively. Both the structure and number of oligosaccharide units attached to a particular secreted protein can be highly variable, resulting in a wide range of apparent molecular weights attributable to a single glycoprotein.

Murine IL-7 (mIL-7), simian IL-7 (sIL-7) and human IL-7 (hIL-7) are secreted glycoproteins and, in a first variant, the IL-7 conformer of this invention is glycosylated. The conformer may comprise various types of oligosaccharide units, depending on the production system and conditions. These may be, for instance, N-acetyl glucosamine, N-acetyl galactosamine, mannose, galactose, glucose, fucose, xylose, glucuronic acid, iduronic acid and/or sialic acids.

In a particular embodiment, the IL-7 conformer of this invention is moderately glycosylated. Preferably, the glycosylation is of the CHO type, even more preferably, produced by a CHO glycosylation mutant that stably expresses α2,6 sialyltransferase and presents a deficiency in CMP-Neu5Ac Hydrolase activity. Such glycosylation typically includes N-acetyl glucosamine, N-acetyl galactosamine, mannose, galactose, glucose, fucose, xylose, glucuronic acid, iduronic acid and/or sialic acids.

In an other, preferred, embodiment, the IL-7 conformer comprises a human type glycosylation. To produce such glycosylated form, the IL-7 conformer is typically produced by recombinant technology in a human host cell, which may be selected from human stromal or epithelial cell lines, HEK-293 (Human Embryonic Kidney), HER (Human Embryonic Retina), HEK (Human Epidermal Keratinocytes), human thymus or human cortical epithelial cell lines, human bone marrow or human bone marrow stromal cell lines.

In an other, variant, the IL-7 conformer is not glycosylated.

A recombinant human IL-7 conformer having human carbohydrate pattern is highly preferred for therapeutic use.

In a specific embodiment, the invention relates to a specific IL-7 conformer, wherein said IL-7 conformer has the amino acid sequence of SEQ ID NO:4, 17 or 19, comprises the disulfide bridges Cys2-Cys92; Cys34-Cys129 and Cys47-Cys141, and is human glycosylated, moderately glycosylated or unglycosylated, more preferably (human type-)glycosylated. In an other embodiment, the sequence of the conformer comprises an additional methionine residue at the N-terminal end (SEQ ID NO:2) and is glycosylated or unglycosylated.

The purified conformer may be in the form of a monomer, or associated or complexed with a particular compound of choice. In this regard, in a particular embodiment, the IL-7 conformer is associated to the hepatocyte growth factor ("HGF"), as a heterodimer. The heterodimer may be obtained chemically, by complexation or by recombinant technology (i.e., by genetic fusion).

In an other particular embodiment, the IL-7 conformer is functionally attached to a Fc portion of an IgG heavy chain, typically through a peptide hinge region. Such fusion molecules have potentially increased stability and half-life in vivo. The IgG moiety is most preferably a human IgG1 or IgG4.

In an other particular embodiment, the IL-7 conformer is functionally associated to a human serum albumin ("HSA") or a portion of a HSA, as a fusion protein. Such fusion molecules have potentially increased stability and prolonged half-life in vivo.

Drug Substance and Pharmaceutical Compositions

The invention also relates to a drug substance comprising, as the desired product, an IL-7 conformer as described above, said drug substance being substantially free of IL-7 product-related substances and product related impurities.

A preferred drug substance is further substantially free of process related impurities.

Within the context of the present application, the term "drug substance" refers to a product suitable for use as the active principle of a medicament. The "drug substance" according to this invention is, by nature, a complex product, i.e., as a result of its production method (e.g., recombinant DNA technology).

The present invention now discloses that, in order to produce efficient therapeutic and vaccine enhancement effects, an IL-7 drug substance or pharmaceutical composition should contain, as the major molecular species, the conformer refolded according to the 1-4; 2-5; 3-6 disulfide bridges. Although other bioactive conformers, r-hIL-7 molecular variants, such as 1-6; 2-5; 3-4 do exist and have been described in the literature for long term use and/or repeated administrations, the results obtained by the inventors now demonstrate, for the first time, that these products will behave as product related impurities, presenting new epitopes and susceptible to induce a neutralizing immune response toward the preferred conformation of IL-7.

The present invention also discloses the fact that, in the specific case of a recombinant IL-7-containing pharmaceutical compositions, other potential product-related substances and product-related impurities, which would normally be included in the specification of the drug substance and/or drug product, although bioactive, behave like new epitopes because of the potent vaccine enhancing property of IL-7. These products should thus be strictly minimized because they are able to trigger an immune reaction against the desired IL-7 molecule.

Bioactivity in a specific bioassay is a key critical result to qualify the activity of a recombinant protein for therapeutic use (see ICH Q6B, Harmonized Tripartite Guideline which concerns specifications, test procedures and acceptance criteria for biotechnological drug substances and products. Published in the Federal Register in Aug. 18, 1999; issued as 64FR page 44928 (FDA) and adopted in Europe by the Committee for Proprietary Medicinal Products in March 1999; issued as CPMP/ICH/365/96). Bioactivity is in fact the only single test of activity usually retained as a specification of activity for production batch release. Compliance with bioactivity specifications usually warrants that the recombinant protein drug substance/drug product is active in humans. Although various other in vivo animal models are implemented to test the activity of recombinant proteins, since the heterologous human recombinant proteins differ from the homologous protein in the tested animal species, the evaluation of long term activity in animals is hampered.

The previous experience of long term use of recombinant proteins in humans shows that the administration of an unmodified protein sequence, devoid of highly immunoreactive "process related" contaminants such as DNA, endotoxins and host cell proteins, allows a long term activity and benefit without neutralizing immune reactions. Product related substances, which are molecular variants of the desired product (as defined in ICH Q6B guideline), and product related impurities, as long as they have a significant bioactivity, are tolerated at a relatively high percentage of the drug substance/drug product composition. ICH international guideline Q6B stipulates that "product related substances are molecular variants of the desired product formed during manufacture and/or storage, which are active and have no deleterious effect on the safety and efficacy of the drug product. These variants possess properties comparable to the desired product and are not considered impurities". In that light, various product related substances and/or product related impurities, molecular variants of IL-7, if bioactive, would authorize a batch release based on the bioassay. The present invention now discloses that, in contradiction with these guidelines and common practice, in the specific case of IL-7, these molecular variants, whatever their bioactivity, would induce an immune response against the r-hIL-7 desired product and/or endogenous human IL-7 and neutralize the long term therapeutic benefit of the recombinant protein. This is mainly due to the association of these molecular variants, behaving like new epitopes, with the potent vaccine enhancing capacity of IL-7. Among these molecular variants, the present invention now discloses that a specific attention should be paid to conformers resulting from an inappropriate refolding of the molecule, to deamidated forms, to dimers and to hyperglycosylated forms, for example, and more generally to molecular bioactive variants susceptible to induce an immune reaction because they differ from the preferred, specifically identified, molecular species.

In particular, by conducting in vivo experiments in monkey (as reported in the examples), the inventors have been able to demonstrate that efficient drug substances would require, as a major constituent, an IL-7 conformer as described above, and should also be substantially free of other conformers or product-related impurities. Such results would not have been achieved in in vitro bioassay, where all compounds are bioactive, or in in vivo assays in rodents, where IL-7 has a very strong lymphopoietic effect on B cells. By cloning the simian IL-7 and conducting in vivo experiments in monkeys using either drug substances of this invention or complex products as disclosed in the prior art, the inventors have unexpectedly demonstrated that a specific conformer was active and needed to be used in purified form.

A particular object of this invention thus resides in a drug substance comprising, as the desired product, an IL-7 conformer as described above, said drug substance being substantially free of IL-7 product-related substances and product related impurities.

The term "substantially free", as used herein, indicates that the drug substance contains no significant or adverse amount of product-related substances, product related impurities and process-related impurities. More specifically, the drug substance should contain less than 5%, more preferably less than 3%, even more preferably less than 2% of product-related substances, product related impurities and process-related impurities. Most preferred drug substances contain less than about 1% of product-related substances and/or product related impurities and only trace amount of process-related impurities.

IL-7 product-related substances designate IL-7 molecular variants, which include, for example, other IL-7 conformer and/or any active or inactive peptide or polypeptide fragments of IL-7.

IL-7-related impurities include, for example, human IL-7 polypeptides comprising mono or bi-disulfide bridges, contiguous disulfide bridges and any disulfide bridges combination such as the following: Cys: 1-6; 2-5; 3-4, and adjacent disulfide bridges: Cys: 1-2; 3-4; 5-6. Other IL-7 related impurities include aberrant glycosylated form including hyperglycosylated IL-7, yeast-glycosylated IL-7, truncated IL-7, deamidated recombinant IL-7, dimeric or multimeric protein comprising IL-7, oxidized methionine form or a combination thereof.

Whatever their biological activity, these IL-7 molecular variants and IL-7-related impurities should be strictly minimized or discarded.

Process related impurities include DNA, endotoxins, cell debris, etc.

Such impurities as mentioned above are often generated by recombinant DNA processes. However, their impact on the final product activity has not always been assessed and efficient methods for their removal are not always available. The present invention now demonstrates that conventional recombinant methods of producing IL-7 also generate various impurities as described above. The invention more particularly demonstrates that various IL-7 molecular variants are present and that various amino acid sequences are present. Furthermore, the inventors have discovered that the most powerful mid or long term in vivo biological activity of r-IL-7 is carried by a specific conformer having three particular disulfide bridges: Cys: 1-4 (Cys2-Cys92); 2-5 (Cys34-Cys129); 3-6 (Cys47-Cys141). Missing or improper disulfide bridges could very significantly decrease IL-7 activity. Furthermore, the presence of such impurities produces molecules which are immunoreactive upon administration to human or non-human primates, and thus impair the therapeutic benefit of the IL-7 conformer of the present invention.

A preferred drug substance is thus a drug substance wherein the total amount by weight of IL-7 comprises at least 95% by weight, preferably at least 98% by weight, more preferably at least 99.5% by weight of an IL-7 conformer according to the invention.

The invention also relates to a pharmaceutical composition comprising an effective amount of a drug substance as described above and one or more pharmaceutically compatible or acceptable carriers, excipients or diluents.

The invention shows that pharmaceutical compositions comprising a substantially pure IL-7 conformer as described above clearly increase the vaccine properties of IL-7 and its capacity to stimulate antigen-specific immune responses. The invention thus demonstrates that highly efficient biological preparations are obtained when IL-7 related impurities are removed and a specific conformer as described above is used.

The pharmaceutically compatible or physiologically acceptable carrier, excipient or diluent may be selected from neutral to slightly acidic, isotonic, buffered saline, solutions or suspensions and more preferably from sucrose, trehalose, and amino acid. The pharmaceutically compatible carrier is preferably contained in an appropriate buffer to form an isotonic solution. Numerous molecular variants of IL-7 such as hyperglycosylated recombinant proteins produced from recombined yeast strains, IL-7 dimers produced at low ionic strength, and deamidated forms, although bioactive should be strictly minimized. During manufacture and storage, exposition of the molecule to high or moderately high pHs: 8 to 10 triggers the formation of deamidated forms. Storage at pH 8.5 to 9 for a few days at room temperature induces appearance of these deamidated molecular species. Steps including high pHs are preferably minimized during the process and stability of the recombined protein is improved if stored in a slightly acidic buffer pHs 5 to 7. The appropriate buffer has preferably a pH range comprised between 5 to 7.5, preferably 6 to 7, even more preferably of about 6.5 and is preferably an organic salt selected from a sodium citrate buffer or an ammonium acetate buffer. The pharmaceutical composition may be in the form of a suspension, solution, gel, powder, solid, etc. The composition is preferably a lyophilized form. Indeed, product can be formulated as a lyophilisate using appropriate excipient solutions (e.g., sucrose and/or trehalose in a range of 1/1 to 10/1, preferably 2/1 to 6/1 sugar/drug substance mass ratio for example) as diluents and lyo-protectors.

The composition may comprise stabilizing agents, such as sugar, amino acids, proteins, surfactants, etc. The composition may comprise any saline solution, including phosphates, chloride, etc. Appropriate dosages can be determined in trials.

A particular pharmaceutical composition according to the invention comprises, in addition to the active drug substance, a protein and/or a surfactant. These presence of a protein, or any other high molecular weight molecule of natural origin, reduces exposition of IL-7 to the host immune system and therefore avoids secondary effects. More preferably, the protein is non immunogenic in the subject, such as any protein of human origin. A most preferred example of protein is human serum albumin. The surfactant may be selected from known surfactants such as Tween products, preferably Tween 80. A specific composition of this invention comprises human serum albumin (preferably 2 to 5 mg/ml) or Tween 80 (typically 0.005%) or any other substance such as a tensioactive substance, capable of preventing IL-7 immunogenicity due to local persistence of the drug product after administration of the composition.

Actual dosage levels of active ingredients in the compositions of the present invention may be adapted so as to obtain an amount of active ingredient that is effective to obtain a desired therapeutic response for a particular composition and method of administration. The selected dosage level therefore depends upon the desired therapeutic effect, the route of administration, the desired duration of treatment and other factors. Generally, dosages of 3 to 300 µg/kg, preferably, 10 to 100 µg/kg, administered by subcutaneous route, can be expected to induce a biological effect preferably while administered from once daily down to once weekly, possibly twice weekly, preferably not more frequently than once every 48 h.

It should be understood, however, that the specific dose level for any particular patient will depend upon a variety of factors including the body weight, general health, sex, diet, time and route of administration, rates of absorption and excretion, combination with other drugs and the severity of the particular disease being treated. In the specific case of IL-7 a particular attention should be paid to the immune status of the patient before adjusting dose level. The more the patient is immuno-depressed, as judged for instance through peripheral CD4 T-Cell counts, the less the dose necessary to induce a relative increase in lymphocyte counts. In severely immuno-depressed primates, sub-cutaneous doses of 60 µg/kg daily produce a strong increase in T-Cell counts (×3 to ×5, in a dose-dependent manner), but in primates with normal lymphocyte counts, higher doses such as 300 µg/kg are necessary to increase lymphocyte counts from 2 to 5-fold. After sub-cutaneous administration, recombinant IL-7 has a surprisingly long blood half life in primates. Its effect on cell cycling lasts for 24 to 48 hours, allowing efficient treatment schedules with single injection daily down to one injection weekly.

Pharmaceutical compositions according to the invention are preferably administered from once daily down to once weekly, possibly twice weekly, preferably not more frequently than once every 48 h, only in order to obtain and/or stimulate patents immune regeneration.

Preferred administration routes are parenteral routes. The parenteral route is preferably an intra-tumoral, more preferably an intravenous or a sub-cutaneous administration. It includes also intra-arterial, intra-peritoneal or intra-muscular injections. It should be understood, however, that any other suitable administration route may be contemplated depending upon the health status and the reactivity of the patient.

The pharmaceutical composition may comprise additional active ingredients, such as immuno-stimulating agents, preferably selected from a hematopoietic cell growth factor, a cytokine, an antigenic molecule (or antigen) and an adjuvant, for combined, separate or sequential use.

Such additional active ingredients may be formulated in combination with the IL-7, or, separately, for combined, separate or sequential use. In a first variant, the active ingredients are formulated together, in the same recipient or vessel. In an other, preferred variant, they are conditioned separately, i.e., in distinct vessels or recipients. According to this embodiment, the ingredients may be administered separately, e.g., simultaneously or sequentially (e.g., at different injection sites or at different time points), to produce the most efficient biological effect. Also, as mentioned above, repeated administrations of one or the two active ingredients may be performed.

In this respect, the invention relates to a pharmaceutical composition comprising a substantially pure IL-7 conformer as described above and an active ingredient selected from an immuno-stimulant and an antigenic molecule, for combined, separate or sequential use. Adjuvants are preferably formulated separately.

The hematopoietic cell growth factor is preferably selected from the Stem Cell Factor (SCF), particularly the soluble form of the SCF, G-CSF, GM-CSF, Flt-3 ligand, IL-15 and IL-2. Typical examples of cytokines for vaccine enhancement include cytokines that induce and/or stimulate a Th1-type immune response. The cytokine is preferably selected from γ interferon, IL-2, IL-12, RANTES, B7-1, MIP-2 and MIP-1α. It should be understood that other factors such as FGF7 or FGF10, interleukins and/or hormones may be used in combination with IL-7 to provide additional therapeutic benefit.

A specific composition of this invention comprises a substantially pure IL-7 conformer as described above and Stem Cell Factor, particularly the soluble form thereof, IL-15 and/or Flt-3 ligand and/or FGF10.

An other specific composition of this invention comprises a substantially pure IL-7 conformer as described above and a cytokine selected from γ interferon, IL-2, IL-12, RANTES and MIP-1α.

An other specific composition of this invention comprises a substantially pure IL-7 conformer as described above, a Stem Cell Factor and a cytokine.

As indicated above, the pharmaceutical composition may further comprise one or several antigens (or antigenic molecules), for combined, separate or sequential use. The antigen may be any synthetic or natural peptide, a recombinant protein, a killed, inactivated or attenuated pathogen product, a microorganism, a parasite, a lipid, etc., a portion thereof and a combination thereof. The antigen may be an entire protein, or any epitope-containing fragment or portion thereof, particularly peptides that are presented to the immune system through MHC class I or MHC class II molecules. The antigen can be any viral antigen, bacterial antigen, parasite antigen, tumor antigen, etc. Specific examples of antigens include antigens derived from HIV, Varicella Zoster virus, Influenza virus, Epstein Barr virus, type 1 or 2 Herpes Simplex virus, human cytomegalovirus, Dengue virus, Hepatite A, B, C or E virus, Syncytium respiratory virus, human papilloma virus, *mycobacterium tuberculosis, Toxoplasma* and *Chlamydia*.

A particular object of this invention relates to a composition comprising a substantially pure IL-7 conformer as described above and an antigenic molecule, for combined, separate or sequential use. The composition may further comprise one or several immuno-stimulating agents as disclosed above, for combined, separate or sequential use.

A further particular object of the present invention concerns a pharmaceutical composition comprising an IL-7 conformer as described above, wherein said pharmaceutical composition is administered simultaneously, a few days before or sequentially with one or several antigenic molecules in order to obtain and/or stimulate an antigen-specific immune response in a subject.

A further particular object of the present invention concerns a method of causing or enhancing an antigen-specific immune response in a subject, comprising administering to a subject said antigen (or an epitope-containing fragment thereof) and a pharmaceutical composition comprising an IL-7 conformer as described above. The pharmaceutical composition may be administered simultaneously, a few days before or sequentially with said antigen in order to obtain and/or stimulate an antigen-specific immune response in a subject.

In another preferred embodiment, the composition of the invention further comprises an adjuvant. The adjuvant may be selected from any substance, mixture, solute or composition facilitating or increasing the immunogenicity of an antigen and able to induce a Th1-type immune response, such as CpG, QS21, ISCOM and monophosphoryl lipid A. Such adjuvants are particularly suited to produce and/or amplify a specific immune response against antigen(s) in mammalian subjects, particularly in humans. The adjuvant is preferably conditioned and administered separately from the IL-7 containing composition and/or at a distinct site of injection, preferably with the desired antigen(s).

The present invention also concerns a pharmaceutical composition comprising an effective amount of a human IL-7 conformer according to the invention in admixture with a suitable diluent, excipient or carrier, for parenteral administration to a human patient for prophylactic or therapeutic stimulation of B or T lymphocyte development and proliferation, or for augmentation of an immune response. The pharmaceutical compositions of the invention induce a prolonged lymphopoiesis stimulation and/or amplified immune responses.

A pharmaceutical composition according to the invention may also be used in a human patient for prophylactic or therapeutic stimulation of B or T lymphocyte development and proliferation, for enhancement of global and/or specific immuno-reconstitution, or for enhancement of humoral and/or cellular immune responses.

A particular pharmaceutical composition according to the invention is for use to prevent or reduce opportunistic infections in immunodeficient patients.

Another particular pharmaceutical composition according to the invention is for use to prolong lymphopoiesis stimulation and/or to produce specific immune response not only against dominant epitopes but also against sub-dominant or less immunogenic epitopes, epitopes having a lower affinity for the T cell receptor, which will allow to broaden the repertoire of a specific immune response in human patients.

The invention is particularly suited to produce a preventive or curative immune response in subjects, such as immunodeficient patients, cancer patients, patients undergoing grafts, patients infected with a virus or a parasite, elderly patients or any patients having low CD4 count etc.

Production Methods and Tools

An other aspect of the present invention is to provide appropriate constructs and methods for producing the above compositions, particularly the above IL-7 conformer and drug substances, in sufficient quantities and quality for pharmaceutical use thereof.

In this regard, the invention now discloses nucleic acid molecules comprising a sequence encoding an IL-7 polypeptide, said sequence being optimized for the expression, in a recombinant host, of biologically active IL-7, particularly of an IL-7 conformer as described above. More specifically, the nucleic acid molecules provide for a limited expression of truncated IL-7 polypeptides and increase the yields of production of biologically active human IL-7 conformer.

The human and simian IL-7-encoding DNA sequence (genomic or cDNA) contain, at position 49 after the "ATG" initiation codon, a second putative "ATG" which could behave as a second initiation codon in E. Coli. Indeed, this second "ATG" is preceded by a "pseudo Shine-Dalgarno" sequence (ribosome binding sequence). In order to create optimized products, the applicants have undertaken to inactivate this putative second initiation codon, thereby significantly reducing the potential production of an amino-terminal truncated form of r-hIL-7. To produce such optimized sequences, nucleotides in the coding sequence were mutated in order to inactivate the "SD-like" sequence, without modifying the resulting, encoded, r-IL-7 amino acid sequence.

A further object of the invention thus relates to nucleic acid molecules encoding a human IL-7 polypeptide, wherein said nucleic acid contains a modified sequence avoiding the production of an amino-terminal truncated polypeptide, more specifically by inactivation of the "SD-like" sequence (i.e., of the putative second initiation codon located at position 49 in the sequence, which encodes methionine residue 18 in SEQ ID NO: 2).

Inactivation of the putative second initiation codon may be achieved, more preferably, by modifying the sequence in at least one of the 5 codons preceding the ATG codon encoding methionine 18 in SEQ ID NO: 1, i.e., in codons 13-17 encoding amino acid sequence TyrGluSerValLeu. In a specific embodiment, the sequence is modified by altering the codon coding for a serine at position 15 in SEQ ID NO: 1 or 2. More specifically, in a preferred sequence, this codon is modified so as not to contain an AG doublet. Suitable codons may be selected, for instance, from TCC, TCT, TCA and TCG. In SEQ ID Nos: 1, 3, 16 and 18, the TCC codon has been used. The codon encoding Tyr at position 13 (based on the numbering in SEQ ID NO:1) may be selected from TAC or TAT. The codon encoding Glu at position 14 (based on the numbering in SEQ ID NO:1) may be selected from GAG and GM. The codon encoding Val at position 16 (based on the numbering in SEQ ID NO:1) may be selected from GTT, GTC, GTA and GTG. Finally, the codon encoding Leu at position 17 (based on the numbering in SEQ ID NO:1) may be selected from CTG, CTA, CTT, CTC, TTA and TTG. All combinations of the above indicated codons are possible. A specific example of an altered DS-like sequence corresponds to nucleotides 37-51 of SEQ ID NO:1.

A specific, preferred nucleic acid molecule of this invention comprises the sequence of SEQ ID NO:1 and codes for a recombinant human IL-7 polypeptide.

Another specific, preferred embodiment of the invention relates to a nucleic acid molecule as described above which further comprises a signal sequence causing secretion of the produced polypeptide. The signal sequence may be selected from the natural signal sequence of the human IL-7 protein, or from any heterologous signal sequence. Such sequences may originate from other secreted proteins, such as the human growth hormone, or be artificial or synthetic. A preferred signal peptide may be a natural signal peptide of a human growth factor or of a human growth hormone and, more preferably, a natural signal peptide of the human erythropoietin. An even more preferred signal peptide is a synthetic signal peptide such as HMM38. Preferred sequences are those functional in competent mammalian host cells. A specific example of such an improved sequence comprises SEQ ID NO:3, 16 or 18. This sequence comprises a leader sequence and an inactivated SD-like sequence, for improved expression.

Another object of the invention concerns a polypeptide encoded by a nucleic acid sequence as described above, which may be glycosylated or unglycosylated.

A preferred object of the invention concerns a polypeptide, as described above, wherein the tertiary structure of said polypeptide comprises the following three disulfide bridges: Cys: 1-4; 2-5; 3-6.

The present invention further provides vectors comprising a nucleic acid as described above, as well as recombinant host cells comprising said nucleic acid or said vectors. The nucleic acids and vectors may be used to produce recombinant human IL-7 polypeptides in various competent host cells, as well as for gene therapy purposes.

The vector may be a plasmid, virus, phage, cosmid, episome, etc. Preferred vectors are viral vectors (e.g., recombinant adenoviruses) and plasmids, which can be produced based on commercially available backbones, such as pBR, pcDNA, pUC, pET, pVITRO, etc. The vector typically comprises regulatory elements or sequences to control or mediate expression of an IL-7 polypeptide from the optimized coding nucleic acid. The regulatory sequences may be chosen from promoters, enhancers, silencers, tissue-specific signals, peptide signals, introns, terminators, polyA sequences, GC regions, etc., or a combination thereof. Such regulatory elements or sequences may be derived from mammalian, plant, bacterial, yeast, bacteriophage or viral genes, or from artificial sources. Useful promoters for prokaryote expression (such as *E. coli*) include T7 RNA polymerase promoter (pT7), TAC promoter (pTAC), Trp promoter, Lac promoter, Tre promoter, PhoA promoter for example. Suitable promoters for expression in mammalian cells include viral promoters (e.g., CMV, LTR, RSV, SV40, TK, pCAG, etc.), domestic gene promoters (e.g., E1fα, chicken βactine, Ubiquitine, INSM1, etc.), hybrid promoters (e.g., actine/globin, etc.), etc. A vector may comprise more than one promoter. The promoters may be inducible or regulated. For instance, the use of inducible or regulated promoters allows a better control of production by dissociating the culture from production phases. Inducible or regulated promoters may be found in the literature, such as the Tetracycline system, the Geneswitch system, the Ecdysone system, the Oestradiol system, the RU486 system, the Cumate system, the methallothioneine promoter etc. Other systems are based on electric currents or microwaves, such as Ultra sons focalises and the like. These systems can be used to control expression of an IL-7 polypeptide according to the invention.

The IL-7 may be co-expressed with an anti-apoptotic factor (e.g., iex, Bcl2, BclXL, etc.). The cDNA (coding for said IL-7 and for said anti-apoptotic factor) may be both placed downstream of the same promoter, but separated by an IRES sequence, or each of them downstream of its own promoter.

The vector may further comprise an origin of replication and/or a marker gene, which may be selected from conventional sequences.

The vector may further comprise various combinations of these different elements which may be organized in different ways.

The present invention thus also provides recombinant host cells comprising a nucleic acid or a vector as described above. The host cell may be selected from any eukaryotic and prokaryotic cells, typically from a mammalian cell (in particular a human, rodent, canine cell), a bacterial cell (in particular *E. coli, Bacillus Brevis, Bacillus Subtilis*), a yeast cell, a plant cell and an insect cell. Where yeast, plant or insect cells are used for production purposes, the products obtained in said cells are preferably submitted to a treatment step in order to produce unglycosylated products. These host cells may be adapted to serum-free media. Production may also be accomplished in a transgenic animal.

Preferred recombinant host cells are selected from a mammalian cell, in particular a human cell, and a bacterial cell, as well as derivatives or mutants thereof. Specific examples of suitable host cells include bacteria, which provide for non-glycosylated production of proteins. In Bacteria (e.g., *Escherichia coli*), recombinant IL-7 is generally expressed as inclusion bodies. This host is particularly advantageous and may be used, more specifically, with a vector comprising a sequence SEQ ID NO:1.

Other examples of suitable host cells include mammalian cells, which provide for glycosylated production of proteins. One may cite Chinese Hamster Ovary (CHO) cells, Baby Hamster Kidney (BHK) cells, Human Embryonic Kidney (HEK-293) cells, human epidermal keratinocytes (HEK), human stromal or epithelial cells, PERC6, etc. In such mammalian cells, IL-7 may be produced as a secreted protein using functional signal peptide sequences. These hosts may be used, more specifically, with a vector comprising a sequence SEQ ID NO:3, 16 or 18.

A specific object of this invention is a prokaryotic host cell comprising a nucleic acid molecule comprising SEQ ID NO: 1.

Another specific object of this invention is a eukaryotic host cell comprising a nucleic acid molecule comprising SEQ ID NO: 3, 12, 16, 18, 20 or 22.

Another specific object of this invention is a eukaryotic or prokaryotic host cell comprising a nucleic acid molecule encoding an IL-7 polypeptide comprising amino acids 26-152 of SEQ ID NO: 13.

A further object of the present invention relates to antibodies immunoreactive with an IL-7 conformer as described above. Such antibodies may be produced according to conventional methods, including immunization of animals and collecting the serum (polyclonal) or preparing hybridomas from spleen cells (monoclonal). Fragments (e.g., Fab') or derivatives of antibodies (e.g., ScFv) may be produced by known biological and chemical methods. Preferred antibodies are specifically immunoreactive with an IL-7 conformer as described above, i.e., can bind the IL-7 conformer without substantially binding IL-7 polypeptides which do not comprise the following three di-sulfide bridges: Cys2-Cys92, Cys34-Cys129 and Cys47-Cys141. Although non-specific or less effective binding to such other antigens may be observed, such non-specific binding can be distinguished from specific binding to the particular conformer of this invention.

The antibody is preferably of simian, murine or human origin or has been humanized.

The invention also relates to a hybridoma cell line that produces a monoclonal antibody as described above.

Such antibodies are useful in detecting IL-7 conformer or in neutralizing IL-7 biological activity in assays or experiments involving multiple lymphokines. A composition suitable for diagnosis, assay or therapy comprising such monoclonal antibodies is also an object of the present invention.

The invention also provides a method of producing or amplifying an optimized IL-7 nucleic acid from a sample, the method comprising:

i) providing a sample containing an IL-7 gene or coding sequence, ii) contacting said sample with a pair of primers that produce an optimized sequence, particularly a sequence devoid of a functional second initiation codon at position 49, and iii) producing or amplifying the optimized IL-7 nucleic acid.

The sample may comprise genomic DNA, cDNA or RNA.

Amplification of the gene may be produced by any technique known per se, such as PCR, RT-PCR, or other amplification techniques. Amplification usually requires the use of a pair of primers characterized in that the forward sequence hybridizes with the 5' end of the DNA and in that the reverse sequence hybridizes with the 3' end of the same DNA. Specific examples of primers are as follows:

Pair 1: SEQ ID NO: 5 and SEQ ID NO: 6,
Pair 2: SEQ ID NO: 7 and SEQ ID NO:6, and
Pair 3: SEQ ID NO: 8 and SEQ ID NO: 6

Such particular nucleic acid primers represent further objects of this invention (e.g., SEQ ID NO:5-8).

It should be understood that other primers can be designed by the skilled artisan, such as fragment of the optimized IL-7 gene, for use in the amplification step and especially a pair of primers comprising a forward sequence and a reverse sequence, wherein said primers of said pair hybridize with a region of the mutated IL-7 gene and allow amplification of at least a portion of the IL-7 gene.

Another object of the present invention relates to processes which can be used, on an industrial scale, for the production of a pharmaceutical grade, substantially pure IL-7 conformer as described above. The process leads to high yields of recombinant IL-7 conformer suitable for therapeutic use. The invention also provides novel methods of controlling IL-7-containing compositions, to determine the presence of amount of an IL-7 conformer as described above.

In a particular aspect, the method of producing an IL-7 conformer or a drug substance as defined above comprises:
a) providing a sample comprising IL-7 polypeptides, and
b) purifying an IL-7 conformer as described above.

The sample used in step a) may be any biological sample containing an IL-7 polypeptide. This includes, for instance, a cell supernatant, a biological fluid, a cell extract, a tissue sample, etc. Preferred samples are cell supernatants of recombinant host cells that produce a recombinant IL-7 polypeptide, more preferably a recombinant human or simian IL-7 polypeptide, even more preferably, a recombinant human IL-7 polypeptide.

Most preferred samples are (obtained from) cell supernatants of recombinant host cells that contain an optimized IL-7 coding nucleic acid molecule as described above, more particularly a polynucleotide comprising SEQ ID NO: 1, 3, 12, 16, 18, 20 or 22.

The sample may be subjected to various treatments or conditions in order to increase purity of IL-7, to release IL-7 from inclusion bodies, to remove cell debris or other particular bodies, etc. Typical examples of such treatments include centrifugation, filtration and/or clarification. The sample may thus be enriched for IL-7 polypeptide.

To increase the yields or efficiency of the method, it is highly desirable to produce a sample containing or enriched in correctly folded IL-7 polypeptides.

In this regard, where the sample is (or derives from) a culture of prokaryotic host cells encoding an IL-7 polypeptide, particular treatments of the sample are necessary. Such treatments include:
i) treating said sample to cause a complete denaturation of said IL-7 polypeptides,
ii) optionally purifying the denatured polypeptide obtained in step i) and
iii) refolding the polypeptides.

Step i) comprises the treatment of the sample to cause denaturation of IL-7 polypeptides. Denaturation designates a destruction and reduction of all tertiary structures in the polypeptide, such as disulfide bridges or other intra-molecular bounds. Denaturating treatment comprises the dissolution of inclusion bodies in a denaturant buffer to reach a fully denatured, solubilized protein. Denaturation may be obtained with a buffer comprising guanidine hydrochloride, or urea, EDTA, β mercaptoethanol or dithiotreitol (DTT). Appropriate dosages can be determined by persons skilled in the art and depend on the level of denaturation required. Other denaturing conditions, known in the art, may be applied as well, alone or in combination. A preferred level of denaturation corresponds to the destruction of all the disulfide bridges of IL-7. A preferred full denaturation protocol uses 8 M guanidine hydrochloride buffer. High guanidine hydrochloride molarity is preferred to allow full denaturation of the protein prior to its correct refolding. This stage of denaturation may be controlled by analytical techniques known in the art, such as electrophoresis, for instance.

Purification step ii) may be performed by different techniques known per se, but which have not been used so far in the present combination to produce a fully active IL-7 polypeptide conformer. These techniques are more preferably selected from hydrophobic interaction chromatography, ion exchange chromatography, affinity chromatography and gel filtration chromatography, either alone or in various combinations. Such methods allow to remove DNA and other impurities (lipids, etc.) which would lower recovery of the subsequent refolding step. In a preferred embodiment, step ii) comprises a hydrophobic interaction chromatography step. Such chromatography may be carried out using various supports and formats, preferably using HIC butyl, preferably in denaturing conditions. To perform this step, a preferred pH range is comprised between 6 and 9, preferably between 7 and 8.5 inclusive. Step ii) may be carried out on any support, preferably on batch or in column using an appropriate gel.

The refolding step iii) comprises a renaturation and preferably reoxydation of the IL-7 polypeptides and, typically, a further desalting step performed by filtration (for example a gel filtration) or ultrafiltration. In a preferred embodiment, the refolding comprises an ion exchange chromatography step to separate the active new conformer from the unwanted forms. In a most preferred embodiment, the refolding comprises a step of contacting the purified polypeptides with a selected affinity chromatography support in order to separate the active new conformer from the unwanted forms. This very advantageous step is selective for the elution of the correctly refolded IL-7.

In a particular embodiment of the invention, the refolding step iii) comprises passing the solution obtained in step ii) through a column comprising polymers of sulfated polysaccharides. The sulfated polysaccharide is preferably dextran sulfate or heparin and the matrices can be sepharose, acrylamide, agarose, dextran, cellulose or other types commonly employed in protein purification. A preferred matrix is heparin sepharose. The process may further comprise an additional step of eluting the desired IL-7 conformer.

In a particular embodiment, the above affinity column may be used both to purify and refold the polypeptides, i.e., to perform simultaneously steps ii) and iii).

Where the sample is (or derives from) a culture of eukaryotic host cells encoding IL-7 polypeptides, it may not be necessary to perform the above treatment steps i) to iii). Indeed, in such a situation, the sample may comprise correctly folded IL-7 proteins, although in complex admixture with other product-related substances and impurities. This is particularly true where the recombinant eukaryotic host cell comprises a nucleic acid molecule causing expression and secretion of the IL-7 polypeptides in the culture medium.

In this case, the sample may be directly subjected to the purification step b).

Purification step b) may comprise one or several purification steps such as filtration or ultrafiltration steps ion exchange chromatography, affinity chromatography, hydrophobic interaction chromatography etc., in order to eliminate drug related substances such as other conformers, deamidated forms, dimers of the protein, residual impurities, including DNA, endotoxins, etc. The chromatography step may be realized in a flow through mode, in a capture mode or in a streamline mode.

In a preferred embodiment, the purification step b) comprises loading the sample through a column packed with a specific gel comprising sulfated polysaccharides immobilized on a resin (dextran sulfate or heparin for example).

In another particular embodiment the purifying step comprises loading the sample through a column packed with a specific gel comprising a monoclonal anti IL-7 antibody immobilized on a resin (dextran sulfate or heparin for example).

These methods allow the reproducible and efficient production of a substantially pure fully active human IL-7 conformer as described above. The methods are particularly advantageous since the recombinant IL-7 conformer can be obtained with a purity of at least 95% by weight, preferably at least 98% by weight and even more preferably at least 99% or even 99.5% by weight with respect to the total amount of IL-7. Furthermore, the above purification method may be applied to polypeptides other than human IL-7, particularly to other cytokines having one or several disulfide bridges, including animal IL-7 (e.g., monkey IL-7), IL-13, IL-15, etc.

Each step of the above described process may be controlled by analytical methods, including SDS-PAGE analysis. The primary structure of the optimized IL-7 may be controlled and characterized by determining the gene and/or amino acid sequence, by peptide mapping analysis, after tryptic digestion, by determining molecular weight with SDS PAGE, size exclusion HPLC, MALDI TOF and/or Mass spectometry, by determining hydrophobicity with reverse phase HPLC for example, and/or by determining the electric charge with cation exchange chromatography HPLC or isoelectrofocalisation analysis for example.

In a specific variant, the invention relates to a method of producing an IL-7 conformer as defined above, the method comprising at least the following steps:
 a) providing a sample comprising IL-7 polypeptides produced by a recombinant prokaryotic host cell,
 a') treating said sample to cause a complete denaturation of said IL-7 polypeptides,
 a") optionally purifying the denatured polypeptide obtained in step a"),
 a'") refolding the polypeptides, and
 b) purifying the polypeptide to produce a conformer as described above.

In an other specific variant, the invention relates to a method of producing an IL-7 conformer as defined above, the method comprising at least the following steps:
a) providing a sample produced by a recombinant eukaryotic host cell, said sample comprising a refolded IL-7 polypeptide, and
b) implementing one or several purification steps in order to eliminate product related substances or impurities.

A further embodiment of the invention relates to IL-7 production methods as described above, wherein IL-7 expression by the recombinant host cells is inducible, regulated or transient, so that the cell culture and IL-7 expression phases can be dissociated. More particularly, in a particular embodiment, IL-7 expression can be repressed or minimized during recombinant cell growth, expansion and/or culturing, to allow the production of large amounts of recombinant host cells without any IL-7-mediated potential toxic effect. Then, IL-7 expression can be induced within the cell culture (or on a sample thereof), allowing the efficient synthesis and release of recombinant IL-7.

An object of this invention thus also resides in a method of producing a recombinant IL-7 polypeptide, comprising culturing a recombinant host cell comprising a nucleic acid molecule encoding said IL-7 polypeptide and recovering the recombinant IL-7 polypeptide produced, wherein said nucleic acid molecule provides for a regulated or inducible expression of said IL-7 polypeptide, so that expression of said IL-7 polypeptide can be repressed or minimized during recombinant cell growth and induced during production phase. The nucleic acid typically comprises an inducible promoter, which can be repressed or activated in the presence or absence of a specific agent contained or added into the culture media. The method is particularly suited to produce an IL-7 conformer as disclosed above.

Various regulated or inducible expression systems have been disclosed in the art, which are functional in mammalian host cells and can be used in the present invention. These include the Tetracycline TetOn/Off system, Geneswitch system (Invitrogen) with Mifepristone as inducible agent and GAL4-E1b promoter, Ecdysone system (induction with ponasterone A or muristerone A, analogs of insect steroid hormones) (Invitrogen), methallothioneine promoter (inducible by zinc), Oestradiol system, RU486 system, Ultra sons focalizes, Cumate system (Q-mate; Qbiogen), Cre-Lox system, etc. These regulated or inducible expression systems may be used in various cells, such as for instance HEK293, HEK293 EBNA, HEK, T-REX™-293, T-REX™-HeLa, T-REX™-CHO or T-REX™-Jurkat cell lines, transformed with a recombinant vector designed to express recombinant IL-7 after induction.

Alternatively, transient transfection can be used to dissociate cell expansion from IL-7 production. In this regard, efficient gene delivery vectors are used to introduce an IL-7 coding sequence into cells upon expansion thereof. More preferably, the vector system for transient transfection is a viral vector, such as a recombinant adenovirus or an episomal vector [e.g., pCEPH (Invitrogene), pTT (IRB: Durocher Y. et al. Nucl. Acids. Res., 2002, 30(2)) or using MAR sequences]. Adenoviruses (and other viral vectors such as AAVs, for instance), can be produced according to techniques known in the art. Typically, E1-defective adenoviruses are produced in a E1-complementing cell line, such as HEK293, PERC6 cells, etc. Such transient transfection process can be implemented in various mammalian cells in culture, such as A549, HeLa, VERO, BHK or CHO transformed cells for example (as disclosed in example A4). An alternative transient expression method suitable for use in the present invention is disclosed for instance in the next article: Durocher Y. et al. Nucl. Acids. Res., 2002, 30(2) in HEK293 EBNA or HEK293 cells.

In a preferred embodiment, the production methods of this invention comprise an additional step c) of characterizing and measuring or quantifying the particular IL-7 conformer as disclosed above contained in the resulting product. The physical and biological characterization of the desired IL-7 conformer may be obtained by Mass spectrometry (MALDI-TOF), infra-red spectroscopy, nuclear magnetic resonance (NMR), by determining circular dichroïsm, by assessment of the biological activity of the IL-7 conformer in a specific bioassay, by measuring the affinity toward a specific monoclonal antibody raised against said IL-7 conformer, or heparin affinity HPLC. Once characterized, the quantification of said conformer may be performed by ELISA, bioassay, affinity of said IL-7 conformer for IL-7 receptor and any method of protein quantification if applied to the isolated conformer.

In this regard, the invention also provides and concerns a method to identify and/or measure the quantity of IL-7 conformer and/or related impurities in a sample, particularly in a pharmaceutical preparation. Such characterization methods can be used to initially characterize and qualify the protein for filing a therapeutic use, in quality control of pharmaceutical batches. Indeed, the present invention now demonstrates that a fully biologically active IL-7 conformer exists and that the presence of impurities such as other conformers or IL7 peptide fragments may generate highly undesirable side effects. The invention thus proposes, for the first time, a method of characterizing and controlling IL-7-containing preparations, to determine the presence and/or relative quantity of the specific IL-7 conformer of this invention. Preferred methods use western blot, size-exclusion HPLC, Escherichia Coli Protein (ECP) assay, bacterial endotoxins assay, Limulus Ameobocyte Lysate test (LAL test), DNA quantification, SDS-PAGE, reverse phase HPLC, ion exchange HPLC, heparin Affinity HPLC, Bicinchoninic Acid Assay (BCA) method, Amino Acid Assay (AAA) method, ELISA, UV absorption and/or a Bioassay. These methods may be carried out alone or in various combinations.

The invention also provides a method of producing an IL-7 drug substance or pharmaceutical composition, said method comprising (i) culturing a recombinant host cell encoding an IL-7 polypeptide, (ii) isolating said recombinant polypeptide to produce an IL-7 drug substance and (iii) conditioning said IL-7 drug substance to produce a pharmaceutical composition suitable for therapeutic or vaccine use, said method further comprising a step of identifying, characterizing or measuring, in said drug substance or pharmaceutical composition, the quantity and/or quality of an IL-7 conformer as defined above and, more preferably, a step of selecting the drug substance or pharmaceutical composition which comprises, as the active ingredient, more than about 95, preferably 98% of said IL-7 conformer.

The characterizing step may be carried out by a variety of techniques, more preferably by mass spectrometry-related methods, with or without tryptic digest, circular dichroism, NMR, specific monoclonal antibody analysis for disulfide bridges and/or conformation characterization. The identification of molecular variants and product related impurities is preferably performed by using one or several methods selected from bi-dimensional electrophoresis, isoelectric focusing and ion-exchange chromatography for deamidated forms, size exclusion chromatography and SDS-PAGE analysis for dimeric or multimeric forms, and HPLC reverse phase with or without predigest for various forms including truncated forms and oxidized methionine forms.

The step is particularly suited for quality control of clinical or pharmaceutical compositions, whereby only compositions comprising more than about 95% of the above IL-7 conformer are retained, preferably more than about 96%, 98% or 99.5%.

Another object of the present invention relates to the use of the isolated IL-7 polypeptide conformer or of a recombinant IL-7 conformer obtained with the processes as described above, for the manufacture of a pharmaceutical composition to prevent or treat a disease associated with an immunodeficiency, particularly to induce a prolonged lymphopoiesis stimulation, to cause and/or amplify an immune response, particularly an antigen-specific immune response.

A further object of the invention relates to the use of an IL-7 conformer as a tool for experimental and pharmacological use in monkeys.

The invention also relates to kits for implementing the above methods comprising at least a primer specific for the optimized IL-7 gene and, optionally, a pair of primers and/or a probe and/or reagents for a nucleic acid amplification reaction and/or antibodies, as described above. Kits may alternatively comprise reagents to produce an IL-7 polypeptide as described above, such as an optimized nucleic acid, a vector, a recombinant host cell, and/or protocols or reagents for the purification or quality control of such preparations.

Other aspects and advantages of the present invention will be described in the following examples, which should be regarded as illustrative and not limiting the scope of the present application.

EXAMPLES

Example A

Construction and Expression of Optimized Human (h) and Simian (s) IL-7-Coding Nucleotide Sequences A1. E. Coli Expression (E. coli JM101):

1.1. Construction of Human IL-7-Coding Nucleotide Sequence:

The human IL-7 encoding cDNA sequence was amplified by polymerase chain reaction (PCR) (Mullis et al.; 1987; Methods in Enzymology; 155:335-350) from human placenta cDNA (BioChain Inc.) using the following specific oligonucleotide primers which contain restriction endonuclease recognition sequences:

```
IL75':                                    SEQ ID NO: 5
5'ATTCCATATGGATTGTGATATTAGAAGGTAAAGATGGC3'
        NdeI

IL73':                                    SEQ ID NO: 6
5'AGCCGGATCCTTATCAGTGTTCTTTAGTGCCCATCA3'
        BamHI
```

The human IL-7-encoding DNA sequence presents, at position 49 after the "ATG" initiation codon, a second putative "ATG" which could behave as a second initiation codon in E. Coli, since this second "ATG" is preceded by a "pseudo Shine-Dalgarno" sequence (ribosome binding sequence). To avoid the potential production of an amino-terminal truncated form of r-hIL-7, some of the nucleotides of the "SD-like" sequence were mutated (without modifying the resulting encoded r-hIL-7 amino acid sequence), thereby producing an improved methionyl-IL-7-coding-DNA sequence containing one or more preferred codon(s) for expression in E. Coli cells.

The suppression of the SD-like sequence in the IL-7-encoding DNA sequence was performed by site directed mutagenesis PCR, using the following oligonucleotide primers:

```
mutIL75':                                           SEQ ID NO: 7
5'TAGGGAATTCCATATGGATTGTGATATTGAAGGTAAAGATGGCAAACA
             NdeI
ATACGAGTCCGTTCTG3'

IL73':                                              SEQ ID NO: 6
5'AGCCGGATCCTTATCAGTGTTCTTTAGTGCCCATCA3'
        BamHI
```

The amplification and suppression of the SD-like sequence may be realized by single step using oligonucleotide primers above.

PCR products were assayed by polyacrylamide or Agarose gel electrophoresis in the presence of ethidium bromide and visualization by fluorescence of DNA bands stimulated by UV irradiation. A single major product band of the size corresponding to the IL-7 PCR fragment was isolated and inserted into the plasmid vector pCR II-TOPO (Invitrogen) using the TA-cloning method. The ligation products were transformed into TOP10 competent cells (Invitrogen). To select positive clones, plasmid DNA, prepared from cultured individual bacterial clones kanamycin resistant by Plasmid Miniprep Isolation techniques (Biorad), were analyzed by restriction mapping and confirmed by dideoxy Sequencing (Sanger et al.; 1977; Proceedings of the National Academy of Sciences of the USA; 74:5463-5467) of an asymmetric PCR product DNA using pCR II TOPO universal primers (Invitrogen) as sequencing primers.

To construct the final expression vector encoding the Met-human IL-7 polypeptide, plasmid DNA from a positive clone was digested with restriction endonucleases BamHI and NdeI and the resulting fragment, r-hIL-7 encoding DNA sequence, was inserted in between BamHI and NdeI restriction sites of a ptac vector.

This expression plasmid was constructed by replacing the T7 promoter by a tac promoter in a classical pET vector derived from pBR322. For this purpose, the tac promoter was first amplified using pMAL-p2X (Biolabs) as a matrix and oligonucleotides:

```
ptac1:                                    SEQ ID NO:9
5'ATCGAGATCTAATTCTCATGTTTGACAGCTTATCAT3'
     BglII ptac2:                                    SEQ ID NO:10
5'ATCGTCTAGAGCTGTTTCCTGTGTGAAATTGTTATCCG3'
     XbaI
```

The obtained PCR fragment was loaded on an agarose gel to check for its correct size. It was then digested by the BglII and XbaI and inserted into the pET9a (Novagen) hydrolyzed by the same enzymes. The obtained ligation products were transformed into TOP10 (Invitrogen) competent cells and selected on their kanamycine resistance. The obtained ptac vector was then checked by digestion with several enzymes and by sequencing analysis using oligonucleotides ptac1 and ptac2 as sequencing primers.

The ligation products, containing r-hIL-7 fragment, were transformed into TOP10 competent cells. The selection for plasmid-containing cells was on the basis of the antibiotic (kanamycin) resistance marker gene carried on the vector. Plasmid DNA from a positive clone was isolated from cultured cells, selected by restriction mapping and the correct DNA sequence confirmed by sequencing analysis using pET universal primers as sequencing primers (Novagen) as well as a ptac specific primer:

```
ptac promoter primer:                     SEQ ID NO:11
5'TTCGTGTCGCTCAAGGCGCA3'
```

The *E. Coli* final expression plasmid comprising SEQ ID NO:1, called ptac-hIL-7 (cf.: Figure no 1), was subcloned into *E. coli* JM101 cells (ATCC).

1.2. Construction of Simian IL-7-Coding Nucleotide Sequence:

a) Amplification and Sequencing of Simian IL-7 cDNA Including 5' Region

The simian (*Macaca Mulatta* Rhesus monkey) IL-7 encoding cDNA sequence was obtained from rhesus monkey kidney cDNA (BioChain Inc.) using PCR amplification (Mullis et al.; 1987; Methods in Enzymology; 155:335-350). The basic strategy was to amplify simian IL-7 cDNA by PCR with specific oligonucleotide primers used to amplify human IL-7 cDNA (SEQ ID NO: 5: IL75' and SEQ ID NO: 6: IL73'). A single band was apparent on gel electrophoresis (cf. FIG. 6). Asymmetric PCRs and sequencing permit to obtain the simian IL-7 sequence. Sequence homology analysis between human and simian IL-7 DNA and amino acid sequences showed 98.1% and 96.6% of homology-identity for DNA (cf. FIG. 4) and amino acid (cf. FIG. 5) sequences respectively.

b) Construction of Simian IL-7-Coding Nucleotide Sequence

Like the human IL-7 sequence, the simian IL-7-encoding DNA sequence presents at position 49 after the "ATG" initiation codon, a second putative "ATG" which could behave as a second initiation codon in *E. Coli*, since this second "ATG" is preceded by a "pseudo Shine-Dalgarno" sequence (ribosome binding sequence). To avoid the potential production of an amino-terminal truncated form of r-sIL-7, some of the nucleotides of the "SD-like" sequence were mutated (without modifying the resulting encoded r-sIL-7 amino acid sequence), thereby producing an improved methionyl-IL-7-coding-DNA sequence containing one or more preferred codon(s) for expression in *E. Coli* cells.

The amplification of the simian IL-7 encoding DNA sequence lacked of the SD-like sequence was performed by site directed mutagenesis PCR, using oligonucleotide primers: SEQ ID NO: 7: mutIL75' and SEQ ID NO: 6: IL73').

PCR products were analyzed by polyacrylamide or agarose gel electrophoresis in the presence of ethidium bromide and visualization by fluorescence of DNA bands stimulated by UV irradiation. A single major product band of the size corresponding to the IL-7 PCR fragment (cf. FIG. 7) was isolated and inserted into the plasmid vector pCR II-TOPO (Invitrogen) using the TA-cloning method. The ligation products were transformed into TOP10 competent cells. To select positive clones, plasmid DNA, prepared from cultured individual bacterial clones kanamycin resistant by Plasmid Miniprep Isolation techniques, were analyzed by restriction mapping and confirmed by dideoxy Sequencing (Sanger et al.; 1977; Proceedings of the National Academy of Sciences of the USA; 74:5463-5467) of an asymmetric PCR product DNA using pCR II TOPO universal primers (Invitrogen) as sequencing primers yielded about 700 bases containing sIL-7 sequences.

Plasmid DNA from a positive clone was digested with restriction endonucleases BamHI and NdeI and the resulting fragment, r-sIL-7 encoding DNA sequence, was inserted into ptac vector, as described in example 1.1., which was also digested with BamHI and NdeI restriction sites. The ligation products were transformed into TOP 10 competent cells. The selection for plasmid-containing cells was on the basis of the antibiotic (kanamycin) resistance marker gene carried on the vector. Plasmid DNA from a positive clone was isolated from cultured cells, selected by restriction mapping and confirmed by sequencing analysis using T7 terminator universal primer on one hand and ptac promoter primer on the other hand as sequencing primers.

The *E. Coli* final expression plasmid comprising SEQ ID NO: 12, called ptac-sIL7opt (cf.: Figure no 2), was subcloned into *E. coli* JM101 cells.

A2. Mammalian Expression (BHK Cell Expression, or CHO Cell Expression or HEK-293 Cell Expression):

The human IL-7 encoding cDNA sequence was amplified by polymerase chain reaction (PCR) (Mullis et al.; 1987; Methods in Enzymology; 155:, 335-350) from human placenta cDNA (BioChain Inc.), using oligonucleotides as primers in attempts to amplify the portions of the cDNA of interest: the IL-7 cDNA fragments linked at the 5' end to the natural IL-7 peptide signal.

The following oligonucleotides were used, which contain restriction endonuclease recognition sequences and kozak sequence:

```
PSIL75':                                    SEQ ID NO: 8
5'GCAAGCTTGCCACCATGTTCCATGTTTCTTTTAGGTATATCTTTGGAC
3'
    HindIII Kozak sequence IL73':                                      SEQ ID NO: 6
5'AGCCGGATCCTTATCAGTGTTCTTTAGTGCCCATCA3'
     BamHI
```

PCR products were assayed by polyacrylamide or agarose gel electrophoresis in the presence of ethidium bromide and visualization by fluorescence of DNA bands stimulated by UV irradiation (cf. FIG. 8). The product band of the size corresponding to the IL-7 PCR fragment, designated "hPSIL-7 cDNA", was isolated and inserted into the plasmid vector pCR II-TOPO (Invitrogen) using the TA-cloning method. The ligation products were transformed into TOP10 competent cells. To select positive clones, plasmid DNA, prepared from cultured individual bacterial clones ampicillin resistant by Plasmid Miniprep Isolation techniques (Biorad), were analyzed, by restriction mapping and confirmed by dideoxy sequencing (Sanger et al.; 1977; Proceedings of the National Academy of Sciences of the USA; 74:5463-5467) of an asymmetric PCR product DNA using pCR II TOPO universal primers as sequencing primers.

Plasmid DNA from a positive clone was digested with restriction endonucleases HindIII and BamHI and the resulting fragment, "hPSIL-7 cDNA" fragment, was inserted into pcDNA3.1(+) vector polylinker (Invitrogen) which had been digested with BamHI and HindIII restriction sites. This vector includes a gene for the selection and amplification of clones. The ligation products were transformed into TOP10 competent cells. The selection for plasmid-containing cells was on the basis of the antibiotic (ampicilin) resistance marker gene carried on the vector. Plasmid DNA from a positive clone was isolated from cultured cells, selected by restriction mapping and confirmed by sequencing analysis using pcDNA3.1(+) universal primers as sequencing primers (Invitrogen). The expression system was designed to express an IL-7 protein predicted from the translation of the natural human IL-7 gene sequence. Selection for recombinant vector-containing cells was done on the basis of the antibiotic (Ampicilin for cloning in *E. Coli* and Neomycin for expression in mammalian cells) resistance marker gene carried on the vector.

The mammalian (HEK-293, CHO or BHK) expression vector comprising SEQ ID NO:3, is called pcDNA-hPSIL-7 (cf.: Figure no 3). Expression of human IL-7 in HEK-293 or CHO transfected cells was achieved using the expression vector pcDNA-hPSIL-7. After linearization by BglII, expression vector, pcDNA-hPSIL-7, was transfected in the mammalian host cells using methods known to those skilled in the art. The selectable marker used to establish stable transformants was G418 (Invitrogen).

A3. Inducible Mammalian Expression (HEK293, HEK, T-REX™-293, T-REX™-HeLa, T-REX™-CHO, T-REX™-Jurkat Cell Lines):

The human IL-7 encoding cDNA sequence was isolated from the pcDNA-hPSIL-7 by digestion with restriction endonucleases HindIII and BamHI. The resulting "hPSIL-7 cDNA" fragment was purified on agarose gel and inserted into the pcDNA4/TO (Invitrogen) hydrolyzed with the same enzymes. The ligation products were transformed into TOP10F' competent cells (Invitrogen). The selection for plasmid-containing cells was on the basis of the antibiotic (Ampicillin) resistance marker gene carried on the vector. Plasmid DNA from positives clones were isolated from cultured cells, checked by restriction mapping and confirmed by sequencing analysis using the universal CMV forward and BGH reverse primers.

The expression system was designed to express, after induction with tetracycline or analogous, an IL-7 protein predicted from the translation of the natural human IL-7 gene sequence.

Selection for recombinant vector-containing cells was done on the basis of the antibiotic (Ampicillin for cloning in *E. coli* and Zeocin for expression in mammalian cells) resistance marker gene carried on the vector).

The inducible mammalian expression vector is called phT-PSIL7h (cf.: Figure no 14). Expression of human IL-7 in HEK-293, HEK, T-REX™-293, T-REX™-HeLa, T-REX™-CHO or T-REX™-Jurkat transfected cells was achieved using the expression vector phT-PSIL7h. After linearization by PvuI, expression vector, phT-PSIL7h, was transfected in the mammalian host cells using methods known to those skilled in the art. The selectable marker used to establish stable transformants was zeocin (Invitrogen).

After a first selection, in order to enhance the PSIL7 sequence copy number in the cells, stable clones are retransfected by the same plasmide or by the same kind of plasmide (differed by the selection marker): PSIL7 inserted into pcDNA5/T0 (Invitrogen)

A4. Transient Mammalian Expression via an Adenovirus in A549, HeLa, VERO, BHK or CHO Cells:

The human IL-7 encoding cDNA sequence was amplified by polymerase chain reaction (PCR) (Mullis et al.; 1987; Methods in Enzymology, 155:335-350) from the pcDNA-hPSIL-7, using oligonucleotides as primers in attempts to amplify the cDNA of interest (IL-7 cDNA linked to its natural peptide signal) between EcoRV and MluI restriction sites.

The following oligonucleotides were used:

```
PSIL7EcoRV5':                               SEQ ID NO 14
5'AGATATCATGTTCCATGTTTCTTTTAGGTA3'
   EcoRV
```

PCR products were assayed by agarose gel electrophoresis in the presence of ethidium bromide and visualization by fluorescence of DNA bands stimulated by UV irradiation. The obtained product band, corresponding to the expected size of the hPSIL-7 cDNA, was isolated and inserted into the plasmid vector pCRII-TOPO (Invitrogen) using the TA-cloning method. The ligation products were transformed into TOP10F' competent cells. To select positive clones, plasmid DNA minipreparations (Biorad), prepared from cultured individual bacterial clones, were analysed by restriction mapping and confirmed by dideoxy sequencing (Sanger et al.; 1977; Proceedings of the National Academy of Sciences of the USA; 74:5463-5467) using pCRII-TOPO universal primers.

Plasmid DNA from a positive clone was digested with restriction endonucleases EcoRV and MluI. The resulting "hPSIL-7 cDNA" fragment was inserted into the pAdenoVator-CMV5(CuO) (Q biogene) and hydrolysed with the same enzymes. The ligation products were transformed into TOP10F' competent cells (Invitrogen). The selection for plasmid-containing cells was on the basis of the antibiotic (kanamycin) resistance marker gene carried on the vector. Plasmid DNA from positives clones were isolated from cultured cells, checked by restriction mapping and confirmed by sequencing analysis using the following primers:

```
pCMV5:                          SEQ ID NO: 16
5'CACTTGAGTGACAATGAC3' pSV40polyA:                     SEQ ID NO: 17
5'TCACTGCATTCTAGTTGT3'
```

For construction of the recombinant adenovirus vector, the obtained pAVc-PSIL7h (cf.: Figure no 15) is linearized by PmeI, purified on agarose gel and co-transformed with the pAdenoVatorΔE1/E3 into BJ5183 competent cells (Q Biogene). The selection for recombinant plasmid-containing cells was on the basis of the antibiotic (kanamycin) resistance marker gene carried on the vector. Plasmid DNA from positives clones were isolated from cultured cells, checked by restriction mapping.

The recombinant adenovirus vector is then amplified by transformation of DH5α competent cells, plated on LB/kanamycin plates, and midipreparation (Macherey Nagel) of DNA from cell cultures.

The sterile PacI linearized recombinant adenovirus DNA (AdVc-PSIL7h DNA) is used to transfect QBI-293A cells, efficient cells to complement the recombinant adenovirus and produce recombinant viral particles.

A5. Mammalian Co-Expression of IL-7 and BclXL (BHK Cell Expression, or CHO Cell Expression or HEK-293 Cell Expression):

The human IL-7 encoding cDNA sequence was isolated from the pcDNA-hPSIL-7 by digestion with restriction endonucleases HindIII and BamHI. The resulting "hPSIL-7 cDNA" fragment was purified on agarose gel and inserted, downstream the pCMV promoter, into the pBudCE4.1 vector (Invitrogen) which had been digested with HindIII and BamHI restriction sites.

The human BclXL encoding cDNA sequence was amplified by polymerase chain reaction (PCR) (Mullis et al.; 1987; Methods in Enzymology; 155:, 335-350) from human Raji lymphoma cells cDNA (Clontech), using the following oligonucleotides as primers.

```
BclXL5'NotI:                    SEQ ID NO: 14
5'TAGCGGCCGCATGTCTCAGAGCAACCGG3'
    NotI

BclXL3'BStBI:                   SEQ ID NO: 15
5'ACTTCGAATCATTTCCGACTGAAGAGTG3'
    BstBI
```

PCR products were assayed by polyacrylamide or agarose gel electrophoresis in the presence of ethidium bromide and visualization by fluorescence of DNA bands stimulated by UV irradiation. The product band of the size corresponding to the BclXL PCR fragment was isolated and inserted into the plasmid vector pCR II-TOPO (Invitrogen) using the TA-cloning method. The ligation products were transformed into TOP10 competent cells. To select positive clones, plasmid DNA, prepared from cultured individual ampicilin resistant bacterial clones by Plasmid Miniprep Isolation techniques (Biorad), were analyzed, by restriction mapping and confirmed by dideoxy sequencing (Sanger et al.; 1977; Proceedings of the National Academy of Sciences of the USA; 74:5463-5467) of an asymmetric PCR product DNA using pCR II TOPO universal primers as sequencing primers.

Plasmid DNA from a positive clone was digested with restriction endonucleases NotI and BstBI and the resulting fragment was inserted, downstream the pEF$_{1\alpha}$ promotor, into pBudCE4.1-hPSIL-7 vector which had been digested with NotI and BstBI restriction sites.

The resulting mammalian (HEK-293, CHO or BHK) expression vector, comprising SEQ ID NO:3, 16 or 18, is called pBud-hPSIL-7-BclXL (cf.: Figure no 17).

Example B

Fermentation of *E. coli* Producing Recombinant IL-7

Fermentations for the production of recombinant (human or simian) IL-7 were carried out in 80 liters fermentor (New Brunswick) using an *E. coli* JM101 host strain transformed with expression plasmid ptac-hIL-7 or ptac-sIL7opt as described in example A1.

1 L inoculum culture was aseptically transferred into fermentor containing 50 L batch medium NRJ18 (pH7). The culture was grown in batch mode (T 37° C., agitation: 100-500 rpm D.O$_2$: 30%). The production phase of the fermentation was induced by IPTG (200 mg/L) after D.O$_2$ reached to 0% until the OD-600 of the culture was about 40. The fermentor content was collected and cooled for at least 30 min in order to reach temperature under 20° C. The culture media was filtered using a 70 μm filter (PALL R1F-700) to eliminate precipitates and cells were harvested by centrifugation (Beckman J6) at 5000 g for 30 min at 4° C.

For inducible clones, during the 10 days of culture, cells will daily be subtracted from the perfusion reactor and induced by tetracycline in a batch reactor.

Example C

Fermentation of HEK-293 Cells Producing Recombinant hIL-7

The best stable positive done, as in example A2 was adapted to serum-free suspension culture by several media screenings in order to produce a clone optimized for productivity and growth in high cell density culture. Cell culture was performed in a 3 liters bioreactor with a perfusion system. The cells were allowed to grow to a concentration of 10 millions cells/ml. The reactor was operated at a continuous perfusion rate of approximately 3 L/day during 10 days. Roughly 30 L of serum-free culture media containing recombinant protein were generated and used as starting material for the purification of the r-hIL-7.

Example D

Purification of Recombinant IL-7 Product Expressed in *E. Coli*

The harvested cells, as in example B, were suspended in Tris 20 mM/EDTA 10 mM buffer (pH8) and centrifuged at 16900 g for 45 min at 4° C. After two successive washing/centrifugation cycles, inclusion bodies fractions were recovered.

This inclusion bodies fraction was diluted in order to obtained a protein concentration of 5 to 6 mg/ml and solubilized in solubilization buffer (8 M guanidine hydrochloride-1 mM EDTA-1% b-mercaptoethanol-0.5% DMDAP-10 mM sodium phosphate-pH8) giving a full reduction, denaturation and solubilization of the protein. The solution was diluted 1.6 fold in sodium phosphate buffer 6.25 mM and adjusted to 1.5

M ammonium sulfate, pH7. The final concentration of guanidine hydrochloride reached 5M.

The solubilized inclusion bodies were pre-filtered and then loaded onto an HIC Butyl 650M (Toso Haas) column equilibrated with the loading buffer (6.25 mM sodium phosphate-5 M guanidine hydrochloride-1.7M ammonium sulfate-pH7). After sample application and washing of the column with the same buffer, elution is carried out in one step with 100% of elution buffer (6.25 mM sodium phosphate, 5 M guanidine hydrochloride, pH 7). All the fractions were collected, pooled and adjusted to a O.D.280=0.5 by diluting in 6.25 mM sodium phosphate pH 7, 5 M guanidine hydrochloride buffer. During this step, various contaminants, among which DNA, which would lower the recovery of the subsequent refolding step, were eliminated.

IL-7 was allowed to renature by dilution into the refolding buffer: the pooled fractions from HIC was diluted 2.5 fold in 83.3 mM Tris buffer, 0.16% tween 80, 0.5 M L-arginine, 0.166 mM oxydized gluthatione and 1.6 mM reduced gluthatione pH 8.5. The dilution process was performed on a linear mode, over a 2 hours period, while stirring the receiving buffer. The renaturation step could be performed fixed on a solid support.

Renaturated IL-7 was loaded in two times onto either membrane filtration or a G25 Sephadex (Pharmacia) column equilibrated with elution buffer (20 mM sodium phosphate, 0.2 M L-arginine, pH 7) and eluted in order to allow the proper load of r-IL-7 on the subsequent affinity support.

The protein peak obtained from the G25 step was loaded onto an Heparin Sepharose Fast Flow (Pharmacia) column equilibrated with a loading buffer (20 mM sodium phosphate, 50 mM sodium chloride, pH 7). After sample application and washing of the column with the loading buffer, elution was carried out in two steps. At first, a fixed ratio of 25% elution buffer (20 mM sodium phosphate, 1 M sodium chloride, pH 7)/loading buffer was applied over 20 column volumes. Then, refolded IL-7 was eluted in one step with 60% of elution buffer/loading buffer. The strong selectivity of this step conducted to the elution of the correctly refolded r-IL-7 conformer.

In order to eliminate most of the residual impurities including endotoxins, the fraction was adjusted to pH 5 and subjected to a Carboxymethyl Ceramic (BioSepra) column. The CMC column was equilibrated with loading buffer (50 mM sodium acetate, pH 5). After sample application and washing of the column with washing buffer (50 mM sodium acetate, sodium chloride 0.2 M, pH 6), elution was carried out in one step with buffer (50 mM sodium acetate, 0.8 M sodium chloride, pH 6). Finishing steps may also included a G25 Sephadex purification step for desalting followed by a Q Sepharose Fast Flow (QFF Pharmacia) which retained various residual contaminants. R-IL-7 drug substance was recovered pure in the flow through, as shown in FIG. 9 representing SDS-PAGE analysis: Coomassie blue colored and silver stained.

Example E

Purification of Recombinant Human IL-7 Product Expressed in HEK-293 Cells

Crude cell culture fluid, generated by growth of expression system HEK-293-pcDNA-hPSIL-7 as reported in example C, was treated using a traditional approach or a Streamline ion exchanger mode.

In a Streamline procedure, crude cell culture fluid was transferred directly from the fermentor to the expanded bed of Streamline ion exchange or heparin, or Sulfopropyl (SP) or Diethyl Aminoethyl (DEAE), followed by a combination of IEX and HIC. Finishing steps may include filtration and concentration. In a traditional approach, crude cell culture fluid was clarified using a combination of filtration and concentration [microfiltration (0.45 µm) ultra/diafiltration] steps to isolate the product. The protein solution obtained was loaded onto an ion exchange combination and Heparin Sepharose [Fast Flow (Pharmacia) column] in various combinations to purify the product.

Finishing steps may also included a Hydrophobic Interaction Exchange (HIC) and a filtration/ultrafiltration (UF) or a Carboxymethyl Ceramic (BioSepra) purification step for eliminating residual impurities followed by a G25 Sephadex purification step for desalting followed by a Q Sepharose Fast Flow (QFF Pharmacia) which retained various residual contaminants. R-IL-7 drug substance was recovered pure in the flow through of the last purification step.

Example F

Product Controls and Specifications

F1. Drug Substance Controls and Specifications:

| CONTROLS | TESTS |
| --- | --- |
| IDENTITY | Western Blot |
|  | Size-exclusion HPLC |
| PROCESS RELATED IMPURITIES | *Escherichia Coli* Protein (ECP) Dosage |
|  | Bacterial Endotoxins Dosage |
|  | LAL test |
|  | DMA Quantification (Hybridation, quantitative PCR) |
|  | SDS-PAGE Silver staining |
| PRODUCT RELATED IMPURITIES | Reverse phase HPLC |
|  | Ion Exchange HPLC |
|  | Size-exclusion HPLC |
|  | Heparin Affinity HPLC (this control warrant the obtention of the correctly refolded Drug Substance) |
| STERILITY | Microbiology sterility |
| PURITY | Size-exclusion HPLC |
| POTENCY | Bioassay |
| QUANTITY | BCA |
|  | ELISA |
|  | Size-exclusion HPLC |
|  | UV Absorbtion |

F2. Example Lot X r-, hIL-7 Batch Results

| TEST | METHODS | SPECIFICATIONS | OBTAINED |
|---|---|---|---|
| CHARACTERS | | | |
| Appearance | Visual control | Colorless liquid | comply |
| pH | PH meter | pH = 6.2 ± 0.1 | comply |
| IDENTIFICATION | | | |
| Western blot | Internal Monograph | Main band recognized by the specific anti-hIL-7 antibody at 17.5 kDa | comply |
| Size-exclusion HPLC | Internal Monograph | Retention time: 23.7 +/− 0.2 mn | comply |
| TEST | | | |
| Purity by SE-HPLC | Internal Monograph | Polypeptidic purity ≧ 96% (including dimer) | 99% No Dimer |
| Quantity by SE HPLC | | | |
| Purity by RP-HPLC | Internal Monograph | Polypeptidic Purity ≧ 96% | 96% secondary forms |
| Purity by SDS-PAGE (Silver stained) | Internal Monograph | Polypeptidic Purity ≧ 96% (including dimer) | 98% |
| Purity by Cation exchange HPLC | CYT Internal Monograph | Polypeptidic Purity ≧ 96% | 96% including secondary forms |
| Host Proteins by ELISA | CYT Internal Monograph | <100 ppm | 50 ppm |
| Plasmid DNA by hybridization | CYT Internal Monograph | <100 pg/dose <10 pg/mg protein | 20 pg/dose |
| Endotoxins | CYT Internal Monograph | <100 EU/dose <10 EU/mg protein | 3 EU/mg |
| Sterility | CYT Internal Monograph | Sterile | comply |
| ASSAY | | | |
| IL-7 content by ELISA assay | CYT Internal Monograph | 50% < Standard Potency < 150% | 90% of standard |
| Total protein content by BCA assay | CYT Internal Monograph | Quantification | 40 mg/L-60 mg/L |

Characterization and proof of structure of this conformer included an amino acid analysis, a peptide mapping after tryptic digest, the sequence of the amino-terminal part, a mass spectrometry (MALDI TOF) control of the molecular weight, a mass spectrometry control of the disulfide bridges, and protein profiles through: SDS PAGE silver stain, Reverse phase HPLC, Cation exchange HPLC, Size exclusion HPLC.

F3. Peptide Mapping

Peptide sequences was conform with expected sequences of a r-hIL-7 tryptic digest

| Mass | Position | Peptide sequence |
|---|---|---|
| 911.324 | 1-8 | MDCDIEGK |
| 319.161 | 9-11 | DGK |
| 2099.040 | 12-29 | QYESVLMVSIDQLLDSMK |
| 1775.806 | 30-44 | EIGSNCLNNEFNFFK |
| 175.119 | 45-45 | R |
| 800.372 | 46-52 | HICDANK |
| 899.444 | 53-59 | EGMFLFR |
| 317.193 | 60-62 | AAR |
| 147.113 | 63-63 | K |
| 288.203 | 64-65 | LR |
| 535.324 | 66-69 | QFLK |
| 1490.731 | 70-82 | MNSTGDFDLHLLK |
| 1662.873 | 83-98 | VSEGTTILLNCTGQVK |

-continued

| Mass | Position | Peptide sequence |
|---|---|---|
| 232.140 | 99-100 | GR |
| 1210.679 | 101-112 | KPAALGEAQPTK |
| 719.357 | 113-118 | SLEENK |
| 347.229 | 119-121 | SLK |
| 404.214 | 122-124 | EQK |
| 147.113 | 125-125 | K |
| 965.512 | 126-133 | LNDLCFLK |
| 175.119 | 134-134 | R |
| 743.466 | 135-140 | LLQEIK |
| 651.292 | 141-145 | TCWNK |
| 662.391 | 146-151 | ILMGTK |
| 285.119 | 152-153 | EH |

F4. Mass Spectrometry MALDI-TOF: Protein MW

Average mass of protein with one charge (M+H)+. The measurement gave a molecular mass of 17517.6 Da for a theoretical value of 17518.4 Da F5. Mass Spectrometry MALDI-TOF: Sulfhydryl Groups

| | | | Mass of monoisotopic peptides charged one time (M + H)+. | |
|---|---|---|---|---|
| Calculated mass. | Measured mass. | peptide | sequence | observations |
| 535.32 | 535.22 | 66-69 | QFLK | |
| 662.39 | 662.31 | 146-151 | ILMGTK | |
| 719.36 | 719.29 | 113-118 | SLEENK | |
| 743.47 | 743.40 | 135-140 | LLQEIK | |
| 899.44 | 899.44 | 53-59 | EGMFLFR | |
| 1210.68 | 1210.68 | 101-112 | KPAALGEAQPTK | |
| 1448.64 | 1448.66 | 46-52/141-145 | HICDANK-TCWNK | Disulfide bridge C48-C142 |
| 1490.73 | 1490.75 | 70-82 | MNSTGDFDLHLLK | |
| 2099.04 | 2099.04 | 12-29 | QYESVLMVSIDQLLDSMK | |
| 2570.22 | 2570.23 | 1-8/83-98 | MDCDIEGK-VSEGTTILLNCTGQVK | Disulfide bridge C3-C93 |
| 2738.30 | 2738.28 | 30-44/126-133 | EIGSNCLNNEFNFFK-LNDLCFLK | Disulfide bridge C35-C130 |

Example G

In Vitro Biological Activity Assay of Recombinant IL-7

Mammalian (human and simian) IL-7 expressed in *E. coli* (Example A1), purified and characterized as in example D, were assayed and compared to murin IL-7 (R&D System) for their ability to stimulate the proliferation of the IL-7 dependent cell line designated as pre-B cell line PB1 (DSMZ, Deutsche Sammlung von Mikroorganismen und Zellkulturen, Braunschweig, Germany), a cell line derived from bone marrow cells from CBA/C57BL mice.

Also, human and simian r-IL-7 "impure", generated from purification process using partial denaturation step or by chemically-treated purified r-IL-7 in order to generate about 20% of deamidated IL-7 form or dimer form, were assayed.

The PB-1 cell line is absolutely dependent upon exogenous IL-7 for continued growth and viability. The addition of r-IL-7 to theses cultured cell lines stimulates a dose dependent proliferation allowing for a quantitative determination of the levels of r-IL-7 present. The amount of proliferation is measured by "pulsing" each microwell with tritiated thymidine 3H-TdR for 4 hours at 37° C. Dividing pre-B cells will incorporate 3H-Tdr into their DNA. The cells from each well are then harvested onto glass fiber filter discs which trap the DNA. The amount of specifically-bound radioactivity is then measured in a liquid scintillation counter. The number of counts per minute (cpm) for each well is directly proportional to the amount of proliferation by the activated pre-B cells in response to IL-7.

All IL-7 proteins were active on Murine pre-B cell line as indicated in FIG. 10.

Example H

Assays for Detection of Antibodies to Recombinant IL-7 in Serum

Human recombinant IL-7 is heterologous for monkey models and may induce neutralizing antibodies against recombinant human IL-7 conformer (as describe above). These antibodies may function as inhibitors in vivo and may contribute to the immunosuppressive therapeutic effects of the drug substance. On this basis, anti-IL-7-antibodies were investigated in serum and plasma of animals treated with r-hIL-7 or r-sIL-7 pure (according to the present invention) or r-sIL-7 "impure" as describe in next examples.

Methods used for the detection of antibodies in body fluids may included cytokine bioassay, immunometric assay, radio-ligand assay and various blotting techniques.

The plasmatic quantification of anti-r-IL-7 antibodies were achieved using ELISA technique and the serological detection of anti-r-IL-7 antibodies were realized using Western blot technique. These techniques are known to those skilled in the art.

H1. ELISA Procedure:

ELISA Strip Plate was coated with r-IL-7 (human or simian) diluted in Blocking buffer containing tween at 0.75 µg/ml. After overnight incubation at 4° C., the saturation of the plate was performed with Blocking Buffer for 1 h at RT. After removing all solution and washing the plate with Washing Buffer, the plate was ready to use for the assay.

Serial dilutions of preimmune and immune plasma were performed and dispensed to wells. Plate was incubated for 1 h at 37° C. Positive control (biotyniled IL-7 antibody) and negative control (serum of placebo monkey) were tested as well in specific wells. Plate was then washed with Washing Buffer and incubated, at RT for 30 min with IgG monkey-HRP diluted in Blocking Buffer/tween for serum and negative control. Positive control wells were incubated with streptavidine HRP in Blocking Buffer/tween. After removing the solution, the plate was washed with Washing Buffer and incubated, at RT for up to 15 min with OPD Substrate solution followed by addition of sulfuric acid in each well to stop the reaction.

The absorbance was then read at 492 nm.

H2. Western Blot Procedure

Recombinant (human or simian) IL-7 was transferred onto nitrocellulose or PVDF membrane. Then the membrane was incubated with the sera of treated animals (dilution of 1/100 or 1/200) or with anti-IL-7 antibody (Anti-human IL-7 antibody: AB 207 NA, R&D System) for the positive control. After removing the solution, the membrane was washed and incubated with the secondary antibody. Anti-monkey IgG alkaline phosphatase conjugate (SIGMA A1929) or Anti-goat IgG alkaline phosphatase conjugate (SIGMA A4187) for the positive control. Then, the revelation was performed using BCIP/NBT (SIGMA).

Example I

In Vivo Effects of r-IL-7 on CD4 T Cell Count in Normal Non Human Primate Model Recombinant IL-7 (human and simian) expressed in *E. coli* (Example A1), purified and characterized as in example D, and r-sIL-7 "impure" (as defined in example G) were tested for in vivo biological activity in normal primates. This primate model was the only possible model to test the long term activity of the drug substance and the immunogenicity of the same drug substance contaminated with molecular variants and/or drug product related impurities. To test the same effect in rodents would be inconclusive: first because rodent sequences show an important deletion in comparison to primate sequences, second because in rodent, IL-7 has a strong lymphopoietic effect on B cells, susceptible to mask the T cell lymphopoietic effect or to prevent from a clear discriminative analysis of this effect. For this reason, in order to prove the effect in primates, while avoiding the unethical testing of an immunogenic preparation in human, we had to clone and express and purify simian IL-7 and test it in monkey.

Young Macaca rhesus monkeys were studied in four groups (1 to 4), each group contained 3 animals.

Monkeys of:
group 1 received placebo (IL-7 diluent)
group 2 received r-hIL-7 (according to the present invention) at a dose of 150 µg/kg administered once daily by subcutaneous injection for 4 weeks
group 3 received r-sIL-7 (according to the present invention) at a dose of 150 µg/kg administered once daily by subcutaneous injection for 4 weeks
group 4 received single daily subcutaneous administration of r-sIL-7 "impure" at a dose level of 150 µg/kg for 4 weeks.

All animals were studied during 6 weeks: 4 weeks of treatment and 2 weeks for reversibility period.

Peripheral blood specimens were collected from animals under ketamine restraint before and after IL-7 treatment (on days 0 (pretreatment), 7, 14, 21, 28, 35 and 42). CD4 cellularity was examined on a FACScan cell analysis system (Becton Dickinson). Serum samples were examined for the presence of antibodies by western blot analysis and confirmed by ELISA analysis, as describe in example H. Blood CD4 T cell count is indicated in FIG. 11: represented as a median of blood CD4 T cell count for each group.

All animals survived the protocol and tolerated IL-7 administration without adverse reactions to IL-7 therapy.

The various IL-7 administered had a moderate effect on blood CD4 T cell count of normal monkeys: peripheral blood CD4 T cell count increased 1.4 to 2.1× from day 14 until day 35 and remain above pretreatment values at day 42 in group 3 (treated with r-sIL-7) compared to placebo group and CD4 cellularity began to increase and then decreased from week 2 until week 6 for groups 2 (treated with r-hIL-7) and 4 (treated with r-sIL-7 "impure" preparation).

Anti-IL-7 antibodies were detected in the sera of these two groups of monkeys (2 and 4), during the second week after receiving r-hIL-7 and r-sIL-7 "impure" respectively, by subcutaneous injection (cf. FIG. 12). In these normal monkeys, the repeated injection of heterologous or impure IL-7 drug substance did trigger the appearance of anti-IL-7 antibodies and simultaneously this produced a strong decrease of the IL-7 lymphopoietic effect.

Example J

In Vivo Activity of r-sIL-7 in Irradiated Monkeys

Recombinant simian IL-7 expressed in *E. coli* (Example A1), purified and characterized as in example D, and r-sIL-7 "impure" (as defined in example G) were tested for mid or long term in vivo biological activity in immunodepressed primates. Young rhesus monkeys were studied in three groups (1 to 3), each group contained 3 animals.

All monkeys underwent total body irradiation (TBI) (6.1 Gy).

Monkeys received following regimens:
group 1 received placebo (IL-7 diluent)
group 2 received r-sIL-7 (according to the present invention) at a dose of 70 µg/kg administered once daily by subcutaneous injection for 4 weeks starting on day 14 post-irradiation.
group 3 received single daily subcutaneous administration of r-sIL-7 "impure" at a dose level of 70 µg/kg for 4 weeks starting on day 14 post-irradiation.

All animals were studied during 10 weeks: 2 weeks for post-irradiation hematological recovery period, 4 weeks for IL-7-treatment period and 4 weeks of follow up period.

Blood specimens, for CD4 T cell count, were collected from the animals under ketamine restraint on days 0, 7 and 14 pretreatment, 21, 28, 35 and 42 of treatment, 49, 56, 63 and 70 post-irradiation.

CD4 cellularity was examined on a FACScan cell analysis system (Becton Dickinson) and serum samples were examined for the presence of antibodies using ELISA and western blot techniques as describe in example H.

All animals survived the protocol and presented no adverse reactions to the IL-7 treatment.

As indicated in FIG. 13, IL-7 administration increased significantly (4.2-fold) the CD4 T cell in the peripheral blood of immunocompromised monkeys of groups 2 and 3 compared to untreated control group. The group 3 treated with subcutaneous administration of r-sIL-7 "impure" display a diminution of the in vivo biological effect of IL-7 starting after 3 to 4 weeks of IL-7 treatment.

Anti-IL-7 antibodies were measured in the serum of these animals every week after beginning of IL-7 treatment. Anti-IL-7 antibodies were not detected up to week 10 (8 weeks post-treatment) in group 2 treated with r-sIL-7 (according to the present invention). In contrary, group 3, treated with an impure preparation showed detectable antibodies as soon as week 6 (4 weeks after beginning of IL-7 treatment). At week 10, antibodies were clearly present and exogenous IL-7 had no lymphopoietic effect.

Example K

In Vivo Activity of Recombinant Human IL-7 on Pharmacodynamic Parameters and Total Lymphocyte Count in Normal Cynomolgus Monkeys Recombinant human IL-7 (r-hIL-7) expressed in *E. coli* (Example A1), purified and characterized as in example D, was tested for in vivo biological activity on pharmacodynamic parameters and total lymphocyte count in normal cynomolgus monkeys.

Four normal female Cynomolgus monkeys received subcutaneous bolus single injection of soluble r-hIL-7 at the dose level of 100 µg/kg.

All animals were studied over 96 hours.

Laboratory investigations (hematology and immune cell phenotyping) were performed before r-hIL-7 single injection and 6, 24, 48, 72 and 96 hours post-injection.

Cellularity and immunophenotyping of lymphocyte subsets were examined by Flow Cytometry using highly specific cell surface antibody markers including: CD3, CD4, CD8, CD20, CD127, Ki67 and Bcl2 in various combinations.

Observed variations in lymphocyte count and specific markers were reported in the next table and in histogram referred as figure . . . :

| | Lympho 10^6/ml | CD 20% | CD 3% | CD 4% | CD 8% | Ki 67% | CD 127% | BCL-2% |
|---|---|---|---|---|---|---|---|---|
| before | 8.929 | 14.75 | 36.80 | 10.94 | 38.23 | 1.93 | 40.86 | 21.61 |
| day 1 (+6 hrs) | 4.823 | 24.90 | 21.48 | 6.35 | 23.83 | 2.39 | 6.95 | 11.03 |
| day 2 | 4.851 | 12.80 | 27.63 | 8.45 | 26.82 | 3.41 | 4.55 | 52.15 |
| day 3 | 4.880 | 8.55 | 27.88 | 5.75 | 32.40 | 3.81 | 8.10 | 49.30 |
| day 4 | 6.441 | 13.45 | 58.25 | 19.85 | 48.83 | 7.71 | 23.43 | 65.63 |
| day 5 | 8.003 | 9.33 | 45.33 | 11.23 | 43.50 | 5.21 | 42.53 | 30.23 |

After single injection of r-hIL-7:

- an apparent decline in the lymphocyte counts, CD3+ T cells, CD4+ and CD8+ subsets, in peripheral blood was observed as early as 6 hours and up to 72 hours. The cell counts returned to baseline values around 96 hours after the injection. This drop of peripheral lymphocyte counts is consistent with an early IL-7-induced trafficking of T lymphocytes from blood towards lymphoid tissues.
- a marked but transient decline in IL-7 receptor alpha chain (CD127) expression, by peripheral lymphocytes, was observed during the 48 hrs following the injection, reflecting a down-modulation of IL-7 receptor in response to a single dose of IL-7. CD127 expression started to reappear at 48 hrs coming back toward baseline values 96 hours after the injection.
- a delayed but significant increase of Ki67 expression, which is a marker of cell proliferation, was observed on both CD4+ and CD8+ cells up to 72/96 hours after the injection.
- a delayed increase of Bcl-2, which is a marker of apoptosis inhibition, was observed, proven to be involved in IL-7 activity.

The variations of the 3 latter markers showed that a single injection of r-hIL-7 induced a response of T cells, with significant effects over 48 hrs, detectable up to 72/96 hours. As assessed from peripheral blood lymphocyte counts, these changes of cell phenotypes are in part masked by T cell homing.

From these data it appears that a once daily administration of r-IL-7 is not the most appropriate dose regimen. Once every other day to once weekly appears to be a more appropriate dose regimen for humans.

The invention claimed is:

1. A composition of matter comprising a human or simian IL-7 conformer, wherein said conformer comprises the following three disulfide bridges: Cys: 1-4 (Cys2-Cys92); 2-5 (Cys34-Cys129) and 3-6 (Cys47-Cys141), wherein the total amount by weight of said IL-7 conformer in said composition of matter is at least 98% by weight and wherein said composition of matter is substantially free of IL-7 molecular variants or product related impurities.

2. The composition of matter according to claim 1, wherein said IL-7 conformer is a recombinant human IL-7 conformer that is not immunogenic in humans.

3. The composition of matter according to claim 2, wherein said IL-7 conformer comprises SEQ ID NO: 2.

4. The composition of matter according to claim 1, wherein said IL-7 conformer is a recombinant simian IL-7 conformer that is not immunogenic in non-human primates.

5. The composition of matter according to claim 4, wherein said IL-7 conformer comprises amino acids 26-177 of SEQ ID NO: 13.

6. The composition of matter according to claim 1, wherein said IL-7 conformer is not glycosylated.

7. The composition of matter according to claim 1, wherein said IL-7 conformer is glycosylated.

8. The composition of matter according to claim 1, wherein said IL-7 conformer is associated to the hepatocyte growth factor as a heterodimer.

9. The composition of matter according to claim 1, wherein said IL-7 conformer is functionally attached to a Fc portion of an IgG heavy chain through a peptide hinge region, said IgG being a human IgG1 or IgG4.

10. The composition of matter according to claim 1, wherein said IL-7 conformer is functionally associated to a Human Serum Albumin (HSA) or a portion of HSA as a fusion protein.

11. The composition of matter according to claim 1, wherein said composition of matter is substantially free of another IL-7 conformer.

12. The composition of matter according to claim 1, wherein the total amount by weight of IL-7 in said composition of matter is at least 99.5% by weight.

13. A pharmaceutical composition comprising an effective amount of a human or simian IL-7 conformer, wherein said conformer comprises the following three disulfide bridges: Cys: 1-4 (Cys2-Cys92); 2-5 (Cys34-Cys129) and 3-6 (Cys47-Cys141), wherein at least 98% of the total amount by weight of IL-7 consists of said conformer and wherein said composition is substantially free of IL-7 molecular variants or product related impurities, and one or more pharmaceutically acceptable carriers.

14. The pharmaceutical composition according to claim 13, wherein the pharmaceutically acceptable carrier is selected from the group consisting of sucrose, trehalose and an amino acid.

15. The pharmaceutical composition according to claim 14, wherein the pharmaceutically acceptable carrier is contained in an appropriate buffer to form an isotonic solution.

16. The pharmaceutical composition according to claim 15, wherein said appropriate buffer has a pH range of between 5 to 7.5.

17. The pharmaceutical composition according to claim 16, wherein said appropriate buffer is an organic salt selected from a sodium citrate buffer or an ammonium acetate buffer.

18. The pharmaceutical composition according to claim 13, wherein said composition is a lyophilized form.

19. The pharmaceutical composition according to claim 13, wherein said composition further comprises a protein or a surfactant.

20. The pharmaceutical composition according to claim 13, further comprising an immuno-stimulating agent selected from a hematopoietic cell growth factor, a cytokine, an antigen, an adjuvant, or a combination thereof.

21. The pharmaceutical composition according to claim 20, wherein said hematopoietic cell growth factor is selected from the group consisting of Stem Cell Factor (SCF), the soluble form of the SCF, G-CSF, GM-CSF, Flt-3 ligand, IL-15 and IL-2.

22. The pharmaceutical composition according to claim 20, wherein the cytokine is selected from the group consisting of γ interferon, IL-2, IL-12, RANTES, B7-1, MIP-2 and MIP-1α.

23. The pharmaceutical composition according to claim 20, wherein said antigen is selected from the group consisting of a synthetic or natural peptide, a recombinant protein, a killed, inactivated or attenuated pathogen product, a lipid, a portion thereof and a combination thereof.

24. The pharmaceutical composition according to claim 23, wherein said antigen is selected from the group consisting of antigens derived from HIV, Varicella Zoster virus, Influenza virus, Epstein Barr virus, type I or 2 Herpes Simplex virus, human cytomegalovirus, Dengue virus, Hepatitis A, B, C or E virus, Respiratory Syncytium virus, human papilloma virus, *mycobacterium tuberculosis*, *Toxoplasma* and *Chlamydia*.

25. The pharmaceutical composition according to claim 20, wherein said adjuvant is selected from any substance, mixture, solute or composition facilitating or increasing the immunogenicity of an antigen and able to induce a Th1-type immune response.

26. The pharmaceutical composition according to claim 13, wherein the effective amount of said IL-7 conformer is between about 3 to 300 μg/kg/day.

27. A method of producing an IL-7 drug substance as defined in claim 1, the method comprising:
   a) providing a sample comprising IL-7 polypeptides,
   b) purifying an IL-7 conformer which comprises the following three disulfide bridges: Cys: 1-4 (Cys2-Cys92); 2-5 (Cys34-Cys129) and 3-6 (Cys47-Cys141) to produce an IL-7 drug substance, and
   c) measuring or quantifying, in the drug substance, said IL-7 conformer.

28. The method according to claim 27, wherein said sample is obtained from a culture of recombinant prokaryotic or eukaryotic host cells producing IL-7 polypeptides.

29. The method according to claim 28, wherein said sample is or derives from a culture of prokaryotic host cells encoding an IL-7 polypeptide and further wherein the method further comprises, prior to step b):
   i) treating said sample to cause a complete denaturation of said IL-7 polypeptides,
   ii) purifying the denatured polypeptide obtained in step i) and
   iii) refolding the polypeptides.

30. The method according to claim 29, wherein step i) comprises the dissolution of inclusion bodies in a denaturant buffer.

31. The method according to claim 29, wherein step ii) is performed by hydrophobic chromatography, ion-exchange or inverse phase chromatography.

32. The method according to claim 31, wherein said hydrophobic chromatography is implemented using HIC butyl.

33. The method according to claim 29, wherein step ii) is carried out at a pH comprised between 6 and 9.

34. The method according to claim 27, wherein said purification step b) comprises the performance of an affinity chromatography.

35. The method according to claim 34, wherein said affinity chromatography is performed on a column of sulfated polysaccharides.

36. The method according to claim 35, wherein the sulfated polysaccharide is dextran sulfate or heparin.

37. The method according to claim 27, wherein the IL-7 conformer is characterized in the drug substance by Mass spectrometry, infra-red spectroscopy, NMR, by determining circular dichroism, by measuring the affinity toward a specific monoclonal antibody raised against said IL-7 conformer, or heparin affinity chromatography, and measured or quantified by ELISA, bioassay or the affinity of said IL-7 conformer for IL-7 receptor or a method of protein quantification.

38. The method according to claim 28, wherein IL-7 expression by the recombinant host cells is inducible, regulated or transient, so that the cell culture and IL-7 expression phases can be dissociated.

39. The composition of matter according to claim 1, wherein said IL-7 conformer is a human IL-7 conformer that is not immunogenic in humans.

40. The composition of matter according to claim 1, wherein said IL-7 conformer is a simian IL-7 conformer that is not immunogenic in non-human primates.

41. The pharmaceutical composition according to claim 13, wherein said IL-7 conformer is a human IL-7 conformer that is not immunogenic in humans.

42. The pharmaceutical composition according to claim 13, wherein said IL-7 conformer is a simian IL-7 conformer that is not immunogenic in non-human primates.

* * * * *

UNITED STATES PATENT AND TRADEMARK OFFICE
CERTIFICATE OF CORRECTION

PATENT NO. : 7,585,947 B2
APPLICATION NO. : 10/522883
DATED : September 8, 2009
INVENTOR(S) : Michel Christian Morre et al.

It is certified that error appears in the above-identified patent and that said Letters Patent is hereby corrected as shown below:

Column 11,
Line 43, "patents" should read --patients--.

Column 14,
Line 27, "from GAG and GM." should read --from GAG and GAA.--.

Column 22,
Line 30, "5'ATTC<u>CATATG</u>GATTGTGATATTAGAAGGTAAAGATGGC3'" should read --5'ATTC<u>CATATG</u>GATTGTGATATTGAAGGTAAAGATGGC3'--.

Column 23,
Line 32, "Bg1II" should read --Bg/II--.

Column 26,
Lines 42-45,
"PSIL7EcoRV5':     SEQ ID NO 14
5'A*GATAT*CATGTTCCATGTTTCTTTTAGGTA3'

*Eco*RV

PCR products were assayed by agarose gel electrophoresis" should read

--PSIL7EcoRV5':     SEQ ID NO 14
5'A*GATAT*CATGTTCCATGTTTCTTTTAGGTA3'

*Eco*RV

PSIL7MluI3'     SEQ ID NO 15
5'A*ACGCGT*TCAGTGTTCTTTAGTGCCCAT3'

*Mlu*I

PCR products were assayed by agarose gel electrophoresis--.

Column 27,
Line 45, "5'TAGCGGCCGCATGTCTCAGAGCAACCGG3'" should read --5'TA<u>GCGGCCGC</u>ATGTCTCAGAGCAACCGG3'--.
Line 47, "BclXL3'BStBI     SEQ ID NO: 15:" should read --BclXL3'BstBI     SEQ ID NO: 15:--.

UNITED STATES PATENT AND TRADEMARK OFFICE
CERTIFICATE OF CORRECTION

PATENT NO. : 7,585,947 B2
APPLICATION NO. : 10/522883
DATED : September 8, 2009
INVENTOR(S) : Michel Christian Morre et al.

It is certified that error appears in the above-identified patent and that said Letters Patent is hereby corrected as shown below:

Column 28,
Line 38, "positive done" should read --positive clone--.

Column 30,
Line 45, "DMA Quantification" should read --DNA Quantification--.

Signed and Sealed this

Twenty-ninth Day of December, 2009

David J. Kappos
*Director of the United States Patent and Trademark Office*

UNITED STATES PATENT AND TRADEMARK OFFICE
CERTIFICATE OF CORRECTION

PATENT NO. : 7,585,947 B2
APPLICATION NO. : 10/522883
DATED : September 8, 2009
INVENTOR(S) : Morre et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 630 days.

Signed and Sealed this

Fourteenth Day of September, 2010

David J. Kappos
*Director of the United States Patent and Trademark Office*

SEQUENCE LISTING

```
<160> NUMBER OF SEQ ID NOS: 23

<210> SEQ ID NO 1
<211> LENGTH: 459
<212> TYPE: DNA
<213> ORGANISM: Artificial sequence
<220> FEATURE:
<223> OTHER INFORMATION: r-hIL-7 cDNA
<220> FEATURE:
<221> NAME/KEY: CDS
<222> LOCATION: (1)..(459)
<223> OTHER INFORMATION:

<400> SEQUENCE: 1 atg gat tgt gat att gaa ggt aaa gat ggc aaa caa tac gag tcc gtt      48
Met Asp Cys Asp Ile Glu Gly Lys Asp Gly Lys Gln Tyr Glu Ser Val
1               5                   10                  15 ctg atg gtc agc atc gat caa tta ttg gac agc atg aaa gaa att ggt      96
Leu Met Val Ser Ile Asp Gln Leu Leu Asp Ser Met Lys Glu Ile Gly
            20                  25                  30 agc aat tgc ctg aat aat gaa ttt aac ttt ttt aaa aga cat atc tgt     144
Ser Asn Cys Leu Asn Asn Glu Phe Asn Phe Phe Lys Arg His Ile Cys
        35                  40                  45 gat gct aat aag gaa ggt atg ttt tta ttc cgt gct gct cgc aag ttg     192
Asp Ala Asn Lys Glu Gly Met Phe Leu Phe Arg Ala Ala Arg Lys Leu
    50                  55                  60 agg caa ttt ctt aaa atg aat agc act ggt gat ttt gat ctc cac tta     240
Arg Gln Phe Leu Lys Met Asn Ser Thr Gly Asp Phe Asp Leu His Leu
65                  70                  75                  80 tta aaa gtt tca gaa ggc aca aca ata ctg ttg aac tgc act ggc cag     288
Leu Lys Val Ser Glu Gly Thr Thr Ile Leu Leu Asn Cys Thr Gly Gln
                85                  90                  95
```

-continued

```
gtt aaa gga aga aaa cca gct gcc ctg ggt gaa gcc caa cca aca aag     336
Val Lys Gly Arg Lys Pro Ala Ala Leu Gly Glu Ala Gln Pro Thr Lys
            100                 105                 110 agt ttg gaa gaa aat aaa tct tta aag gaa cag aaa aaa ctg aat gac     384
Ser Leu Glu Glu Asn Lys Ser Leu Lys Glu Gln Lys Lys Leu Asn Asp
        115                 120                 125 ttg tgt ttc cta aag aga cta tta caa gag ata aaa act tgt tgg aat     432
Leu Cys Phe Leu Lys Arg Leu Leu Gln Glu Ile Lys Thr Cys Trp Asn
130                 135                 140 aaa att ttg atg ggc act aaa gaa cac                                 459
Lys Ile Leu Met Gly Thr Lys Glu His
145                 150
```

<210> SEQ ID NO 2
<211> LENGTH: 153
<212> TYPE: PRT
<213> ORGANISM: Artificial sequence
<220> FEATURE:
<223> OTHER INFORMATION: r-hIL-7 cDNA

<400> SEQUENCE: 2

```
Met Asp Cys Asp Ile Glu Gly Lys Asp Gly Lys Gln Tyr Glu Ser Val
1               5                   10                  15

Leu Met Val Ser Ile Asp Gln Leu Leu Asp Ser Met Lys Glu Ile Gly
            20                  25                  30

Ser Asn Cys Leu Asn Asn Glu Phe Asn Phe Lys Arg His Ile Cys
        35                  40                  45

Asp Ala Asn Lys Glu Gly Met Phe Leu Phe Arg Ala Ala Arg Lys Leu
    50                  55                  60

Arg Gln Phe Leu Lys Met Asn Ser Thr Gly Asp Phe Asp Leu His Leu
65                  70                  75                  80

Leu Lys Val Ser Glu Gly Thr Thr Ile Leu Leu Asn Cys Thr Gly Gln
                85                  90                  95

Val Lys Gly Arg Lys Pro Ala Ala Leu Gly Glu Ala Gln Pro Thr Lys
            100                 105                 110

Ser Leu Glu Glu Asn Lys Ser Leu Lys Glu Gln Lys Lys Leu Asn Asp
        115                 120                 125

Leu Cys Phe Leu Lys Arg Leu Leu Gln Glu Ile Lys Thr Cys Trp Asn
    130                 135                 140

Lys Ile Leu Met Gly Thr Lys Glu His
145                 150
```

<210> SEQ ID NO 3
<211> LENGTH: 531
<212> TYPE: DNA
<213> ORGANISM: Artificial sequence
<220> FEATURE:
<223> OTHER INFORMATION: r-hIL-7 cDNA
<220> FEATURE:
<221> NAME/KEY: CDS
<222> LOCATION: (1)..(531)
<223> OTHER INFORMATION:

<400> SEQUENCE: 3

```
atg ttc cat gtt tct ttt agg tat atc ttt gga ctt cct ccc ctg atc     48
Met Phe His Val Ser Phe Arg Tyr Ile Phe Gly Leu Pro Pro Leu Ile
1               5                   10                  15 ctt gtt ctg ttg cca gta gca tca tct gat tgt gat att gaa ggt aaa     96
Leu Val Leu Leu Pro Val Ala Ser Ser Asp Cys Asp Ile Glu Gly Lys
            20                  25                  30 gat ggc aaa caa tac gag tcc gtt ctg atg gtc agc atc gat caa tta    144
```

```
Asp Gly Lys Gln Tyr Glu Ser Val Leu Met Val Ser Ile Asp Gln Leu
        35                  40                  45 ttg gac agc atg aaa gaa att ggt agc aat tgc ctg aat aat gaa ttt    192
Leu Asp Ser Met Lys Glu Ile Gly Ser Asn Cys Leu Asn Asn Glu Phe
 50                  55                  60 aac ttt ttt aaa aga cat atc tgt gat gct aat aag gaa ggt atg ttt    240
Asn Phe Phe Lys Arg His Ile Cys Asp Ala Asn Lys Glu Gly Met Phe
 65                  70                  75                  80 tta ttc cgt gct gct cgc aag ttg agg caa ttt ctt aaa atg aat agc    288
Leu Phe Arg Ala Ala Arg Lys Leu Arg Gln Phe Leu Lys Met Asn Ser
                 85                  90                  95 act ggt gat ttt gat ctc cac tta tta aaa gtt tca gaa ggc aca aca    336
Thr Gly Asp Phe Asp Leu His Leu Leu Lys Val Ser Glu Gly Thr Thr
            100                 105                 110 ata ctg ttg aac tgc act ggc cag gtt aaa gga aga aaa cca gct gcc    384
Ile Leu Leu Asn Cys Thr Gly Gln Val Lys Gly Arg Lys Pro Ala Ala
        115                 120                 125 ctg ggt gaa gcc caa cca aca aag agt ttg gaa gaa aat aaa tct tta    432
Leu Gly Glu Ala Gln Pro Thr Lys Ser Leu Glu Glu Asn Lys Ser Leu
130                 135                 140 aag gaa cag aaa aaa ctg aat gac ttg tgt ttc cta aag aga cta tta    480
Lys Glu Gln Lys Lys Leu Asn Asp Leu Cys Phe Leu Lys Arg Leu Leu
145                 150                 155                 160 caa gag ata aaa act tgt tgg aat aaa att ttg atg ggc act aaa gaa    528
Gln Glu Ile Lys Thr Cys Trp Asn Lys Ile Leu Met Gly Thr Lys Glu
                165                 170                 175 cac                                                                531
His

<210> SEQ ID NO 4
<211> LENGTH: 177
<212> TYPE: PRT
<213> ORGANISM: Artificial sequence
<220> FEATURE:
<223> OTHER INFORMATION: r-hIL-7 cDNA

<400> SEQUENCE: 4

Met Phe His Val Ser Phe Arg Tyr Ile Phe Gly Leu Pro Pro Leu Ile
 1               5                  10                  15

Leu Val Leu Leu Pro Val Ala Ser Ser Asp Cys Asp Ile Glu Gly Lys
             20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
 50                  55                  60

Asn Phe Phe Lys Arg His Ile Cys Asp Ala Asn Lys Glu Gly Met Phe
 65                  70                  75                  80

Leu Phe Arg Ala Ala Arg Lys Leu Arg Gln Phe Leu Lys Met Asn Ser
                 85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
```

165        170        175

His

<210> SEQ ID NO 5
<211> LENGTH: 37
<212> TYPE: DNA
<213> ORGANISM: Artificial sequence
<220> FEATURE:
<223> OTHER INFORMATION: Primer

<400> SEQUENCE: 5
attccatatg gattgtgata ttgaaggtaa agatggc                    37

<210> SEQ ID NO 6
<211> LENGTH: 36
<212> TYPE: DNA
<213> ORGANISM: Artificial sequence
<220> FEATURE:
<223> OTHER INFORMATION: Primer

<400> SEQUENCE: 6
agccggatcc ttatcagtgt tctttagtgc ccatca                     36

<210> SEQ ID NO 7
<211> LENGTH: 64
<212> TYPE: DNA
<213> ORGANISM: Artificial sequence
<220> FEATURE:
<223> OTHER INFORMATION: Primer

<400> SEQUENCE: 7
tagggaattc catatggatt gtgatattga aggtaaagat ggcaaacaat acgagtccgt    60
tctg                                                               64

<210> SEQ ID NO 8
<211> LENGTH: 48
<212> TYPE: DNA
<213> ORGANISM: Artificial sequence
<220> FEATURE:
<223> OTHER INFORMATION: Primer

<400> SEQUENCE: 8
gcaagcttgc caccatgttc catgtttctt ttaggtatat ctttggac                48

<210> SEQ ID NO 9
<211> LENGTH: 36
<212> TYPE: DNA
<213> ORGANISM: Artificial sequence
<220> FEATURE:
<223> OTHER INFORMATION: ptac1 primer

<400> SEQUENCE: 9
atcgagatct aattctcatg tttgacagct tatcat                     36

<210> SEQ ID NO 10
<211> LENGTH: 38
<212> TYPE: DNA
<213> ORGANISM: Artificial sequence
<220> FEATURE:
<223> OTHER INFORMATION: ptac2 primer

<400> SEQUENCE: 10
atcgtctaga gctgtttcct gtgtgaaatt gttatccg                   38

<210> SEQ ID NO 11
<211> LENGTH: 20
<212> TYPE: DNA
<213> ORGANISM: Artificial sequence
<220> FEATURE:
<223> OTHER INFORMATION: tac promoter primer

<400> SEQUENCE: 11
ttcgtgtcgc tcaaggcgca                                            20

<210> SEQ ID NO 12
<211> LENGTH: 531
<212> TYPE: DNA
<213> ORGANISM: Artificial sequence
<220> FEATURE:
<223> OTHER INFORMATION: PS-sIL-7 cDNA
<220> FEATURE:
<221> NAME/KEY: CDS
<222> LOCATION: (1)..(531)
<223> OTHER INFORMATION:

<400> SEQUENCE: 12

```
atg ttc cat gtt tct ttt agg tat atc ttt gga ctt cct ccc ctg atc      48
Met Phe His Val Ser Phe Arg Tyr Ile Phe Gly Leu Pro Pro Leu Ile
1               5                   10                  15 ctt gtt ctg ttg cca gta gca tca tct gat tgt gat att gaa ggt aaa      96
Leu Val Leu Leu Pro Val Ala Ser Ser Asp Cys Asp Ile Glu Gly Lys
            20                  25                  30 gat ggc aaa caa tac gag tcc gtt ctg atg gtc agc atc gat caa tta     144
Asp Gly Lys Gln Tyr Glu Ser Val Leu Met Val Ser Ile Asp Gln Leu
        35                  40                  45 ttg gac agc atg aaa gaa att ggt agc aat tgc ctg aat aat gaa ttt     192
Leu Asp Ser Met Lys Glu Ile Gly Ser Asn Cys Leu Asn Asn Glu Phe
    50                  55                  60 aac ttt ttt aaa aga cat cta tgt gat gat aat aag gaa ggt atg ttt     240
Asn Phe Phe Lys Arg His Leu Cys Asp Asp Asn Lys Glu Gly Met Phe
65                  70                  75                  80 tta ttc cgt gct gct cgc aag ttg agg caa ttt ctt aaa atg aat agc     288
Leu Phe Arg Ala Ala Arg Lys Leu Arg Gln Phe Leu Lys Met Asn Ser
                85                  90                  95 act ggt gat ttt gat ctc cac tta tta aaa gtt tca gaa ggc aca aca     336
Thr Gly Asp Phe Asp Leu His Leu Leu Lys Val Ser Glu Gly Thr Thr
            100                 105                 110 ata ctg ttg aac tgc acc ggc aag gtt aaa gga aga aaa cca gct gcc     384
Ile Leu Leu Asn Cys Thr Gly Lys Val Lys Gly Arg Lys Pro Ala Ala
        115                 120                 125 ctg ggt gaa ccc caa cca aca aag agt ttg gaa gaa aat aaa tct tta     432
Leu Gly Glu Pro Gln Pro Thr Lys Ser Leu Glu Glu Asn Lys Ser Leu
    130                 135                 140 aag gaa cag aaa aaa ctg aat gac tca tgt ttc cta aag aga cta cta     480
Lys Glu Gln Lys Lys Leu Asn Asp Ser Cys Phe Leu Lys Arg Leu Leu
145                 150                 155                 160 caa aag ata aaa act tgt tgg aat aaa att ttg atg ggc act aaa gaa     528
Gln Lys Ile Lys Thr Cys Trp Asn Lys Ile Leu Met Gly Thr Lys Glu
                165                 170                 175 cac                                                                 531
His
```

<210> SEQ ID NO 13
<211> LENGTH: 177
<212> TYPE: PRT
<213> ORGANISM: Artificial sequence
<220> FEATURE:
<223> OTHER INFORMATION: PS-sIL-7 cDNA

<400> SEQUENCE: 13

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Leu Cys Asp Asp Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Lys Val Lys Gly Arg Lys Pro Ala Ala
        115                 120                 125

Leu Gly Glu Pro Gln Pro Thr Lys Ser Leu Glu Glu Asn Lys Ser Leu
    130                 135                 140

Lys Glu Gln Lys Lys Leu Asn Asp Ser Cys Phe Leu Lys Arg Leu Leu
145                 150                 155                 160

Gln Lys Ile Lys Thr Cys Trp Asn Lys Ile Leu Met Gly Thr Lys Glu
                165                 170                 175

His

<210> SEQ ID NO 14
<211> LENGTH: 28
<212> TYPE: DNA
<213> ORGANISM: Artificial sequence
<220> FEATURE:
<223> OTHER INFORMATION: BclXL5'Not1 primer

<400> SEQUENCE: 14
tagcggccgc atgtctcaga gcaaccgg                                       28

<210> SEQ ID NO 15
<211> LENGTH: 28
<212> TYPE: DNA
<213> ORGANISM: Artificial sequence
<220> FEATURE:
<223> OTHER INFORMATION: BclXL3'BstBI primer

<400> SEQUENCE: 15
acttcgaatc atttccgact gaagagtg                                       28

<210> SEQ ID NO 16
<211> LENGTH: 537
<212> TYPE: DNA
<213> ORGANISM: Artificial sequence
<220> FEATURE:
<223> OTHER INFORMATION: EPOPS-r-hIL-7 cDNA
<220> FEATURE:
<221> NAME/KEY: CDS
<222> LOCATION: (1)..(537)
<223> OTHER INFORMATION:

<400> SEQUENCE: 16 atg ggg gtg cac gaa tgt cct gcc tgg ctg tgg ctt ctc ctg tcc ctg    48
Met Gly Val His Glu Cys Pro Ala Trp Leu Trp Leu Leu Leu Ser Leu
1               5                   10                  15

```
ctg tcg ctc cct ctg ggc ctc cca gtc ctg ggc gat tgt gat att gaa        96
Leu Ser Leu Pro Leu Gly Leu Pro Val Leu Gly Asp Cys Asp Ile Glu
         20                  25                  30 ggt aaa gat ggc aaa caa tac gag tcc gtt ctg atg gtc agc atc gat       144
Gly Lys Asp Gly Lys Gln Tyr Glu Ser Val Leu Met Val Ser Ile Asp
 35                  40                  45 caa tta ttg gac agc atg aaa gaa att ggt agc aat tgc ctg aat aat       192
Gln Leu Leu Asp Ser Met Lys Glu Ile Gly Ser Asn Cys Leu Asn Asn
 50                  55                  60 gaa ttt aac ttt ttt aaa aga cat atc tgt gat gct aat aag gaa ggt       240
Glu Phe Asn Phe Phe Lys Arg His Ile Cys Asp Ala Asn Lys Glu Gly
65                  70                  75                  80 atg ttt tta ttc cgt gct gct cgc aag ttg agg caa ttt ctt aaa atg       288
Met Phe Leu Phe Arg Ala Ala Arg Lys Leu Arg Gln Phe Leu Lys Met
                 85                  90                  95 aat agc act ggt gat ttt gat ctc cac tta tta aaa gtt tca gaa ggc       336
Asn Ser Thr Gly Asp Phe Asp Leu His Leu Leu Lys Val Ser Glu Gly
            100                 105                 110 aca aca ata ctg ttg aac tgc act ggc cag gtt aaa gga aga aaa cca       384
Thr Thr Ile Leu Leu Asn Cys Thr Gly Gln Val Lys Gly Arg Lys Pro
        115                 120                 125 gct gcc ctg ggt gaa gcc caa cca aca aag agt ttg gaa gaa aat aaa       432
Ala Ala Leu Gly Glu Ala Gln Pro Thr Lys Ser Leu Glu Glu Asn Lys
    130                 135                 140 tct tta aag gaa cag aaa aaa ctg aat gac ttg tgt ttc cta aag aga       480
Ser Leu Lys Glu Gln Lys Lys Leu Asn Asp Leu Cys Phe Leu Lys Arg
145                 150                 155                 160 cta tta caa gag ata aaa act tgt tgg aat aaa att ttg atg ggc act       528
Leu Leu Gln Glu Ile Lys Thr Cys Trp Asn Lys Ile Leu Met Gly Thr
                165                 170                 175 aaa gaa cac                                                           537
Lys Glu His <210> SEQ ID NO 17
<211> LENGTH: 179
<212> TYPE: PRT
<213> ORGANISM: Artificial sequence
<220> FEATURE:
<223> OTHER INFORMATION: EPOPS-r-hIL-7 cDNA

<400> SEQUENCE: 17

Met Gly Val His Glu Cys Pro Ala Trp Leu Trp Leu Leu Ser Leu
1               5                   10                  15

Leu Ser Leu Pro Leu Gly Leu Pro Val Leu Gly Asp Cys Asp Ile Glu
            20                  25                  30

Gly Lys Asp Gly Lys Gln Tyr Glu Ser Val Leu Met Val Ser Ile Asp
         35                  40                  45

Gln Leu Leu Asp Ser Met Lys Glu Ile Gly Ser Asn Cys Leu Asn Asn
 50                  55                  60

Glu Phe Asn Phe Phe Lys Arg His Ile Cys Asp Ala Asn Lys Glu Gly
65                  70                  75                  80

Met Phe Leu Phe Arg Ala Ala Arg Lys Leu Arg Gln Phe Leu Lys Met
                 85                  90                  95

Asn Ser Thr Gly Asp Phe Asp Leu His Leu Leu Lys Val Ser Glu Gly
            100                 105                 110

Thr Thr Ile Leu Leu Asn Cys Thr Gly Gln Val Lys Gly Arg Lys Pro
        115                 120                 125

Ala Ala Leu Gly Glu Ala Gln Pro Thr Lys Ser Leu Glu Glu Asn Lys
```

-continued

```
          130                 135                 140
Ser Leu Lys Glu Gln Lys Lys Leu Asn Asp Leu Cys Phe Leu Lys Arg
145                 150                 155                 160

Leu Leu Gln Glu Ile Lys Thr Cys Trp Asn Lys Ile Leu Met Gly Thr
                165                 170                 175

Lys Glu His

<210> SEQ ID NO 18
<211> LENGTH: 519
<212> TYPE: DNA
<213> ORGANISM: Artificial sequence
<220> FEATURE:
<223> OTHER INFORMATION: HMM38PS-r-hIL-7 cDNA
<220> FEATURE:
<221> NAME/KEY: CDS
<222> LOCATION: (1)..(519)
<223> OTHER INFORMATION:

<400> SEQUENCE: 18 atg tgg tgg cgc ctg tgg tgg ctg ctg ctg ctg ctg ctg ctg tgg        48
Met Trp Trp Arg Leu Trp Trp Leu Leu Leu Leu Leu Leu Leu Trp
1               5                   10                  15 ccc atg gtg tgg gcc gat tgt gat att gaa ggt aaa gat ggc aaa caa    96
Pro Met Val Trp Ala Asp Cys Asp Ile Glu Gly Lys Asp Gly Lys Gln
            20                  25                  30 tac gag tcc gtt ctg atg gtc agc atc gat caa tta ttg gac agc atg   144
Tyr Glu Ser Val Leu Met Val Ser Ile Asp Gln Leu Leu Asp Ser Met
        35                  40                  45 aaa gaa att ggt agc aat tgc ctg aat aat gaa ttt aac ttt ttt aaa   192
Lys Glu Ile Gly Ser Asn Cys Leu Asn Asn Glu Phe Asn Phe Phe Lys
    50                  55                  60 aga cat atc tgt gat gct aat aag gaa ggt atg ttt tta ttc cgt gct   240
Arg His Ile Cys Asp Ala Asn Lys Glu Gly Met Phe Leu Phe Arg Ala
65                  70                  75                  80 gct cgc aag ttg agg caa ttt ctt aaa atg aat agc act ggt gat ttt   288
Ala Arg Lys Leu Arg Gln Phe Leu Lys Met Asn Ser Thr Gly Asp Phe
                85                  90                  95 gat ctc cac tta tta aaa gtt tca gaa ggc aca aca ata ctg ttg aac   336
Asp Leu His Leu Leu Lys Val Ser Glu Gly Thr Thr Ile Leu Leu Asn
            100                 105                 110 tgc act ggc cag gtt aaa gga aga aaa cca gct gcc ctg ggt gaa gcc   384
Cys Thr Gly Gln Val Lys Gly Arg Lys Pro Ala Ala Leu Gly Glu Ala
        115                 120                 125 caa cca aca aag agt ttg gaa gaa aat aaa tct tta aag gaa cag aaa   432
Gln Pro Thr Lys Ser Leu Glu Glu Asn Lys Ser Leu Lys Glu Gln Lys
    130                 135                 140 aaa ctg aat gac ttg tgt ttc cta aag aga cta tta caa gag ata aaa   480
Lys Leu Asn Asp Leu Cys Phe Leu Lys Arg Leu Leu Gln Glu Ile Lys
145                 150                 155                 160 act tgt tgg aat aaa att ttg atg ggc act aaa gaa cac                519
Thr Cys Trp Asn Lys Ile Leu Met Gly Thr Lys Glu His
                165                 170

<210> SEQ ID NO 19
<211> LENGTH: 173
<212> TYPE: PRT
<213> ORGANISM: Artificial sequence
<220> FEATURE:
<223> OTHER INFORMATION: HMM38PS-r-hIL-7 cDNA

<400> SEQUENCE: 19

Met Trp Trp Arg Leu Trp Trp Leu Leu Leu Leu Leu Leu Leu Trp
```

```
1               5                   10                  15
Pro Met Val Trp Ala Asp Cys Asp Ile Glu Gly Lys Asp Gly Lys Gln
                20                  25                  30

Tyr Glu Ser Val Leu Met Val Ser Ile Asp Gln Leu Leu Asp Ser Met
            35                  40                  45

Lys Glu Ile Gly Ser Asn Cys Leu Asn Asn Glu Phe Asn Phe Phe Lys
        50                  55                  60

Arg His Ile Cys Asp Ala Asn Lys Glu Gly Met Phe Leu Phe Arg Ala
65                  70                  75                  80

Ala Arg Lys Leu Arg Gln Phe Leu Lys Met Asn Ser Thr Gly Asp Phe
                85                  90                  95

Asp Leu His Leu Leu Lys Val Ser Glu Gly Thr Thr Ile Leu Leu Asn
            100                 105                 110

Cys Thr Gly Gln Val Lys Gly Arg Lys Pro Ala Ala Leu Gly Glu Ala
        115                 120                 125

Gln Pro Thr Lys Ser Leu Glu Glu Asn Lys Ser Leu Lys Glu Gln Lys
    130                 135                 140

Lys Leu Asn Asp Leu Cys Phe Leu Lys Arg Leu Leu Gln Glu Ile Lys
145                 150                 155                 160

Thr Cys Trp Asn Lys Ile Leu Met Gly Thr Lys Glu His
                165                 170

<210> SEQ ID NO 20
<211> LENGTH: 537
<212> TYPE: DNA
<213> ORGANISM: Artificial sequence
<220> FEATURE:
<223> OTHER INFORMATION: EPOPS-sIL-7 cDNA
<220> FEATURE:
<221> NAME/KEY: CDS
<222> LOCATION: (1)..(537)
<223> OTHER INFORMATION:

<400> SEQUENCE: 20 atg ggg gtg cac gaa tgt cct gcc tgg ctg tgg ctt ctc ctg tcc ctg       48
Met Gly Val His Glu Cys Pro Ala Trp Leu Trp Leu Leu Leu Ser Leu
1               5                   10                  15 ctg tcg ctc cct ctg ggc ctc cca gtc ctg ggc gat tgt gat att gaa       96
Leu Ser Leu Pro Leu Gly Leu Pro Val Leu Gly Asp Cys Asp Ile Glu
                20                  25                  30 ggt aaa gat ggc aaa caa tac gag tcc gtt ctg atg gtc agc atc gat      144
Gly Lys Asp Gly Lys Gln Tyr Glu Ser Val Leu Met Val Ser Ile Asp
            35                  40                  45 caa tta ttg gac agc atg aaa gaa att ggt agc aat tgc ctg aat aat      192
Gln Leu Leu Asp Ser Met Lys Glu Ile Gly Ser Asn Cys Leu Asn Asn
        50                  55                  60 gaa ttt aac ttt ttt aaa aga cat cta tgt gat gat aat aag gaa ggt      240
Glu Phe Asn Phe Phe Lys Arg His Leu Cys Asp Asp Asn Lys Glu Gly
65                  70                  75                  80 atg ttt tta ttc cgt gct gct cgc aag ttg agg caa ttt ctt aaa atg      288
Met Phe Leu Phe Arg Ala Ala Arg Lys Leu Arg Gln Phe Leu Lys Met
                85                  90                  95 aat agc act ggt gat ttt gat ctc cac tta tta aaa gtt tca gaa ggc      336
Asn Ser Thr Gly Asp Phe Asp Leu His Leu Leu Lys Val Ser Glu Gly
            100                 105                 110 aca aca ata ctg ttg aac tgc acc ggc aag gtt aaa gga aga aaa cca      384
Thr Thr Ile Leu Leu Asn Cys Thr Gly Lys Val Lys Gly Arg Lys Pro
        115                 120                 125 gct gcc ctg ggt gaa ccc caa cca aca aag agt ttg gaa gaa aat aaa      432
```

```
Ala Ala Leu Gly Glu Pro Gln Pro Thr Lys Ser Leu Glu Glu Asn Lys
        130                 135                 140 tct tta aag gaa cag aaa aaa ctg aat gac tca tgt ttc cta aag aga      480
Ser Leu Lys Glu Gln Lys Lys Leu Asn Asp Ser Cys Phe Leu Lys Arg
145                 150                 155                 160 cta cta caa aag ata aaa act tgt tgg aat aaa att ttg atg ggc act      528
Leu Leu Gln Lys Ile Lys Thr Cys Trp Asn Lys Ile Leu Met Gly Thr
                165                 170                 175 aaa gaa cac                                                          537
Lys Glu His
```

<210> SEQ ID NO 21
<211> LENGTH: 179
<212> TYPE: PRT
<213> ORGANISM: Artificial sequence
<220> FEATURE:
<223> OTHER INFORMATION: EPOPS-sIL-7 cDNA

<400> SEQUENCE: 21

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Asp Cys Asp Ile Glu
                20                  25                  30

Gly Lys Asp Gly Lys Gln Tyr Glu Ser Val Leu Met Val Ser Ile Asp
            35                  40                  45

Gln Leu Leu Asp Ser Met Lys Glu Ile Gly Ser Asn Cys Leu Asn Asn
        50                  55                  60

Glu Phe Asn Phe Phe Lys Arg His Leu Cys Asp Asp Asn Lys Glu Gly
65                  70                  75                  80

Met Phe Leu Phe Arg Ala Ala Arg Lys Leu Arg Gln Phe Leu Lys Met
                85                  90                  95

Asn Ser Thr Gly Asp Phe Asp Leu His Leu Leu Lys Val Ser Glu Gly
                100                 105                 110

Thr Thr Ile Leu Leu Asn Cys Thr Gly Lys Val Lys Gly Arg Lys Pro
            115                 120                 125

Ala Ala Leu Gly Glu Pro Gln Pro Thr Lys Ser Leu Glu Glu Asn Lys
        130                 135                 140

Ser Leu Lys Glu Gln Lys Lys Leu Asn Asp Ser Cys Phe Leu Lys Arg
145                 150                 155                 160

Leu Leu Gln Lys Ile Lys Thr Cys Trp Asn Lys Ile Leu Met Gly Thr
                165                 170                 175

Lys Glu His
```

<210> SEQ ID NO 22
<211> LENGTH: 519
<212> TYPE: DNA
<213> ORGANISM: Artificial sequence
<220> FEATURE:
<223> OTHER INFORMATION: HMM38PS-sIL-7
<220> FEATURE:
<221> NAME/KEY: CDS
<222> LOCATION: (1)..(519)
<223> OTHER INFORMATION:

<400> SEQUENCE: 22

```
atg tgg tgg cgc ctg tgg tgg ctg ctg ctg ctg ctg ctg ctg tgg           48
Met Trp Trp Arg Leu Trp Trp Leu Leu Leu Leu Leu Leu Leu Trp
1               5                   10                  15 ccc atg gtg tgg gcc gat tgt gat att gaa ggt aaa gat ggc aaa caa       96
Pro Met Val Trp Ala Asp Cys Asp Ile Glu Gly Lys Asp Gly Lys Gln
```

|   |   |   | 20 |   |   |   | 25 |   |   |   | 30 |   |   |   |   |
|---|---|---|---|---|---|---|---|---|---|---|---|---|---|---|---|

```
tac gag tcc gtt ctg atg gtc agc atc gat caa tta ttg gac agc atg      144
Tyr Glu Ser Val Leu Met Val Ser Ile Asp Gln Leu Leu Asp Ser Met
         35                  40                  45 aaa gaa att ggt agc aat tgc ctg aat aat gaa ttt aac ttt ttt aaa      192
Lys Glu Ile Gly Ser Asn Cys Leu Asn Asn Glu Phe Asn Phe Phe Lys
 50                  55                  60 aga cat cta tgt gat gat aat aag gaa ggt atg ttt tta ttc cgt gct      240
Arg His Leu Cys Asp Asp Asn Lys Glu Gly Met Phe Leu Phe Arg Ala
65                  70                  75                  80 gct cgc aag ttg agg caa ttt ctt aaa atg aat agc act ggt gat ttt      288
Ala Arg Lys Leu Arg Gln Phe Leu Lys Met Asn Ser Thr Gly Asp Phe
                 85                  90                  95 gat ctc cac tta tta aaa gtt tca gaa ggc aca aca ata ctg ttg aac      336
Asp Leu His Leu Leu Lys Val Ser Glu Gly Thr Thr Ile Leu Leu Asn
            100                 105                 110 tgc acc ggc aag gtt aaa gga aga aaa cca gct gcc ctg ggt gaa ccc      384
Cys Thr Gly Lys Val Lys Gly Arg Lys Pro Ala Ala Leu Gly Glu Pro
        115                 120                 125 caa cca aca aag agt ttg gaa gaa aat aaa tct tta aag gaa cag aaa      432
Gln Pro Thr Lys Ser Leu Glu Glu Asn Lys Ser Leu Lys Glu Gln Lys
    130                 135                 140 aaa ctg aat gac tca tgt ttc cta aag aga cta cta caa aag ata aaa      480
Lys Leu Asn Asp Ser Cys Phe Leu Lys Arg Leu Leu Gln Lys Ile Lys
145                 150                 155                 160 act tgt tgg aat aaa att ttg atg ggc act aaa gaa cac                  519
Thr Cys Trp Asn Lys Ile Leu Met Gly Thr Lys Glu His
                165                 170

<210> SEQ ID NO 23
<211> LENGTH: 173
<212> TYPE: PRT
<213> ORGANISM: Artificial sequence
<220> FEATURE:
<223> OTHER INFORMATION: HMM38PS-sIL-7

<400> SEQUENCE: 23

Met Trp Trp Arg Leu Trp Trp Leu Leu Leu Leu Leu Leu Leu Leu Trp
 1               5                  10                  15

Pro Met Val Trp Ala Asp Cys Asp Ile Glu Gly Lys Asp Gly Lys Gln
             20                  25                  30

Tyr Glu Ser Val Leu Met Val Ser Ile Asp Gln Leu Leu Asp Ser Met
         35                  40                  45

Lys Glu Ile Gly Ser Asn Cys Leu Asn Asn Glu Phe Asn Phe Phe Lys
 50                  55                  60

Arg His Leu Cys Asp Asp Asn Lys Glu Gly Met Phe Leu Phe Arg Ala
65                  70                  75                  80

Ala Arg Lys Leu Arg Gln Phe Leu Lys Met Asn Ser Thr Gly Asp Phe
                 85                  90                  95

Asp Leu His Leu Leu Lys Val Ser Glu Gly Thr Thr Ile Leu Leu Asn
            100                 105                 110

Cys Thr Gly Lys Val Lys Gly Arg Lys Pro Ala Ala Leu Gly Glu Pro
        115                 120                 125

Gln Pro Thr Lys Ser Leu Glu Glu Asn Lys Ser Leu Lys Glu Gln Lys
    130                 135                 140

Lys Leu Asn Asp Ser Cys Phe Leu Lys Arg Leu Leu Gln Lys Ile Lys
145                 150                 155                 160
```

```
Thr Cys Trp Asn Lys Ile Leu Met Gly Thr Lys Glu His
                165                 170
```